(12) United States Patent
Jung et al.

(10) Patent No.: US 12,010,912 B2
(45) Date of Patent: Jun. 11, 2024

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boonjae Jang, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 800 days.

(21) Appl. No.: 17/049,820

(22) PCT Filed: Jul. 24, 2019

(86) PCT No.: PCT/KR2019/009192
§ 371 (c)(1),
(2) Date: Oct. 22, 2020

(87) PCT Pub. No.: WO2020/022779
PCT Pub. Date: Jan. 30, 2020

(65) Prior Publication Data
US 2021/0265572 A1    Aug. 26, 2021

(30) Foreign Application Priority Data

Jul. 24, 2018   (KR) .................. 10-2018-0086192
Jul. 24, 2019   (KR) .................. 10-2019-0089573

(51) Int. Cl.
*H01L 51/50*      (2006.01)
*C07D 405/14*     (2006.01)
(Continued)

(52) U.S. Cl.
CPC ......... *H10K 85/654* (2023.02); *C07D 405/14* (2013.01); *C07D 409/14* (2013.01);
(Continued)

(58) Field of Classification Search
None
See application file for complete search history.

(56) References Cited

U.S. PATENT DOCUMENTS 9,334,260 B2      5/2016 Parham et al.
2011/0309343 A1   12/2011 Langer et al.
(Continued)

FOREIGN PATENT DOCUMENTS

CN   102770427 A   11/2012
CN   106316925 A    1/2017
(Continued)

*Primary Examiner* — Gregory D Clark
(74) *Attorney, Agent, or Firm* — Bryan Cave Leighton Paisner LLP

(57) ABSTRACT

A novel heterocyclic compound of Chemical Formula 1 and organic light emitting device including the same.

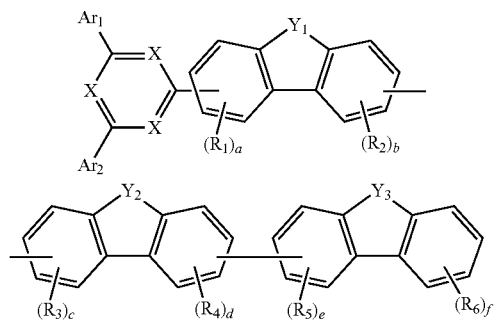

7 Claims, 1 Drawing Sheet

(51) Int. Cl.
*C07D 409/14* (2006.01)
*C09K 11/06* (2006.01)
*H10K 85/60* (2023.01)
*H10K 50/11* (2023.01)
*H10K 101/00* (2023.01)
*H10K 101/10* (2023.01)

(52) U.S. Cl.
CPC .......... *C09K 11/06* (2013.01); *H10K 85/6574* (2023.02); *H10K 85/6576* (2023.02); *C09K 2211/1018* (2013.01); *H10K 50/11* (2023.02); *H10K 2101/10* (2023.02); *H10K 2101/90* (2023.02)

(56) References Cited

U.S. PATENT DOCUMENTS

| | | |
|---|---|---|
| 2012/0223276 A1 | 9/2012 | Parham et al. |
| 2014/0158992 A1 | 6/2014 | Xia et al. |
| 2014/0252280 A1 | 9/2014 | Schaefer et al. |
| 2016/0226001 A1 | 8/2016 | Parham et al. |
| 2017/0186965 A1 | 6/2017 | Parham et al. |
| 2017/0194569 A1 | 7/2017 | Kim et al. |
| 2018/0037546 A1 | 2/2018 | Sugino et al. |
| 2019/0047991 A1 | 2/2019 | Jung et al. |
| 2022/0165961 A1 | 5/2022 | Parham et al. |

FOREIGN PATENT DOCUMENTS

| | | | |
|---|---|---|---|
| CN | 106459018 A | 2/2017 | |
| CN | 106661006 A | 5/2017 | |
| CN | 107250132 A | 10/2017 | |
| CN | 108191842 A | 6/2018 | |
| KR | 10-2000-0051826 A | 8/2000 | |
| KR | 10-2012-0129733 A | 11/2012 | |
| KR | 2016-0028524 * | 4/2015 | ............ H01L 51/50 |
| KR | 10-2016-0028524 A | 3/2016 | |
| KR | 10-2017-0075877 A | 7/2017 | |
| KR | 10-2017-0094774 A | 8/2017 | |
| KR | 10-1856728 B1 | 5/2018 | |
| KR | 10-2018-0061076 A | 6/2018 | |
| WO | 03012890 A2 | 2/2003 | |
| WO | 2006128800 A1 | 12/2006 | |
| WO | 2011157790 A1 | 12/2011 | |
| WO | 2011158204 A1 | 12/2011 | |
| WO | 2012100901 A1 | 8/2012 | |
| WO | 2013068376 A1 | 5/2013 | |
| WO | 2014042420 A1 | 3/2014 | |
| WO | 2015036080 A1 | 3/2015 | |
| WO | 2018084423 A2 | 5/2018 | |
| WO | 2019031679 A1 | 2/2019 | |

\* cited by examiner

【FIG. 1】
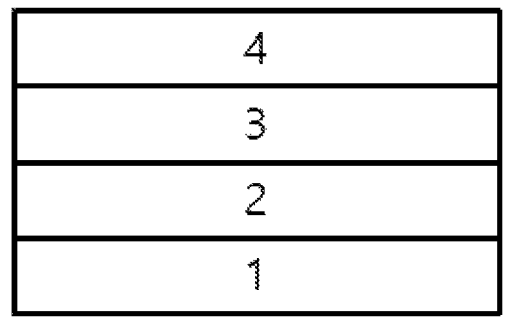
【FIG. 2】
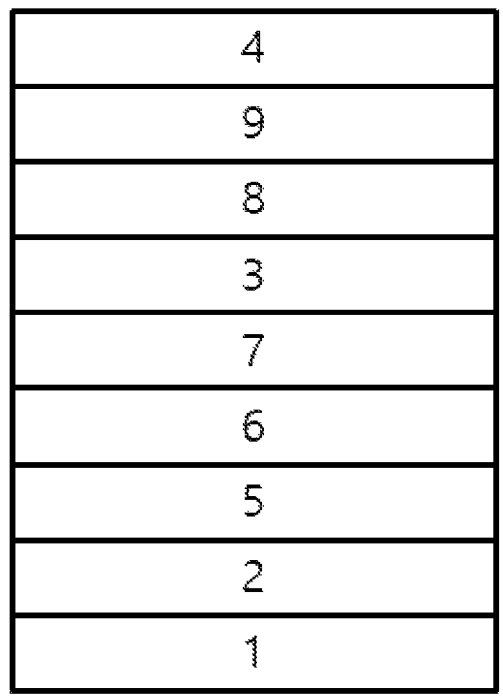

HETEROCYCLIC COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/009192, filed on Jul. 24, 2019, which claims priority to or the benefit of Korean Patent Application No. 10-2018-0086192 filed with the Korean Intellectual Property Office on Jul. 24, 2018, and Korean Patent Application No. 10-2019-0089573 filed with the Korean Intellectual Property Office on Jul. 24, 2019, the disclosures of which are incorporated herein by reference in their entirety.

FIELD OF THE INVENTION

The present invention relates to a novel heterocyclic compound and to an organic light emitting device comprising the same.

BACKGROUND OF THE INVENTION

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE (Patent Literature 0001) Korean Patent Laid-open Publication No. 10-2000-0051826

SUMMARY OF THE INVENTION

Technical Problem

It is an object of the present invention to provide a novel heterocyclic compound and an organic light emitting device including the same.

Technical Solution

In one aspect of the invention, there is provided a compound of the following Chemical Formula 1:

[Chemical Formula 1]

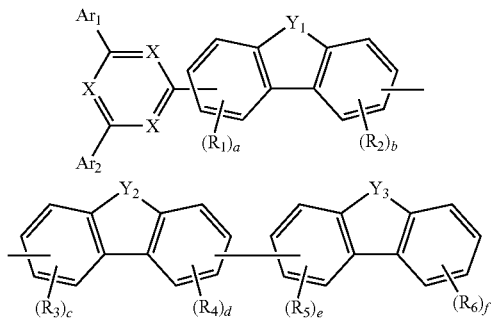

wherein, in Chemical Formula 1,
each X is independently N or CH, with the proviso that at least two of X are N,
$Y_1$ is N, O or S,
$Y_2$ and $Y_3$ are each independently O or S,
$Ar_1$ and $Ar_2$ are each independently substituted or unsubstituted $C_{6-60}$ aryl; or substituted or unsubstituted $C_{2-60}$ heteroaryl containing at least one heteroatom selected from the group consisting of N, O, S and Si,
$R_1$ to $R_6$ are each independently halogen; hydroxy; cyano; nitro; amino; substituted or unsubstituted $C_{1-60}$ alkyl; substituted or unsubstituted $C_{1-60}$ haloalkyl; substituted or unsubstituted $C_{1-60}$ thioalkyl; substituted or unsubstituted $C_{1-60}$ alkoxy; substituted or unsubstituted $C_{1-60}$ haloalkoxy; substituted or unsubstituted $C_{3-60}$ cycloalkyl; substituted or unsubstituted $C_{2-60}$ alkenyl; substituted or unsubstituted $C_{6-60}$ aryl; substituted or unsubstituted $C_{6-60}$ aryloxy; or substituted or unsubstituted $C_{2-60}$ heteroaryl containing at least one of O, N, Si and S,
a, b, c, d and e are each independently an integer of 0 to 3, and
f is an integer of 0 to 4.

In another aspect of the invention, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

Advantageous Effects

The compound of Chemical Formula 1 described above can be used as a material of an organic material layer of an organic light emitting device and may improve the efficiency, achieve low driving voltage and/or improve lifetime characteristics in the organic light emitting device. In particular, the compound of Chemical Formula 1 may be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, an electron blocking layer 7, a light emitting layer 3, an electron transport layer 8, an electron injection layer 9, and a cathode 4.

DETAILED DESCRIPTION OF THE EMBODIMENTS

Hereinafter, embodiments of the present invention will be described in more detail to facilitate understanding of the invention.

One embodiment of the invention provides a compound of Chemical Formula 1.

As used herein, the notation ┊ and ─┼─ mean a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structural formulae but is not limited thereto.

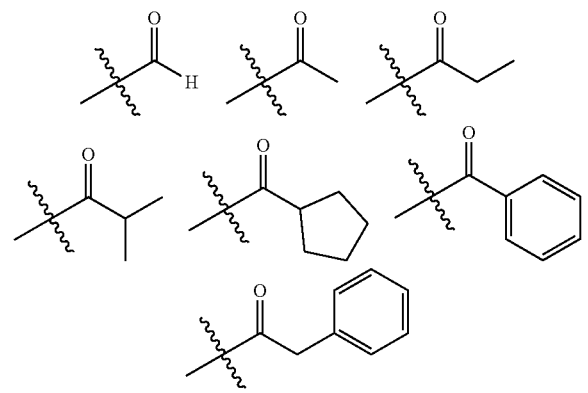

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulae, but is not limited thereto.

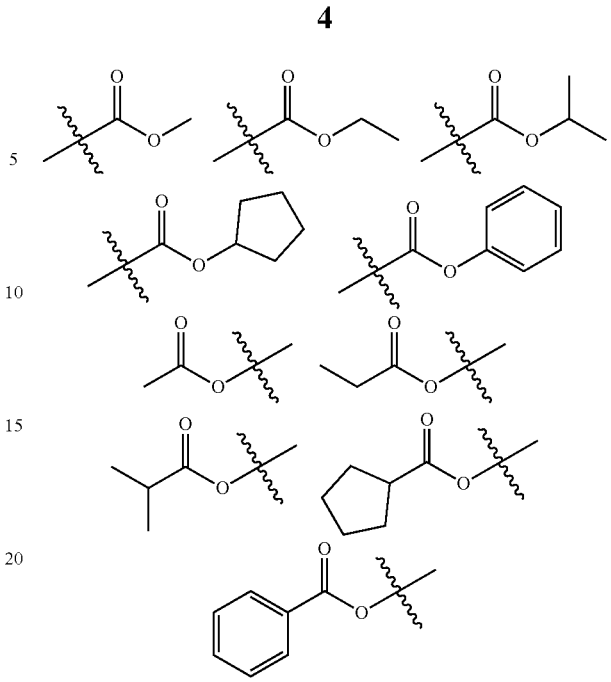

In the present specification, the number of carbon atoms of an imide group is not particularly limited, but is preferably 1 to 25. Specifically, the imide group may be a compound having the following structural formulae, but is not limited thereto.

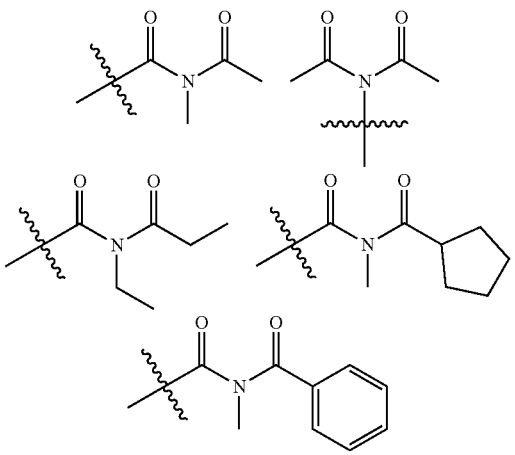

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group may be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohectylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, iso-hexyl, 2-methylpentyl, 4-methylhexyl, 5-methylhexyl, and the like, but are not limited thereto.

In the present specification, the alkenyl group may be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopro-penyl, 1-butenyl, 2-butenyl, 3-butenyl, 1-pentenyl, 2-pente-nyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphe-nyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimeth-ylcyclohexyl, 4-tert-butylcyclohexyl, cycloheptyl, cyclooc-tyl, and the like, but are not limited thereto.

In the present specification, an aryl group is not particu-larly limited, but preferably has 6 to 60 carbon atoms, and may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be connected with each other to form a spiro structure. In the case where the fluorenyl group is substituted,

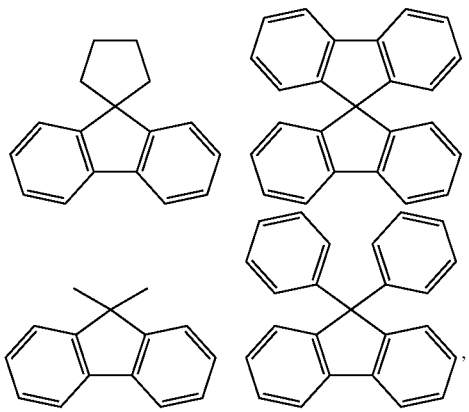

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidi-nyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothi-ophene group, a dibenzothiophene group, a benzofuranyl group, a phenanthroline group, an isoxazolyl group, an thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heteroaryl can be applied except that the heteroarylene is a divalent group. In the present specifica-tion, the aforementioned description of the aryl group or cycloalkyl group can be applied except that the hydrocarbon ring is not a monovalent group but formed by combining two substituent groups. In the present specification, the afore-mentioned description of the heteroaryl can be applied, except that the heterocycle is not a monovalent group but formed by combining two substituent groups.

Preferably, X are all N.
Preferably, $Ar_1$ and $Ar_2$ are phenyl.
Preferably, $Y_1$ is O or S.
Preferably, a, b, c, d, e and f are 0.

Preferably, the compound of Chemical Formula 1 may be selected from the group consisting of the following compounds.
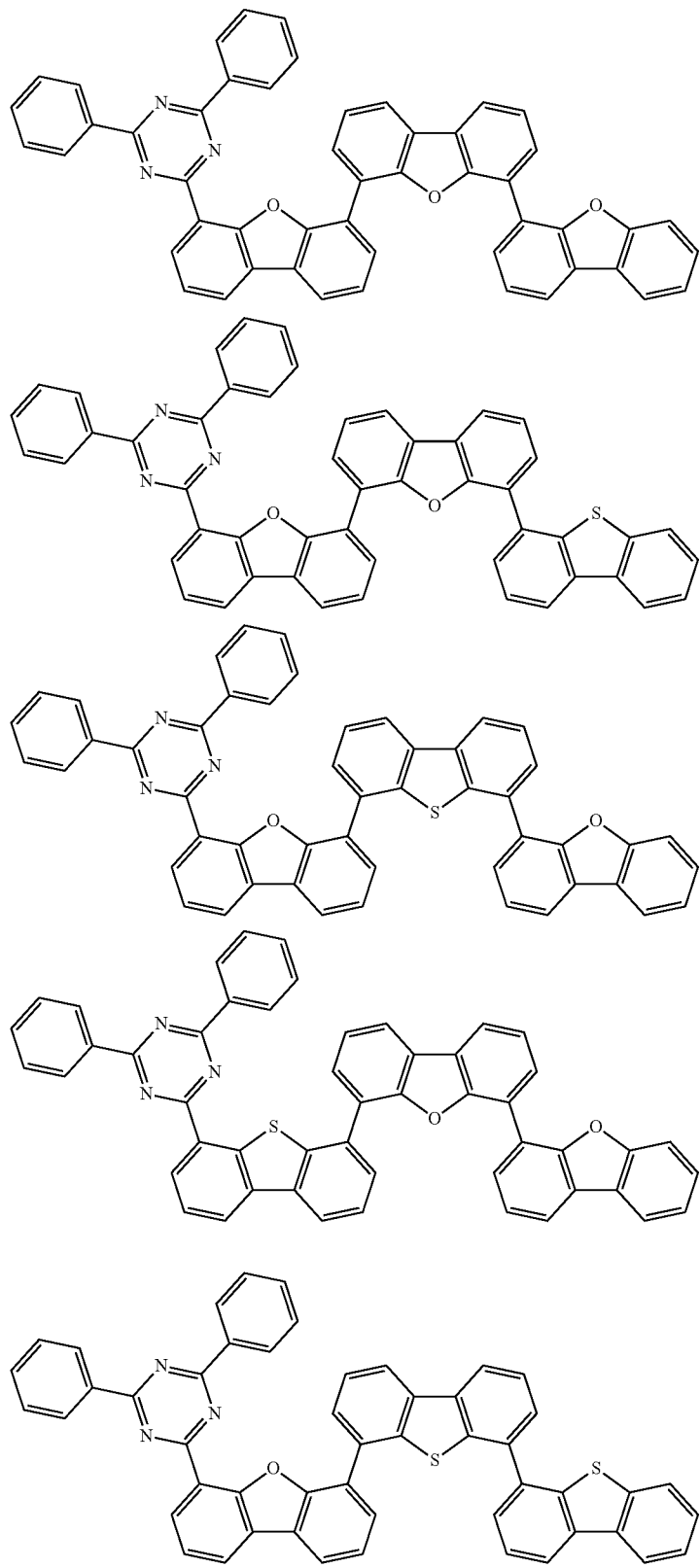

-continued
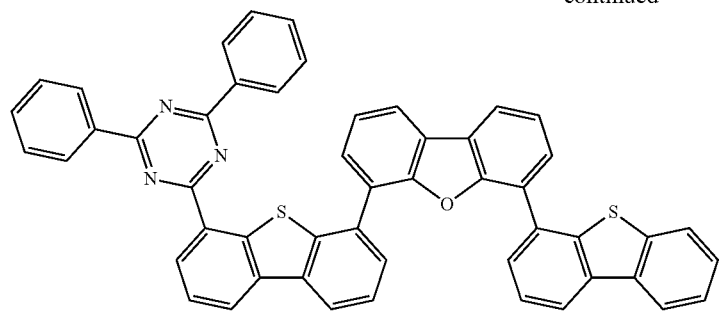
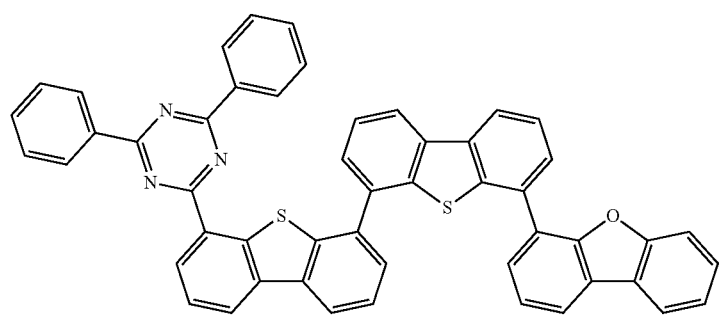
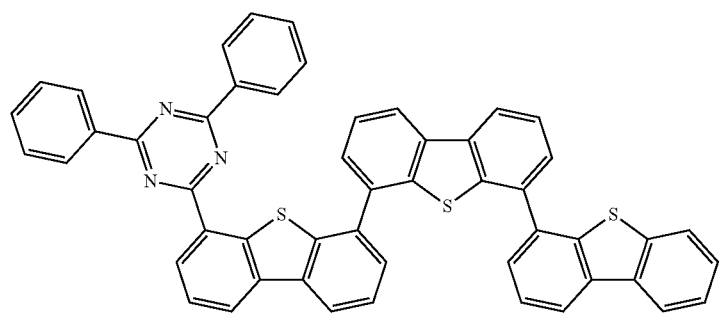
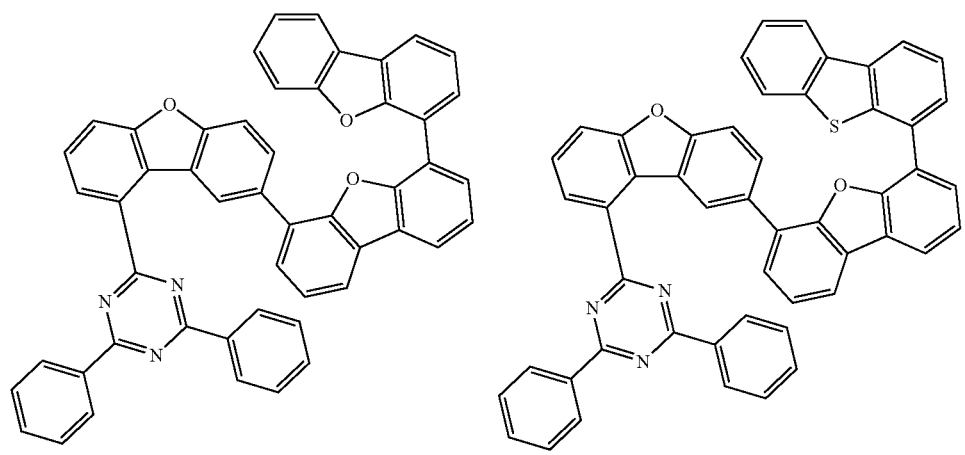

-continued
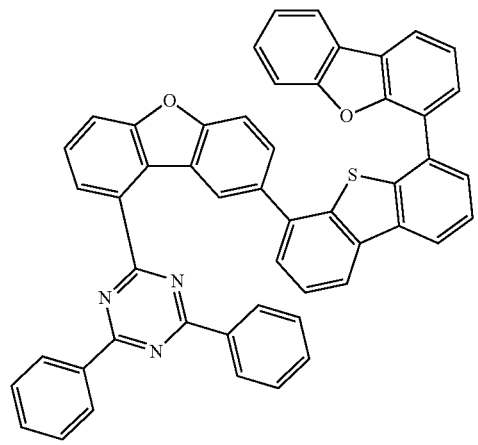
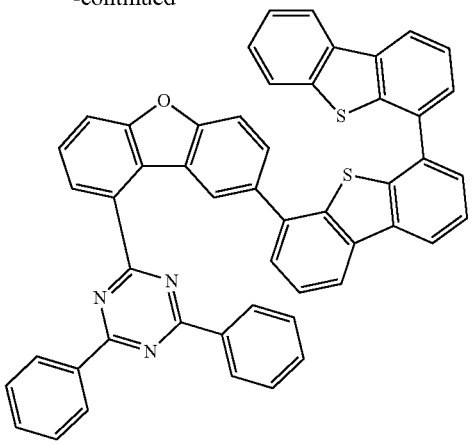
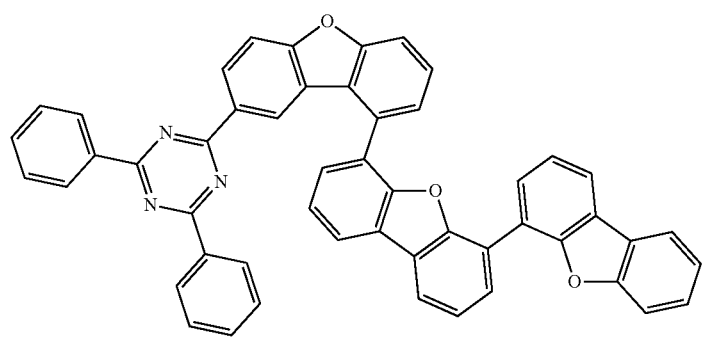
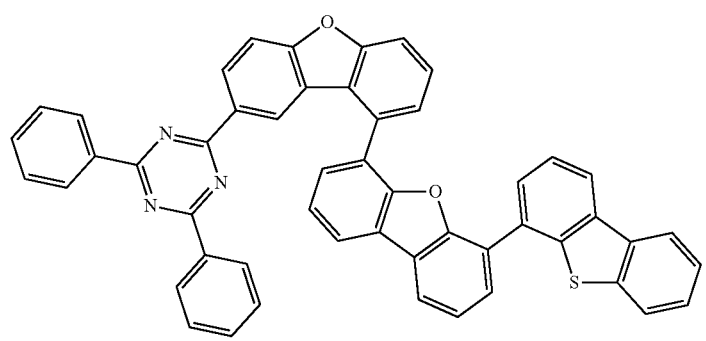
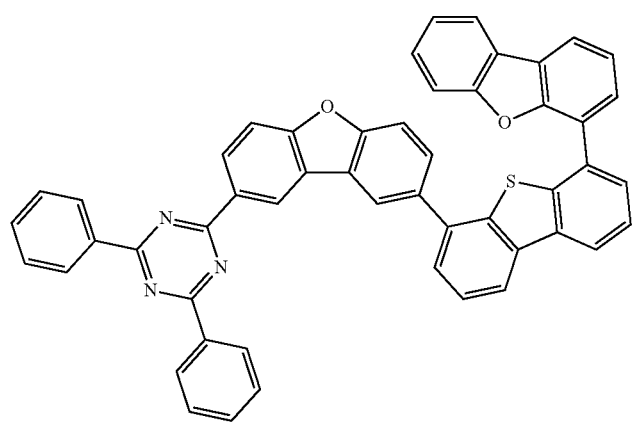

-continued
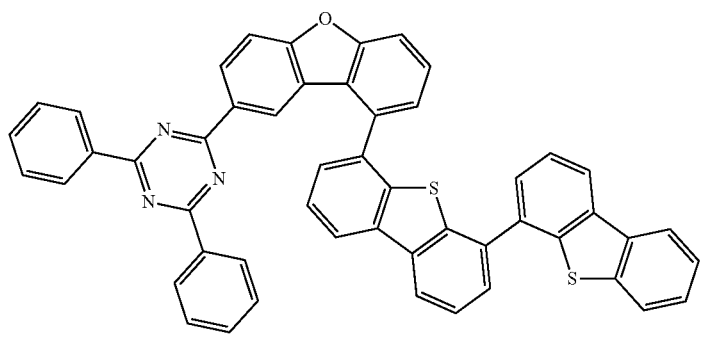
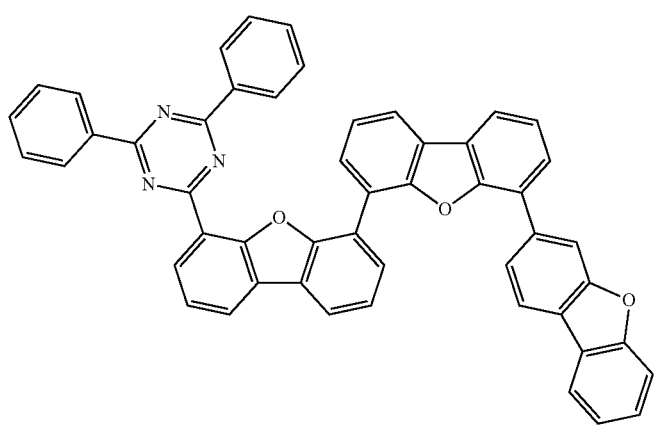
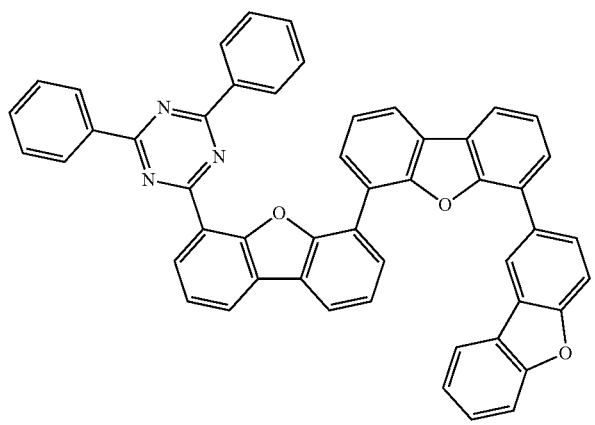
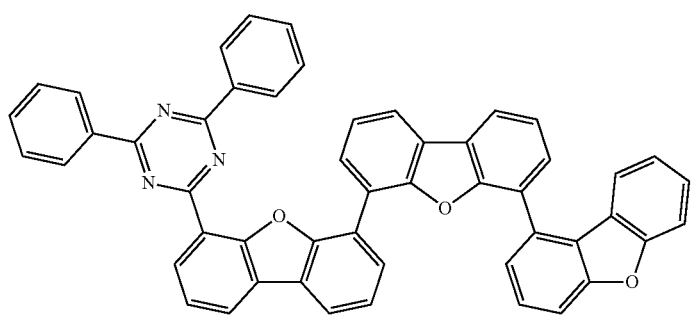

-continued
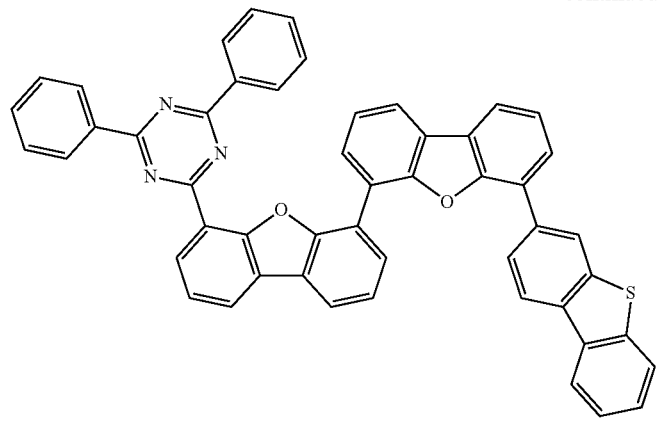

-continued
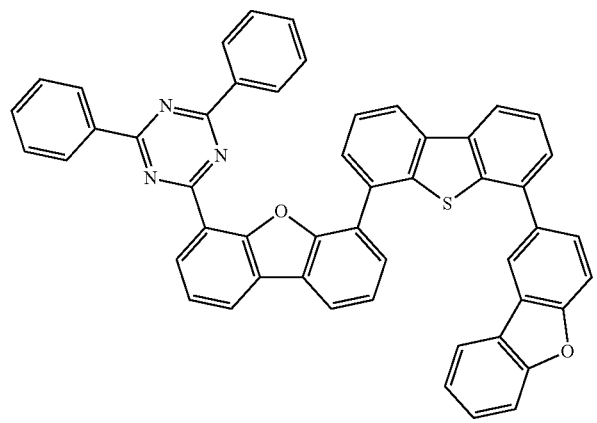
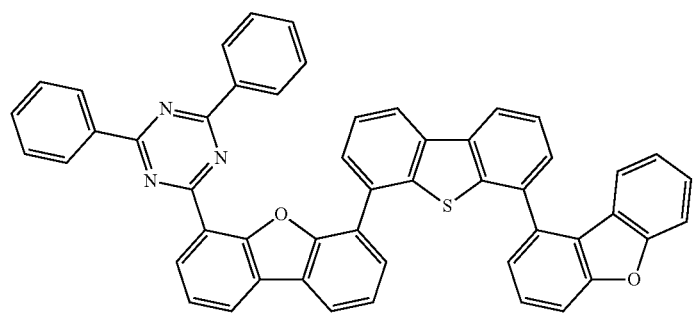
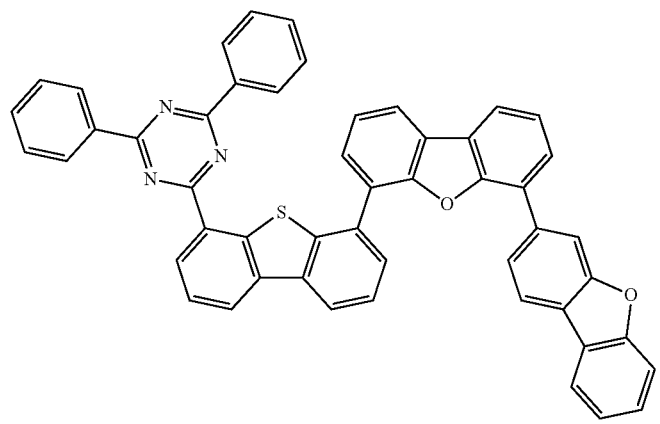
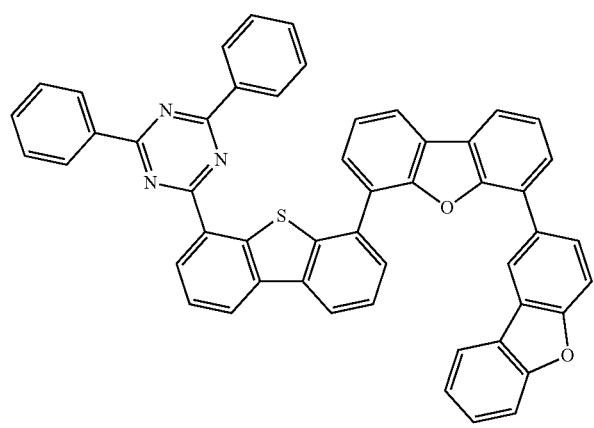

-continued
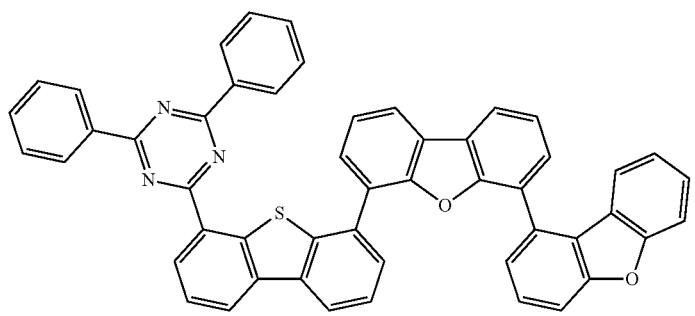
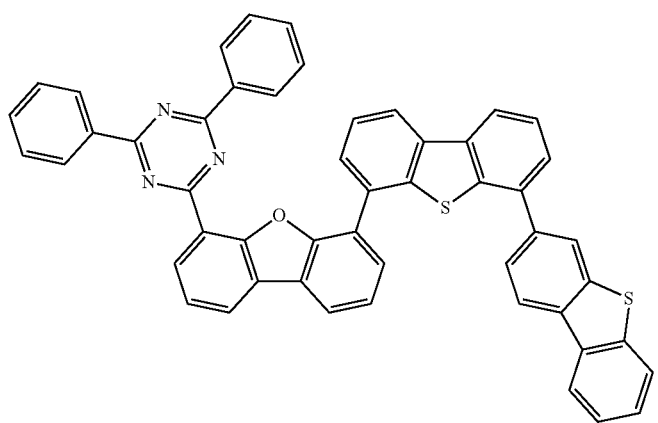
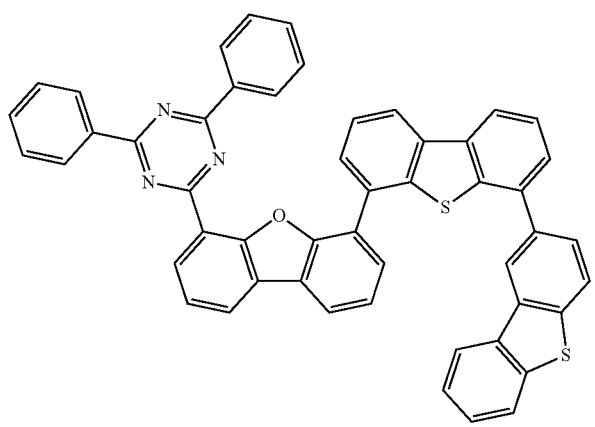
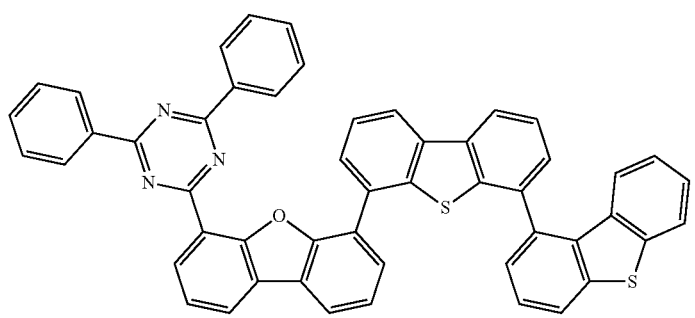

-continued
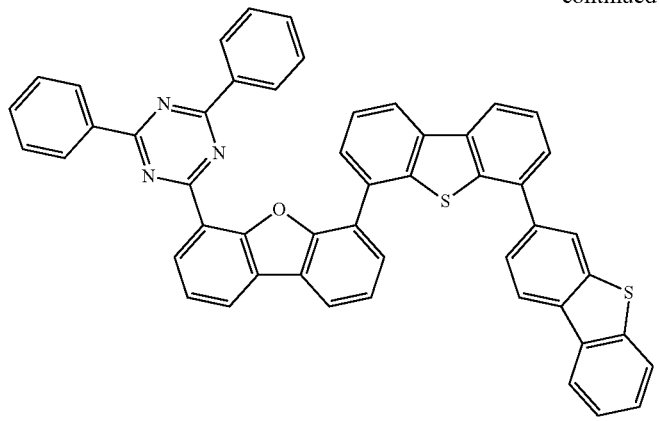
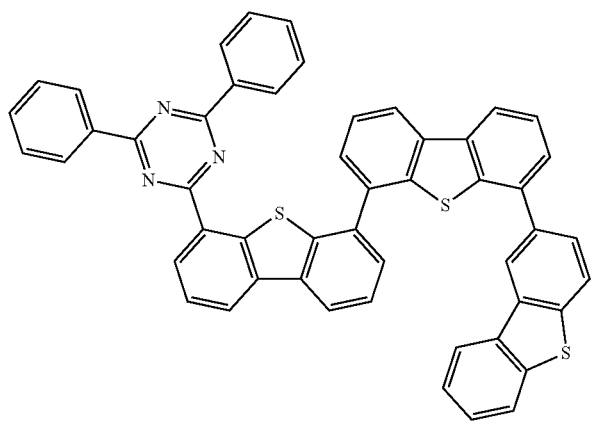
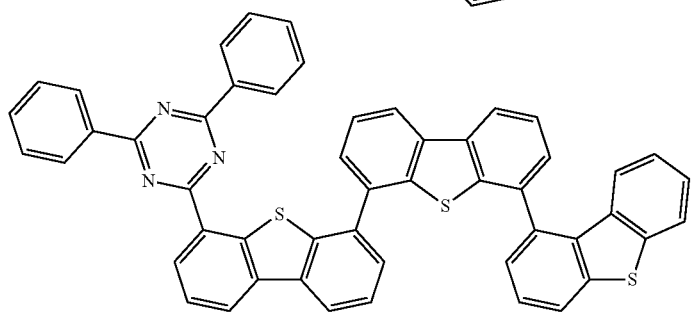
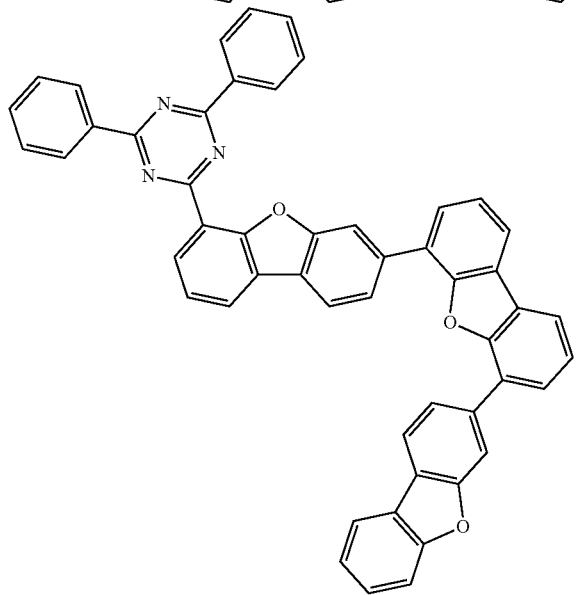

-continued
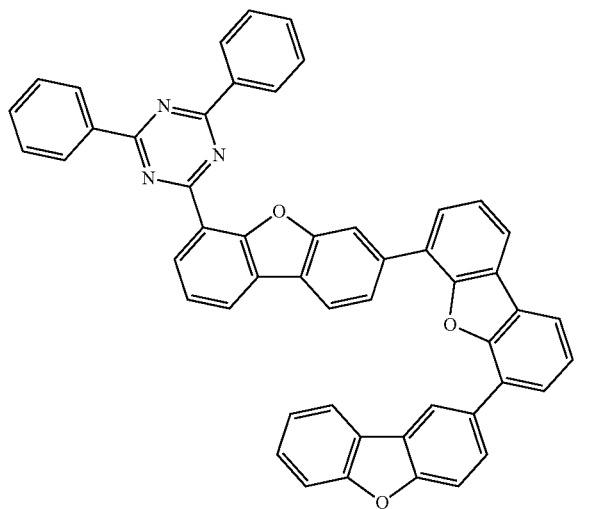
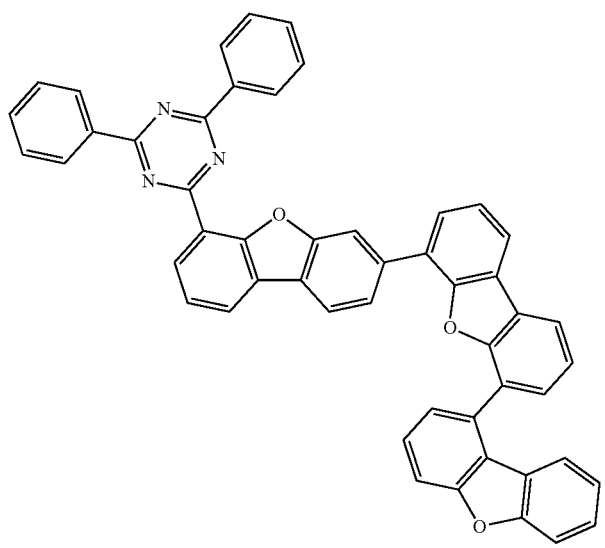
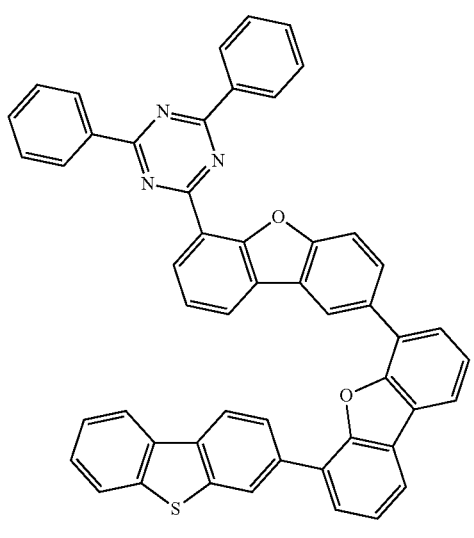
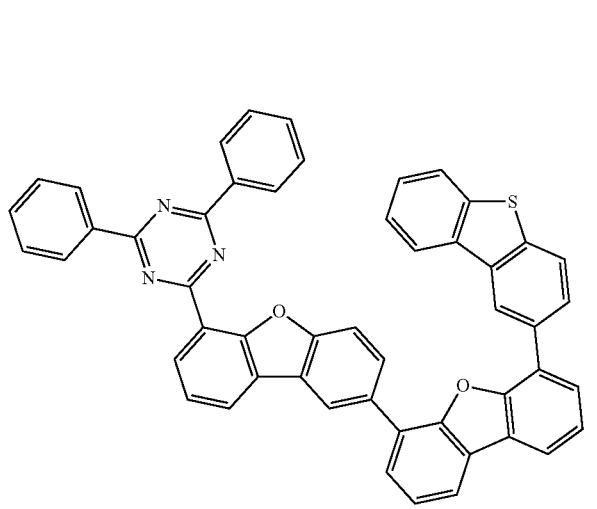
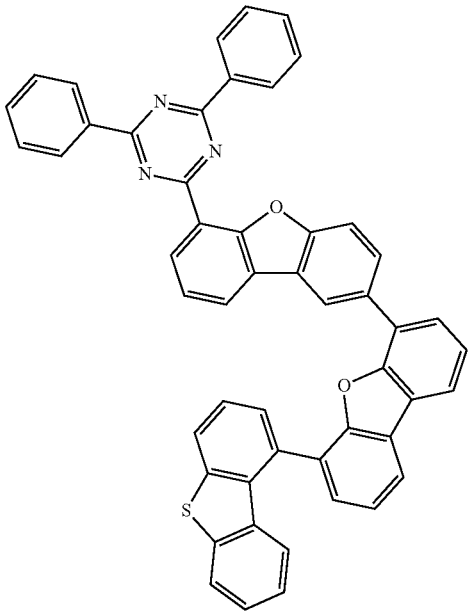

-continued
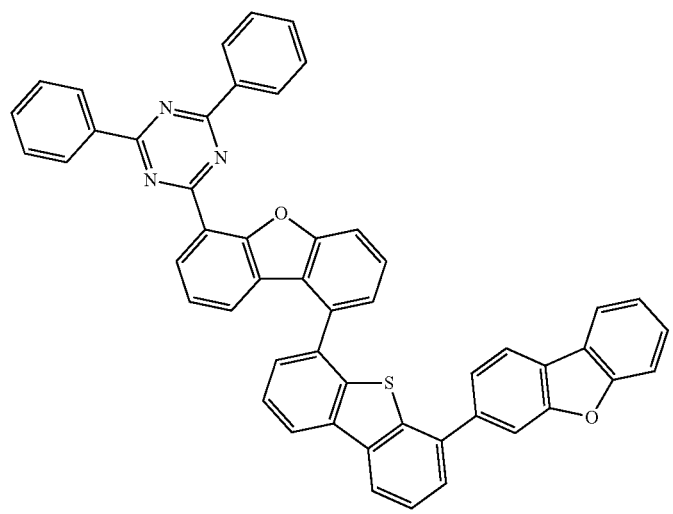
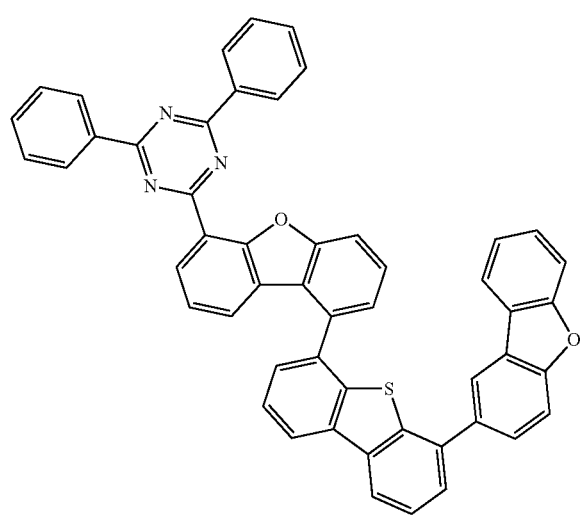
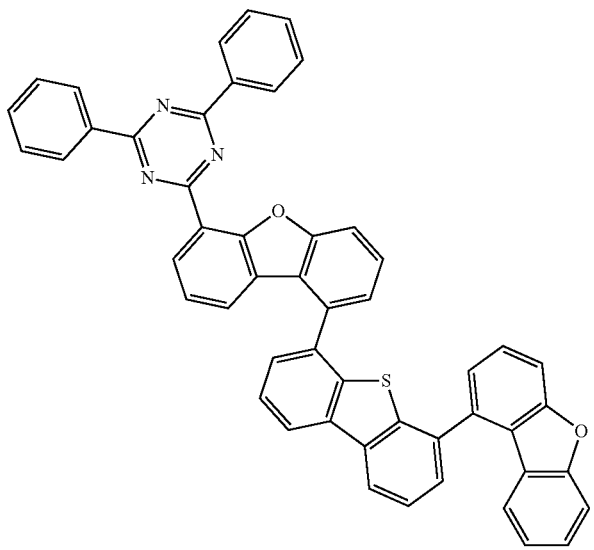
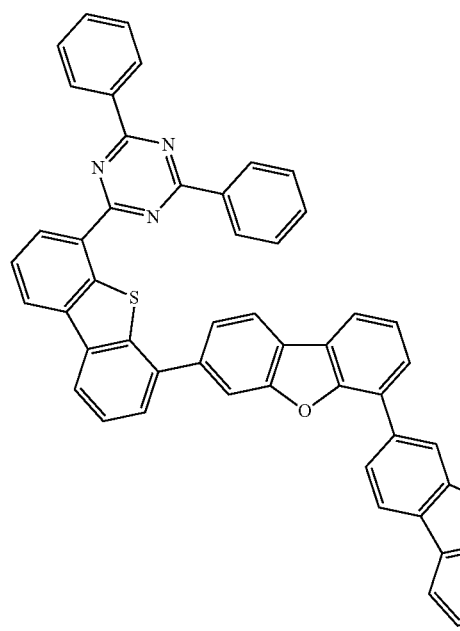
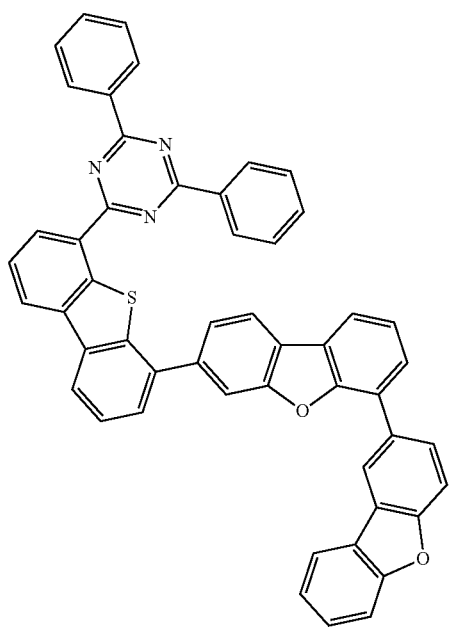

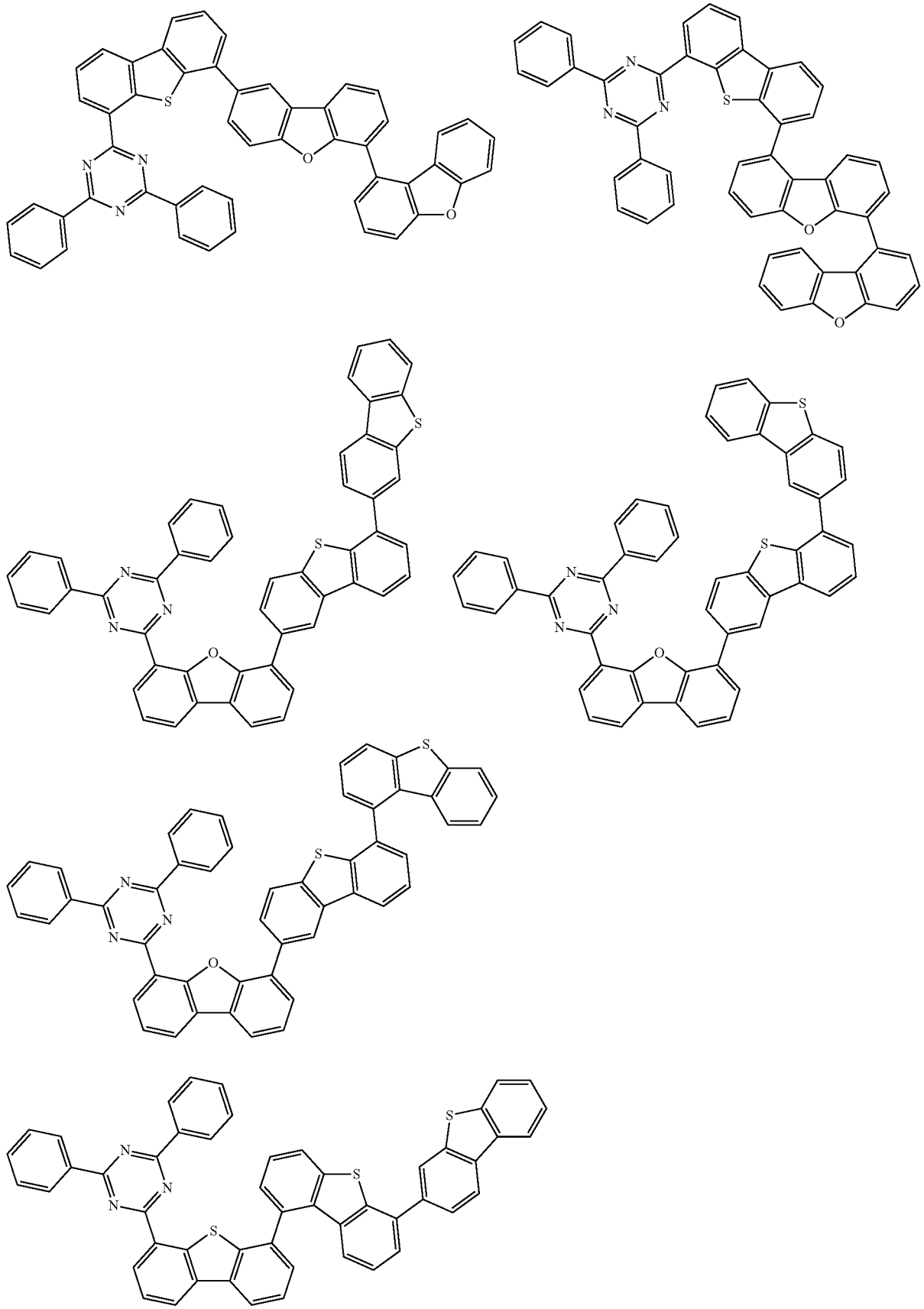

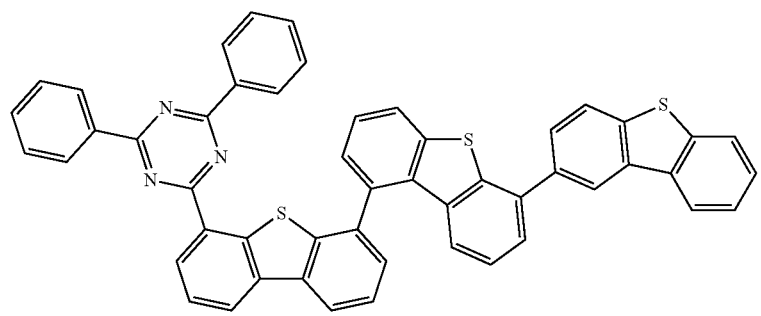
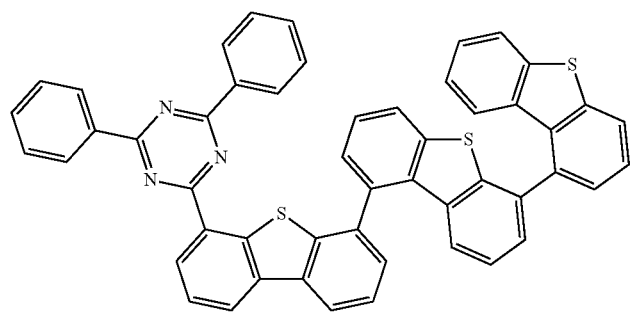
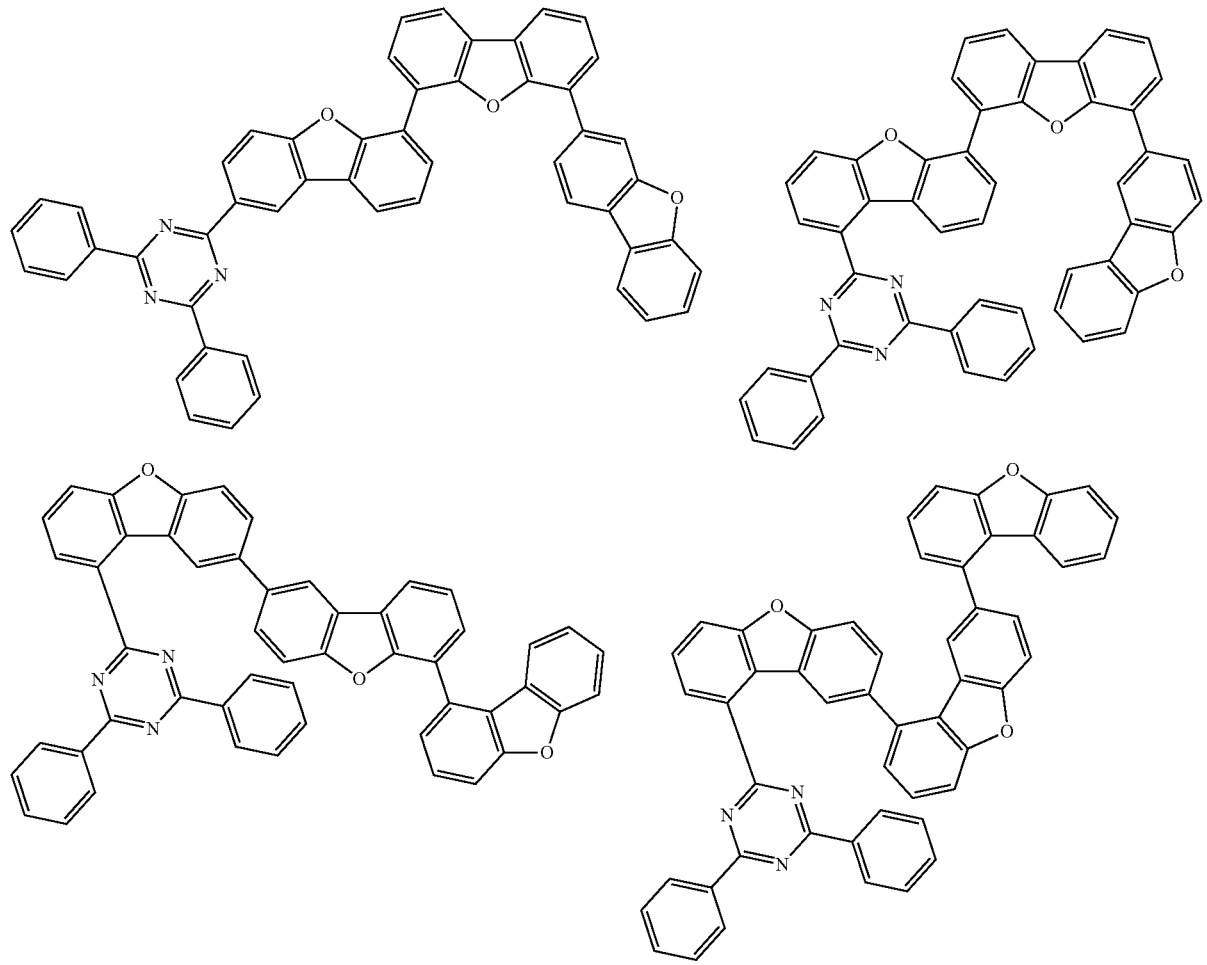

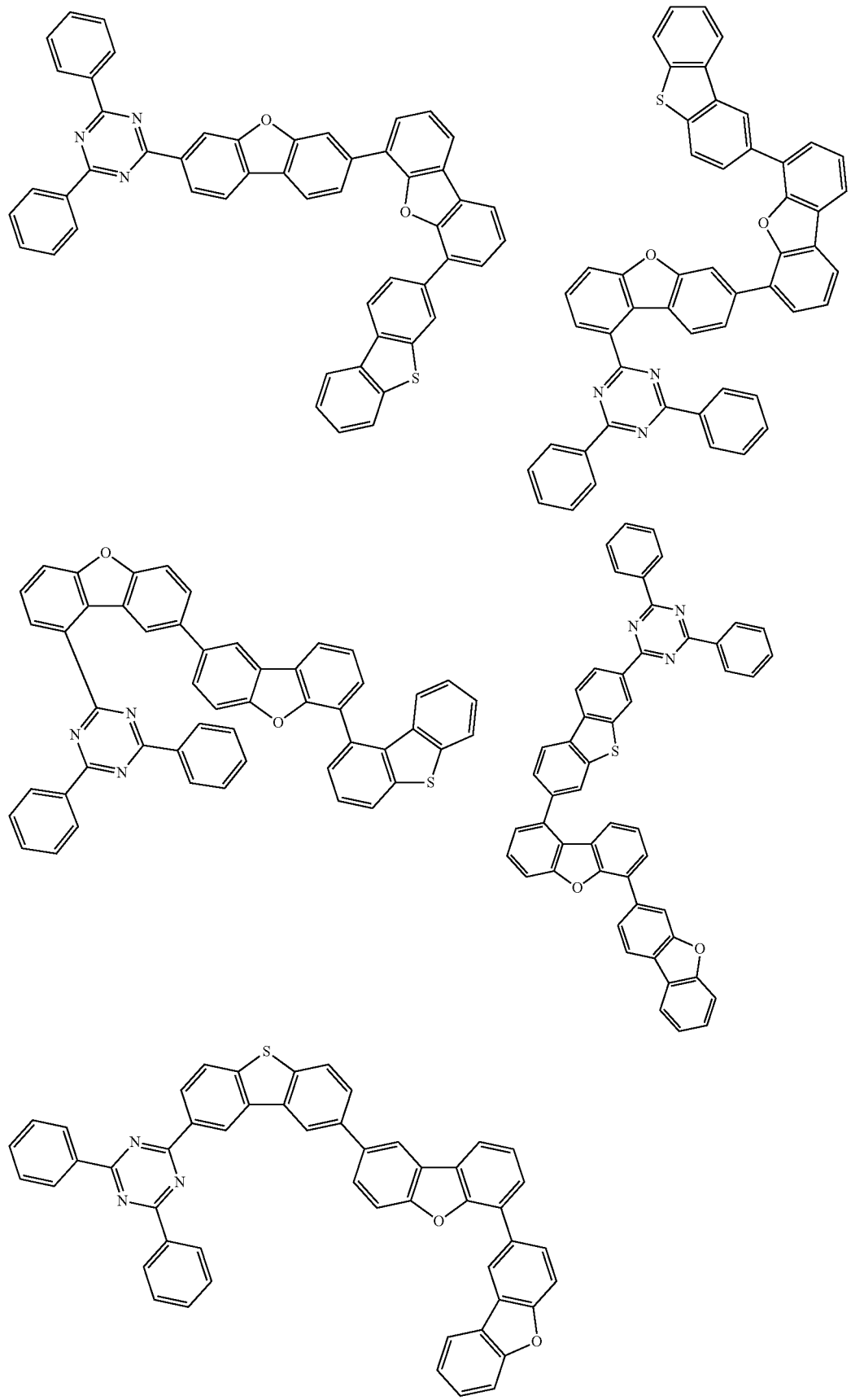

-continued
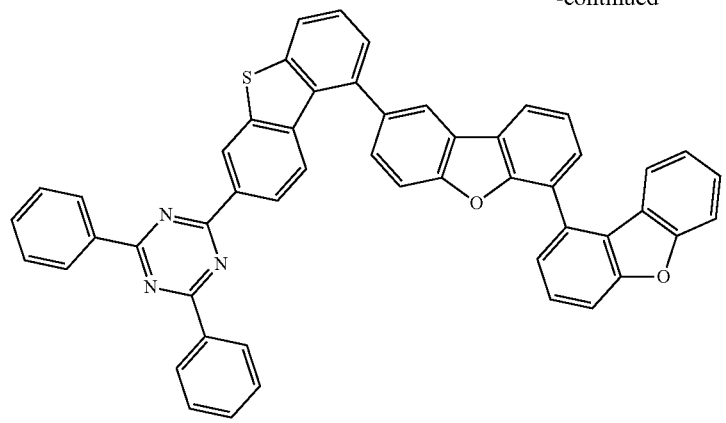
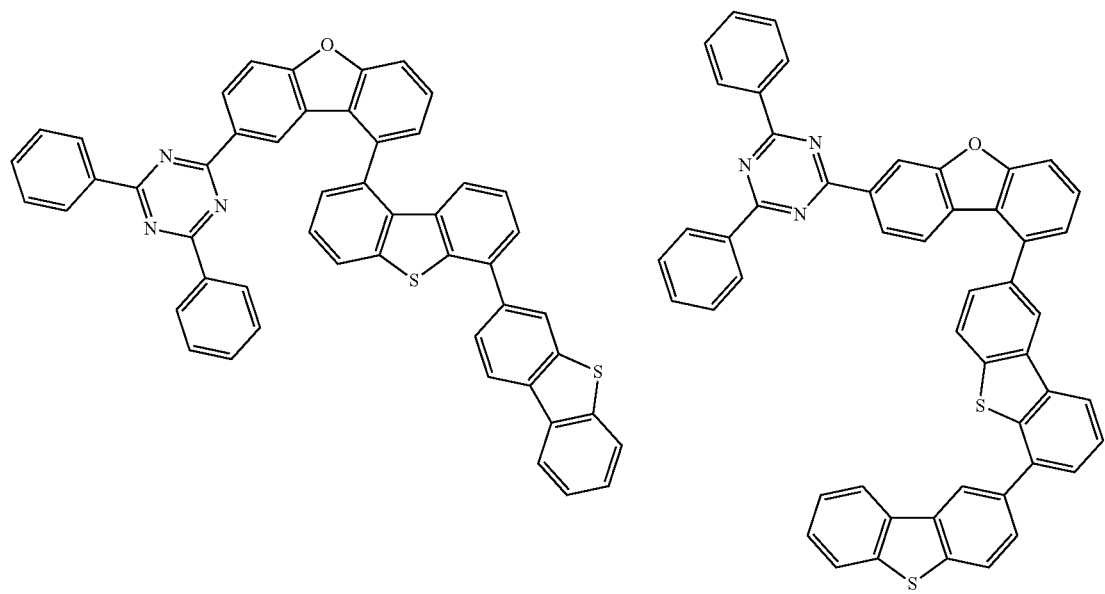
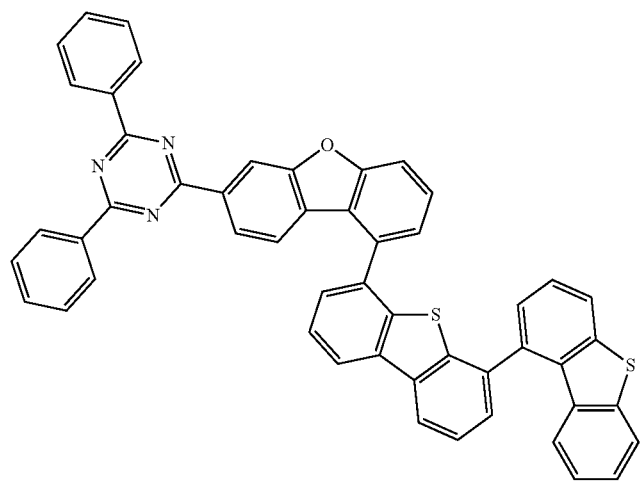

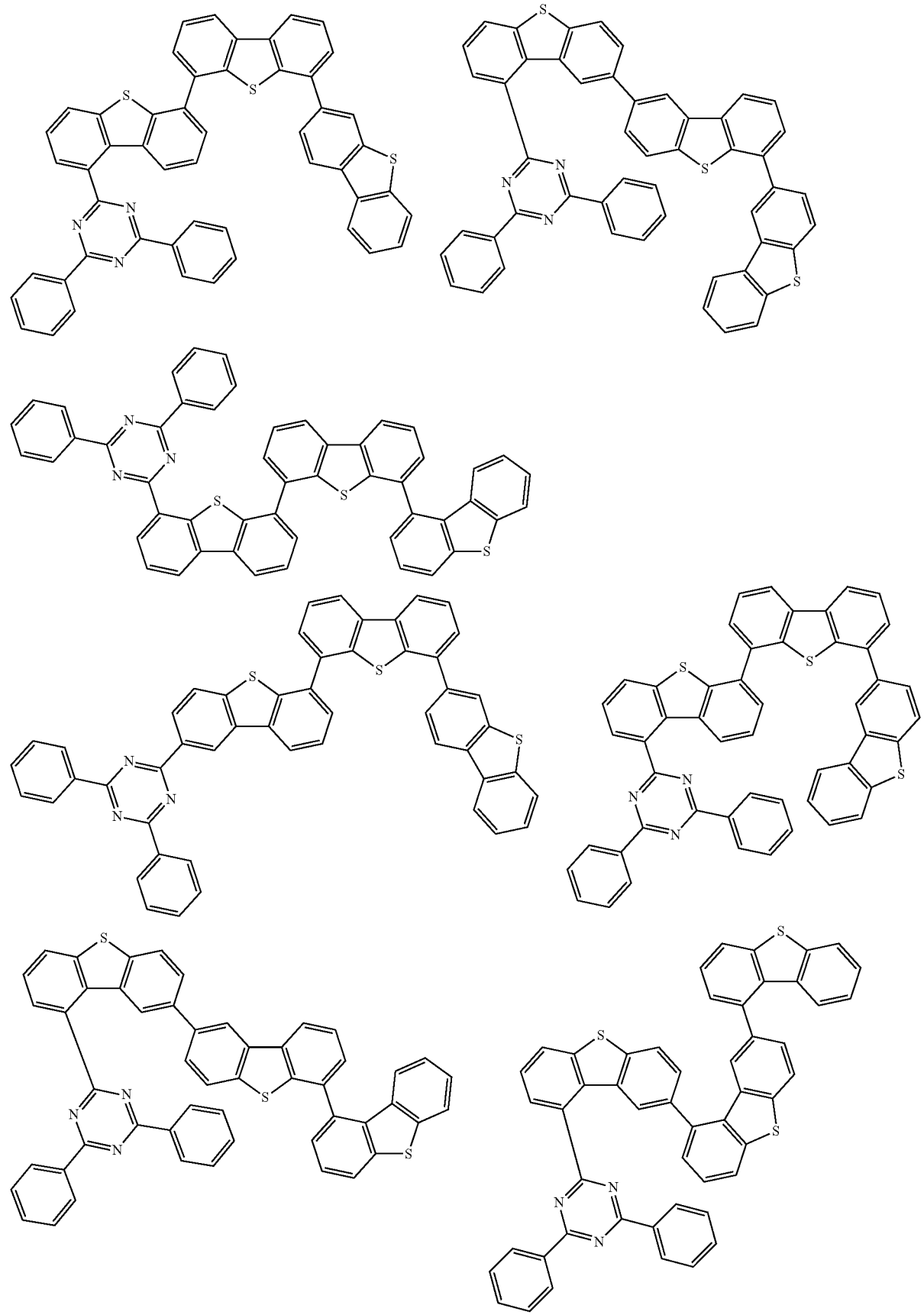

-continued
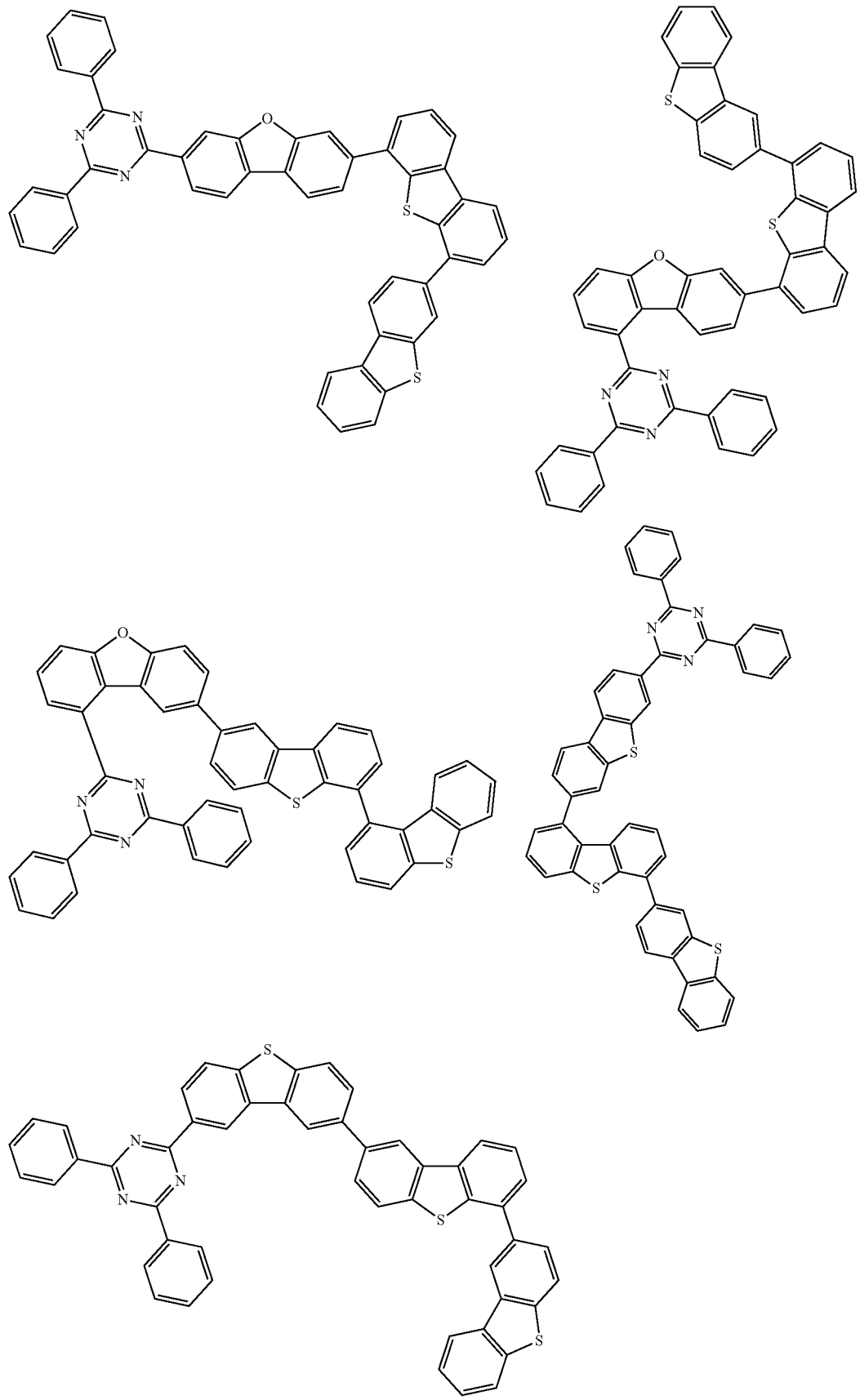

-continued
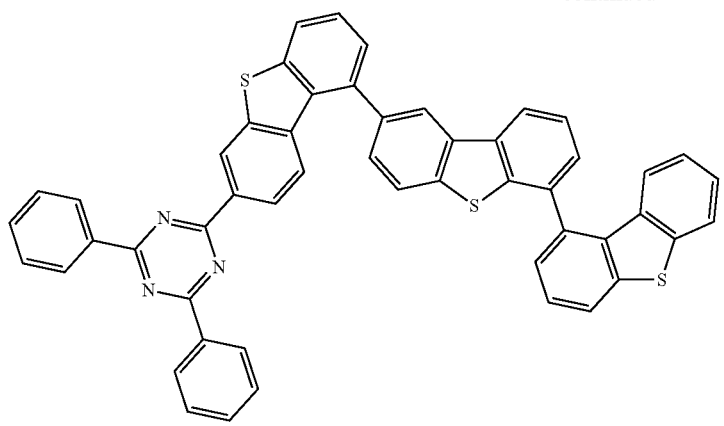

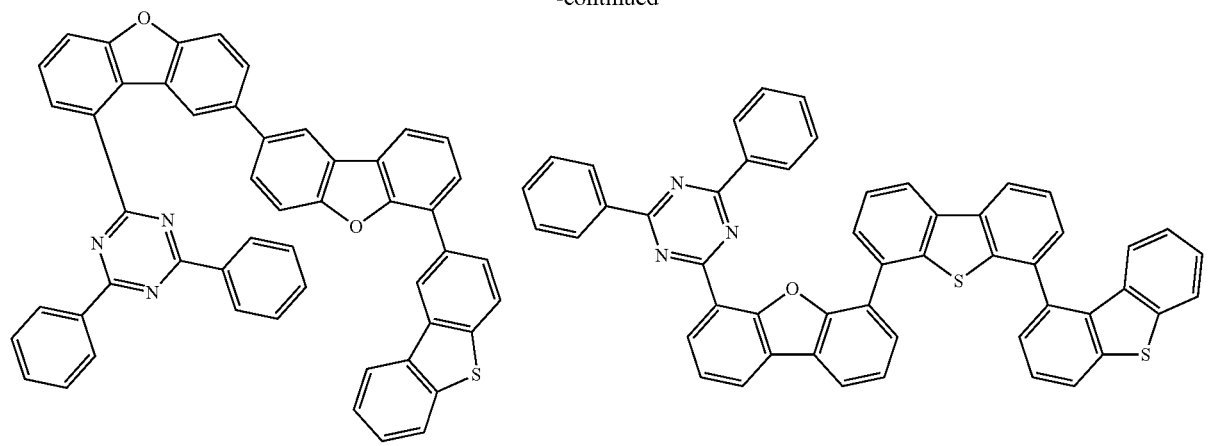
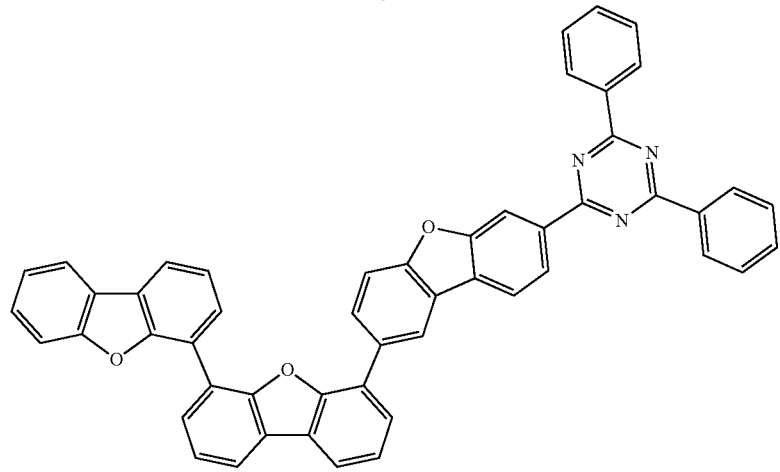
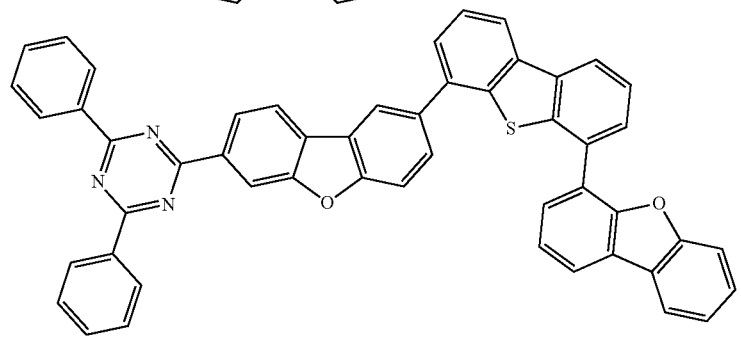
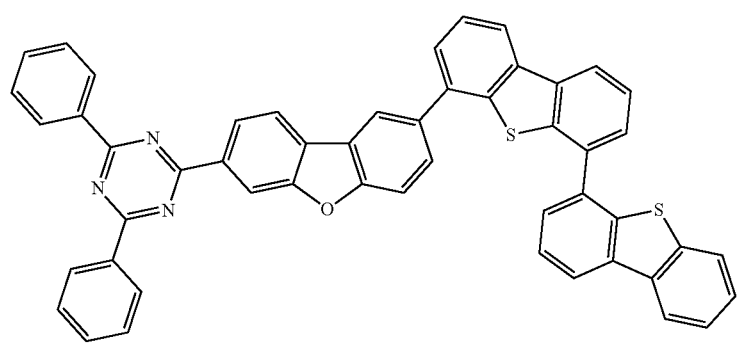

The compound of Chemical Formula 1 may be prepared by a preparation method as shown in Reaction Scheme 1 below. The above preparation method may be further embodied in Preparation Examples described hereinafter.

Reaction Scheme 1

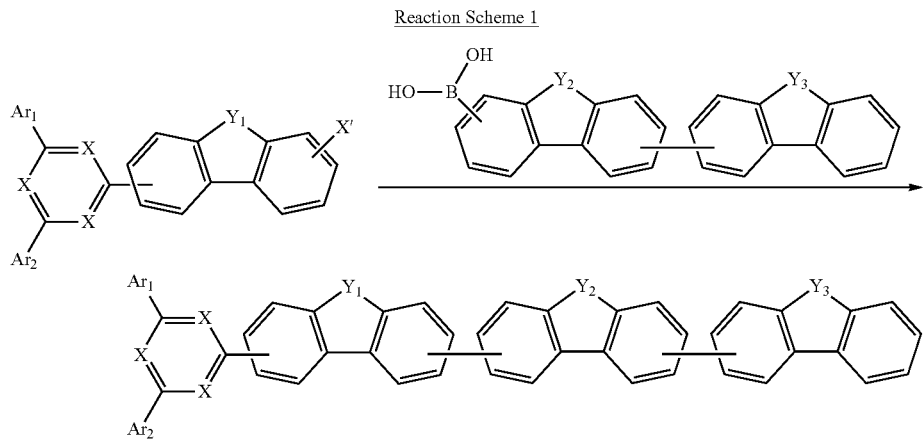

In Reaction Scheme 1, the remaining definitions excluding X 'are as defined above, and X' is halogen and more preferably bromo or chloro. The above-mentioned reaction is a Suzuki coupling reaction, which is preferably carried out in the presence of a palladium catalyst and a base, and a reactive group for the Suzuki coupling reaction can be modified as known in the art. The above preparation method may be further embodied in the Preparation Examples described hereinafter.

Another embodiment of the invention provides an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

The organic material layer of the organic light emitting device of the present invention may have a single-layer structure, or it may have a multilayered structure in which two or more organic material layers are stacked. For example, the organic light emitting device of the present invention may have a structure comprising a hole injection layer, a hole transport layer, an electron blocking layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, an electron blocking layer, or a layer for simultaneously performing hole injection and transport, wherein the hole injection layer, the hole transport layer, the electron blocking layer, or the layer for simultaneously performing hole injection and transport include the compound of Chemical Formula 1.

Further, the organic material layer may include a light emitting layer, wherein the light emitting layer includes the compound of Chemical Formula 1.

Further, the organic material layer may include an electron transport layer, an electron injection layer, and a layer for simultaneously performing electron transport and injection, wherein the electron transport layer, the electron injection layer, and the layer for simultaneously performing electron transport and injection includes the compound of Chemical Formula 1.

In addition, the organic material layer includes a light emitting layer and an electron transport layer, wherein the electron transport layer may include a compound of Chemical Formula 1.

Further, the organic light emitting device according to the present invention may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 may be included in the light emitting layer.

FIG. 2 shows an example of an organic light emitting device comprising a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound of Chemical Formula 1 may be included in one or more layers of the hole injection layer, the hole transport layer, the electron blocking layer, the light emitting layer, the electron transport layer, and the electron injection layer.

Specifically, the organic material layer may include a light emitting layer, wherein the light emitting layer may include two or more host materials.

In this case, the two or more host materials may include a compound of Chemical Formula 1.

The organic light emitting device according to the present invention may be manufactured by materials and methods known in the art, except that one or more layers of the organic material layers include the compound of Chemical Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound of Chemical Formula 1 may be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport material is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including Alq₃; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side emission type, or a double side emission type according to the used material.

In addition, the compound of Chemical Formula 1 may be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only and are not intended to limit the scope of the present invention.

Preparation Example 1: Preparation of Intermediate A-2 a) Preparation of Intermediate A-1

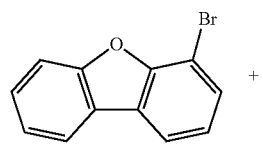

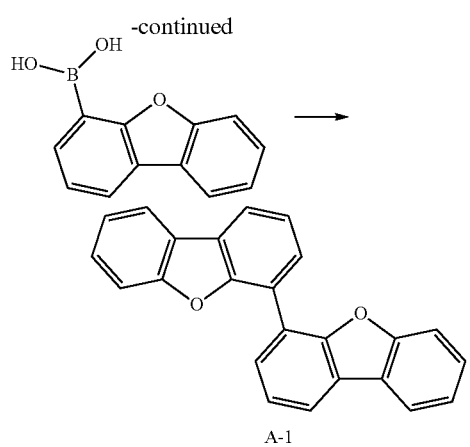

4-Bromodibenzo[b,d]furan (50 g, 122.0 mmol) and dibenzo[b,d]furan-4-ylboronic acid (25.9 g, 122.0 mmol) were dissolved in 500 ml of tetrahydrofuran (THF). 2M calcium carbonate (K₂CO₃) solution (183 mL) and tetrakis(triphenylphosphine)palladium(0) [Pd(PPh₃)₄] (4.2 g, 3 mol %) were added thereto and the mixture was refluxed for 12 hours. After completion of the reaction, the reaction mixture was cooled to room temperature and was extracted three times with water and toluene. The toluene layer was separated, then dried over magnesium sulfate, filtered, and the filtrate was distilled under reduced pressure. The resulting mixture was recrystallized once with chloroform and ethyl acetate to give Intermediate A-1 (27.3 g, yield: 67%; MS: [M+H]⁺=335).

b) Preparation of Intermediate A-2

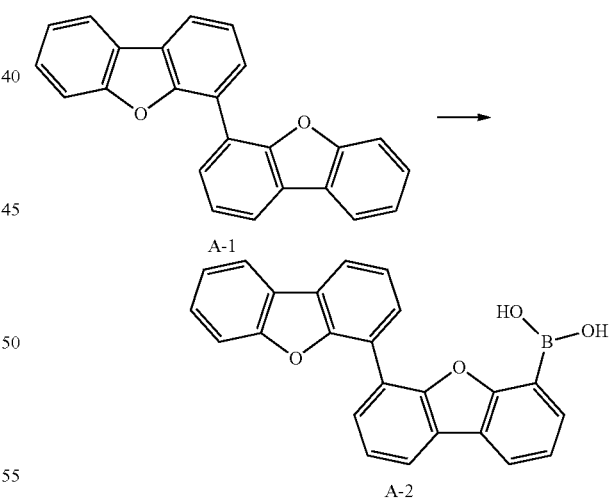

After Intermediate A-1 (25.0 g, 74.8 mmol) was dissolved in tetrahydrofuran (250 ml), the temperature was lowered to −78° C., and 2.5M n-butyllithium (t-BuLi) (35.9 ml, 89.8 mmol) was slowly added thereto. After stirring for 1 hour at the same temperature, triisopropylborate (B(OiPr)₃) (21.1 ml, 112.2 mmol) was added thereto and then stirred for 3 hours while gradually raising the temperature to room temperature. 2N aqueous hydrochloric acid solution (100 ml) was added to the reaction mixture and stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate A-2 (23.8 g, yield: 84%; MS:[M+H]⁺=379).

Preparation Example 2: Preparation of Intermediate B-2 a) Preparation of Intermediate B-1

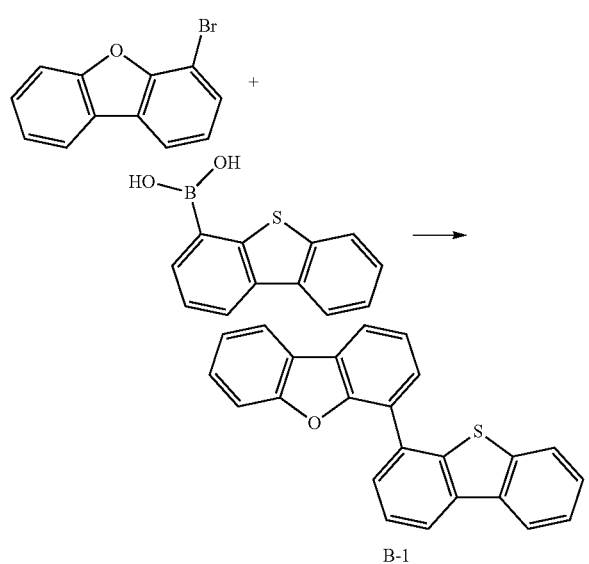

B-1

4-Bromodibenzo[b, d]furan (50 g, 122.0 mmol) and dibenzo[b,d]thiophen-4-ylboronic acid (27.8 g, 122.0 mmol) were dissolved in 500 ml of tetrahydrofuran (THF). 2M calcium carbonate ($K_2CO_3$) solution (183 mL) and tetrakis (triphenylphosphine)palladium(0) [Pd(PPh₃)₄] (4.2 g, 3 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized once with chloroform and ethyl acetate to give Intermediate B-1 (34.1 g, yield: 71%; MS:[M+H]⁺=352).

b) Preparation of Intermediate B-2

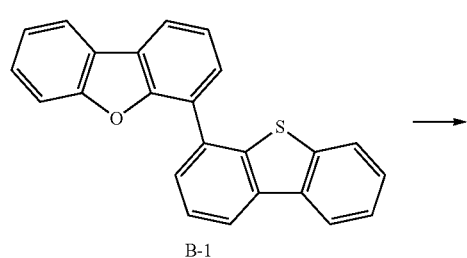

B-1

-continued

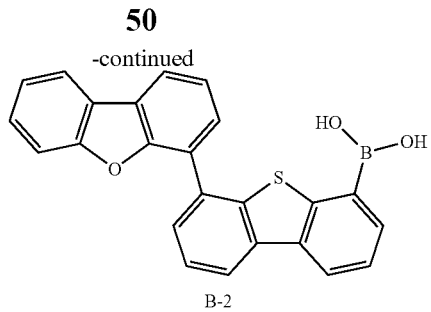

B-2

After Intermediate B-1 (25.0 g, 74.8 mmol) was dissolved in tetrahydrofuran (250 ml), the temperature was lowered to −78° C., and 2.5M n-butyllithium (t-BuLi) (35.9 ml, 89.8 mmol) was slowly added thereto. After stirring for 1 hour at the same temperature, triisopropylborate (B(OiPr)₃) (21.1 ml, 112.2 mmol) was added and then stirred for 3 hours while gradually raising the temperature to room temperature. 2N aqueous hydrochloric acid solution (100 ml) was added to the reaction mixture and stirred for 1.5 hours at room temperature. The produced precipitate was filtered, washed sequentially with water and ethyl ether, and dried under vacuum. After drying, it was dispersed in ethyl ether, stirred for 2 hours, then filtered and dried to prepare Intermediate B-2 (24.5 g, yield: 87%; MS:[M+H]⁺=395).

Preparation Example 3: Preparation of Intermediate C-2

1) Preparation of Intermediate C-1

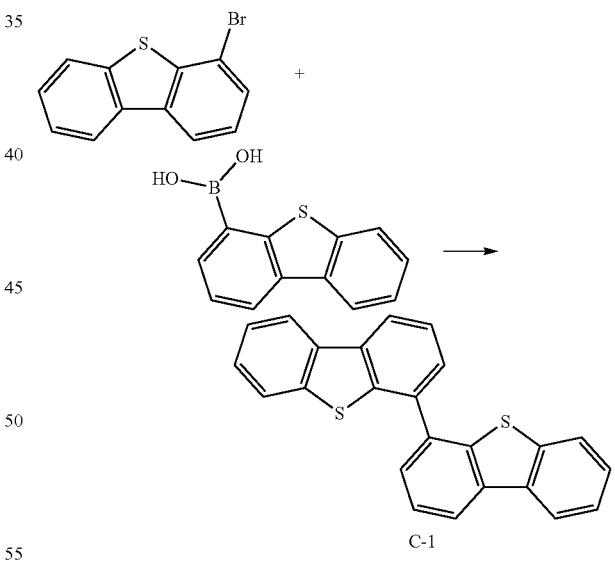

C-1

4-Bromodibenzo[b, d]thiophene (50 g, 114.5 mmol) and dibenzo[b,d]thiophen-4-ylboronic acid (26.1 g, 114.5 mmol) were dissolved in 500 ml of tetrahydrofuran (THF). 2M calcium carbonate ($K_2CO_3$) solution (172 mL) and tetrakis (triphenylphosphine)palladium(0) [Pd(PPh₃)₄] (4.0 g, 3 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized once with chloroform and ethyl acetate to give Intermediate C-1 (28.9 g, yield: 69%; MS:[M+H]⁺=367).

2) Preparation of Intermediate C-2

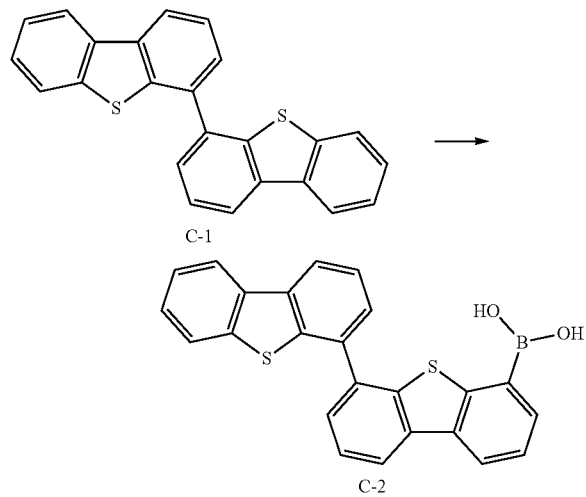

After Intermediate C-1 (25.0 g, 68.3 mmol) was dissolved in tetrahydrofuran (250 ml), the temperature was lowered to −78° C., and 2.5M n-butyllithium (t-BuLi) (32.8 ml, 82.0 mmol) was slowly added thereto. After stirring for 1 hour at the same temperature, triisopropylborate (B(OiPr)₃) (23.6 ml, 102.5 mmol) was added thereto and then stirred for 3 hours while gradually raising the temperature to room temperature. 2N aqueous hydrochloric acid solution (100 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate C-2 (21.5 g, yield: 77%; MS:[M+H]⁺=411).

Preparation Example 4: Preparation of Intermediate D-2

1) Preparation of Intermediate D-1

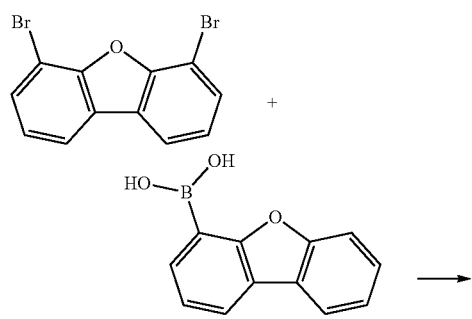

-continued

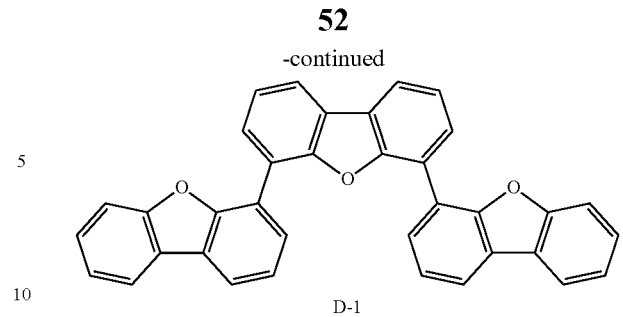

4,6-Dibromodibenzo[b,d]furan (50 g, 154.4 mmol) and dibenzo[b,d]furan-4-ylboronic acid (68.7 g, 324.4 mmol) were dissolved in 500 ml of tetrahydrofuran (THF). 2M calcium carbonate (K₂CO₃) solution (463 mL) and tetrakis (triphenylphosphine)palladium(0) [Pd(PPh₃)₄] (10.7 g, 3 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized once with chloroform and ethyl acetate to give Intermediate D-1 (56.4 g, yield: 73%; MS: [M+H]⁺=501).

2) Preparation of Intermediate D-2

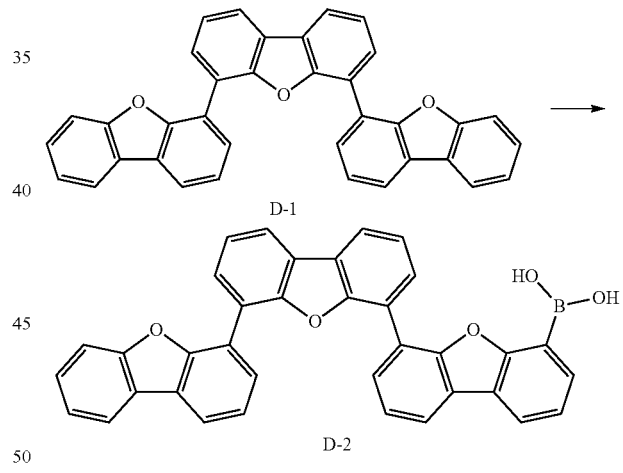

After Intermediate D-1 (25.0 g, 50.0 mmol) was dissolved in tetrahydrofuran (250 ml), the temperature was lowered to −78° C., and 2.5M n-butyllithium (t-BuLi) (24.0 ml, 60.0 mmol) was slowly added thereto. After stirring for 1 hour at the same temperature, triisopropylborate (B(OiPr)₃) (17.3 ml, 75.0 mmol) was added thereto and then stirred for 3 hours while gradually raising the temperature to room temperature. 2N aqueous hydrochloric acid solution (100 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate D-2 (16.6 g, yield: 61%; MS:[M+H]⁺=545).

Preparation Example 5: Preparation of Intermediate E-2

1) Preparation of Intermediate E-1

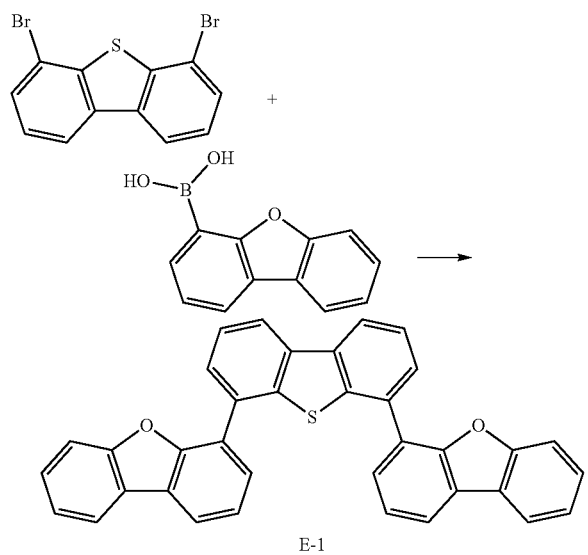

E-1

4,6-Dibromodibenzo[b,d]thiophene (50 g, 147.1 mmol) and dibenzo[b, d]furan-4-ylboronic acid (65.5 g, 309.0 mmol) were dissolved in 500 ml of tetrahydrofuran (THF). 2M calcium carbonate ($K_2CO_3$) solution (441 mL) and tetrakis(triphenylphosphine)palladium(0) [Pd(PPh$_3$)$_4$] (10.2 g, 3 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized once with chloroform and ethyl acetate to give Intermediate E-1 (46.3 g, yield: 61%; MS: $[M+H]^+$=517).

2) Preparation of Intermediate E-2

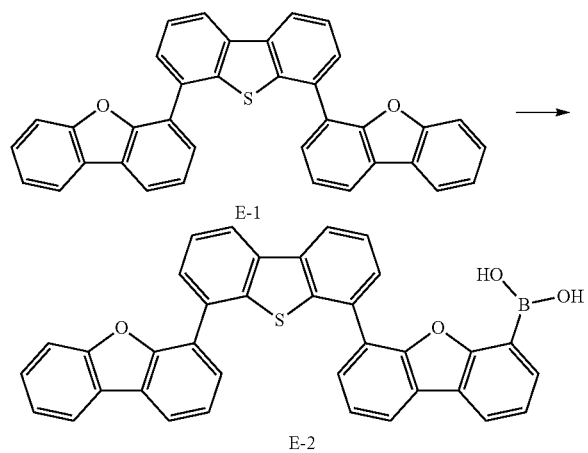

E-2

After Intermediate E-1 (25.0 g, 48.4 mmol) was dissolved in tetrahydrofuran (250 ml), the temperature was lowered to −78° C., and 2.5M n-butyllithium (t-BuLi) (23.3 ml, 58.1 mmol) was slowly added thereto. After stirring for 1 hour at the same temperature, triisopropylborate (B(OiPr)$_3$) (16.8 ml, 72.7 mmol) was added thereto and then stirred for 3 hours while gradually raising the temperature to room temperature. 2N aqueous hydrochloric acid solution (100 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate E-2 (18.7 g, yield: 69%; MS:$[M+H]^+$=561).

Preparation Example 6: Preparation of Intermediate F-2

1) Preparation of Intermediate F-1

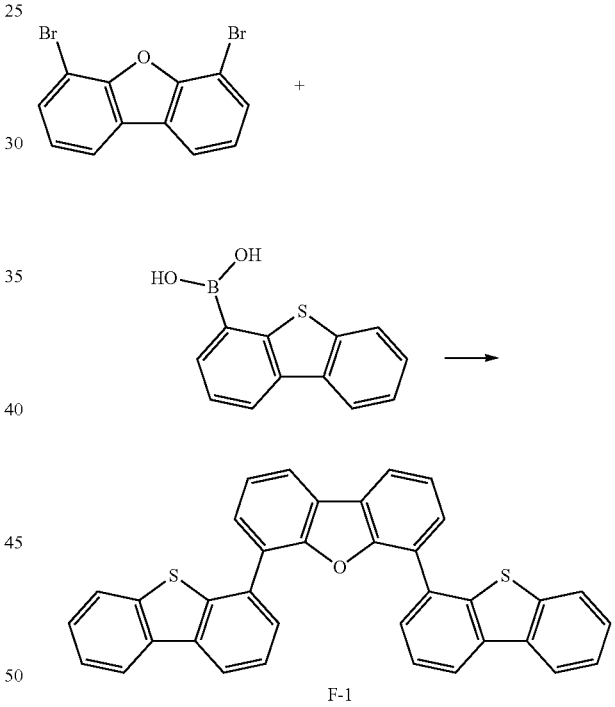

F-1

4,6-Dibromodibenzo[b,d]furan (50 g, 154.4 mmol) and dibenzo[b,d]thiophen-4-ylboronic acid (73.9 g, 324.4 mmol) were dissolved in 500 ml of tetrahydrofuran (THF). 2M calcium carbonate ($K_2CO_3$) solution (463 mL) and tetrakis (triphenylphosphine)palladium(0) [Pd(PPh$_3$)$_4$] (10.7 g, 3 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized once with chloroform and ethyl acetate to give Intermediate F-1 (44.4 g, yield: 50%; MS: $[M+H]^+$=577).

2) Preparation of Intermediate F-2

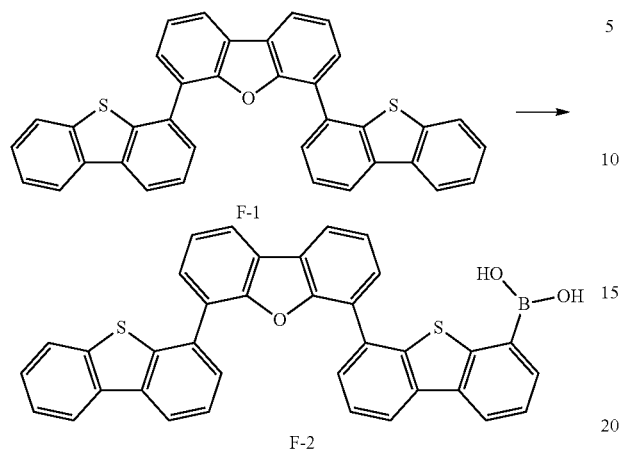

After Intermediate F-1 (25.0 g, 43.4 mmol) was dissolved in tetrahydrofuran (250 ml), the temperature was lowered to −78° C., and 2.5M n-butyllithium (t-BuLi) (20.8 ml, 43.4 mmol) was slowly added thereto. After stirring for 1 hour at the same temperature, triisopropylborate (B(OiPr)$_3$) (15.0 ml, 65.1 mmol) was added thereto and then stirred for 3 hours while gradually raising the temperature to room temperature. 2N aqueous hydrochloric acid solution (100 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate F-2 (19.1 g, yield: 70%; MS:[M+H]$^+$=577).

Preparation Example 7: Preparation of Intermediate G-2

1) Preparation of Intermediate G-1

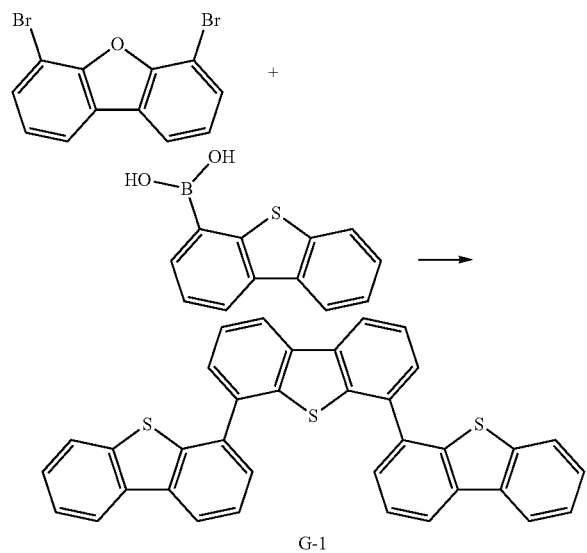

4,6-Dibromodibenzo[b,d]thiophene (50 g, 48.4 mmol) and dibenzo[b,d]thiophen-4-ylboronic acid (70.5 g, 309.0 mmol) were dissolved in 500 ml of tetrahydrofuran (THF). 2M calcium carbonate (441 mL) and (K$_2$CO$_3$) solution tetrakis(triphenylphosphine)palladium(0) [Pd(PPh$_3$)$_4$] (10.2 g, 3 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized once with chloroform and ethyl acetate to give Intermediate G-1 (48.4 g, yield: 60%; MS: [M+H]$^+$=549).

2) Preparation of Intermediate G-2

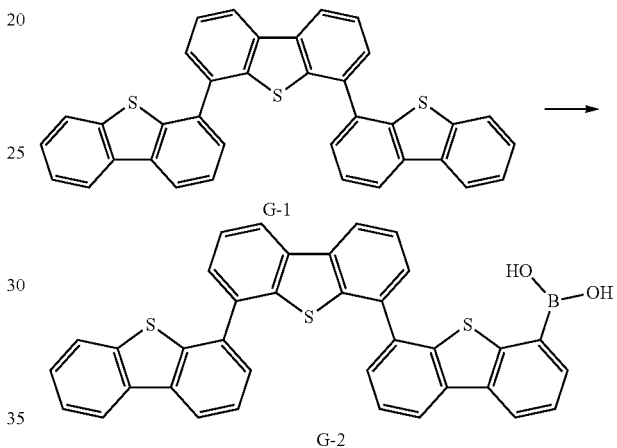

After Intermediate G-1 (25.0 g, 45.6 mmol) was dissolved in tetrahydrofuran (250 ml), the temperature was lowered to −78° C., and 2.5M n-butyllithium (t-BuLi) (21.9 ml, 45.6 mmol) was slowly added thereto. After stirring for 1 hour at the same temperature, triisopropylborate (B(OiPr)$_3$) (15.8 ml, 68.4 mmol) was added thereto and then stirred for 3 hours while gradually raising the temperature to room temperature. 2N aqueous hydrochloric acid solution (100 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate G-2 (15.9 g, yield: 59%; MS:[M+H]$^+$=593).

Preparation Example 8: Preparation of Intermediate P-5 a) Preparation of Intermediate P-1

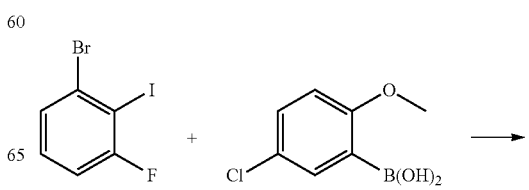

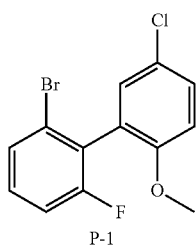

1-Bromo-3-fluoro-2-iodobenzene (100 g, 333.5 mmol) and (5-chloro-2-methoxyphenyl)boronic acid (62.2 g, 333.5 mmol) were dissolved in 800 ml of tetrahydrofuran (THF). 2M calcium carbonate ($K_2CO_3$) solution (500 mL) and tetrakis(triphenylphosphine)palladium(0) [Pd(PPh$_3$)$_4$] (7.7 g, 6.7 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized three times with chloroform and ethyl acetate to give Intermediate P-1 (53.7 g, yield: 51%; MS:[M+H]$^+$=314).

b) Preparation of Intermediate P-2

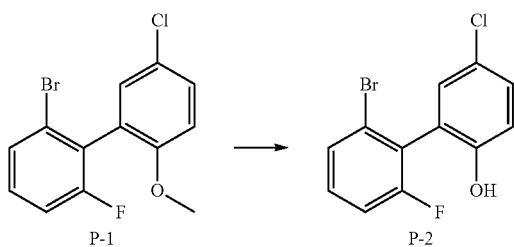

Intermediate P-1 (50.0 g, 158.5 mmol) was dissolved in dichloromethane (600 ml) and then cooled to 0° C. Boron tribromide (15.8 ml, 166.4 mmol) was slowly added dropwise thereto and then stirred for 12 hours. After completion of the reaction, the reaction mixture was washed three times with water, dried over magnesium sulfate and filtered, the filtrate was distilled under reduced pressure and purified by column chromatography to give Intermediate P-2 (47.4 g, yield: 99%; MS:[M+H]$^+$=300).

c) Preparation of Intermediate P-3

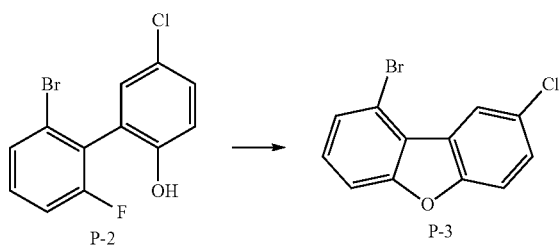

Intermediate P-2 (40.0 g, 132.7 mmol) was dissolved in distilled dimethylformamide (DMF) (400 ml). It was cooled to 0° C. and sodium hydride (3.5 g, 145.9 mmol) was slowly added dropwise thereto. After stirring for 20 minutes, the mixture was stirred at 100° C. for 1 hour. After completion of the reaction, the reaction mixture was cooled to room temperature, and 100 ml of ethanol was slowly added thereto. The above mixture was distilled under reduced pressure, and the resulting mixture was recrystallized from chloroform and ethyl acetate to obtain Intermediate P-3 (30.3 g, yield: 81%; MS:[M+H]$^+$=280).

d) Preparation of Intermediate P-4

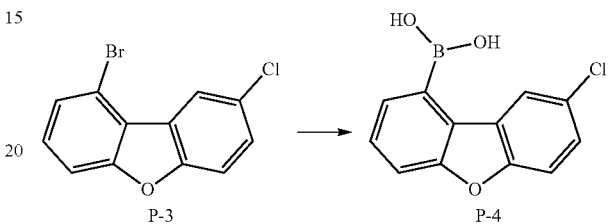

After Intermediate P-3 (30.0 g, 106.6 mmol) was dissolved in dichloromethane (300 ml), the temperature was lowered to −78° C., and 1.7M tert-butyllithium (t-BuLi) (62.7 ml, 106.6 mmol) was slowly added thereto. After stirring for 1 hour at the same temperature, triisopropylborate (B(OiPr)$_3$) (28.3 ml, 213.1 mmol) was added thereto and then stirred for 3 hours while gradually raising the temperature to room temperature. 2N aqueous hydrochloric acid solution (200 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate P-4 (24.4 g, yield: 93%; MS:[M+H]$^+$=247).

e) Preparation of Intermediate P-5

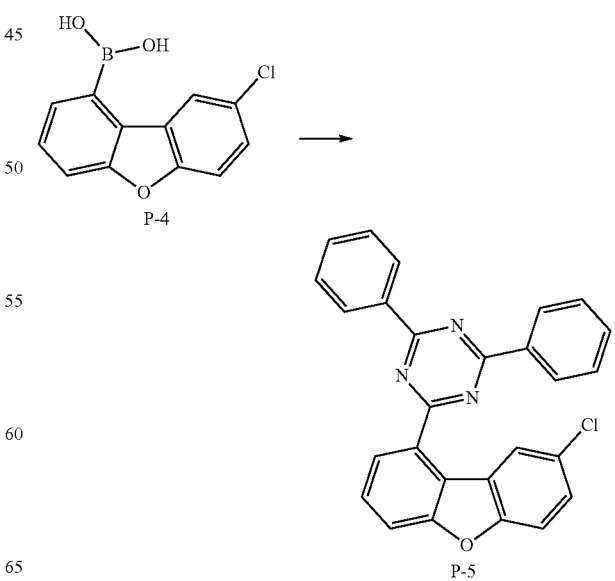

After Intermediate P-4 (20.0 g, 81.2 mmol) and 2-chloro-4,6-diphenyl-1,3,5-triazine (21.8 g, 81.2 mmol) were dispersed in tetrahydrofuran (250 ml), 2M aqueous potassium carbonate solution (aq. K$_2$CO$_3$) (33.6 ml, 243.5 mmol) was added and tetrakistriphenylphosphinopalladium [Pd(PPh$_3$)$_4$] (1.9 g, 2 mol %) was added. The mixture was then stirred and refluxed for 4 hours. The temperature was lowered to room temperature and the produced solid was filtered. The filtered solid was recrystallized from tetrahydrofuran and ethyl acetate, filtered and then dried to prepare Intermediate P-5 (32.4 g, yield: 92%; MS:[M+H]$^+$=434).

Preparation Example 9: Preparation of Intermediate Q-5 a) Preparation of Intermediate Q-1

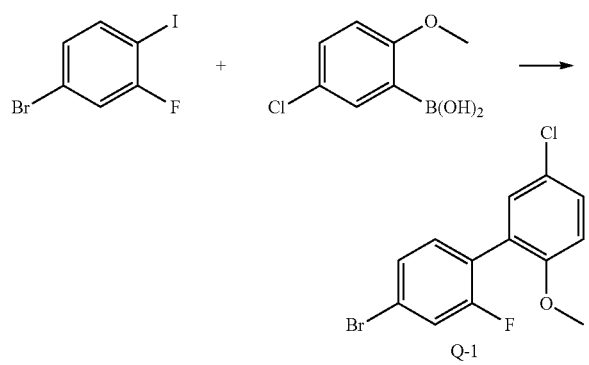

1-Bromo-3-fluoro-4-iodobenzene (50 g, 166.6 mmol) and 5-chloro-2-methoxyphenyl)boronic acid (31.1 g, 166.6 mmol) were dissolved in 800 ml of tetrahydrofuran (THF). 2M sodium carbonate (Na$_2$CO$_3$) solution (250 mL) and tetrakis(triphenylphosphine)palladium(0) [Pd(PPh$_3$)$_4$] (3.8 g, 3 mol %) were added thereto and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized three times with chloroform and ethyl acetate to give Intermediate Q-1 (27.5 g, yield: 51%; MS:[M+H]$^+$=314).

b) Preparation of Intermediate Q-2

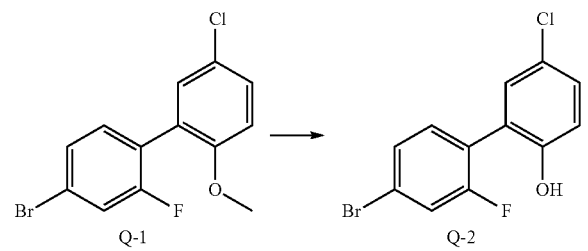

Intermediate Q-1 (25.0 g, 150 mmol) was dissolved in dichloromethane (300 ml) and then cooled to 0° C. Boron tribromide (7.9 ml, 83.2 mmol) was slowly added dropwise thereto and then stirred for 12 hours. After completion of the reaction, the reaction mixture was washed three times with water, dried over magnesium sulfate and filtered, the filtrate was distilled under reduced pressure and purified by column chromatography to give Intermediate Q-2 (23.7 g, yield: 99%; MS:[M+H]$^+$=300).

c) Preparation of Intermediate Q-3

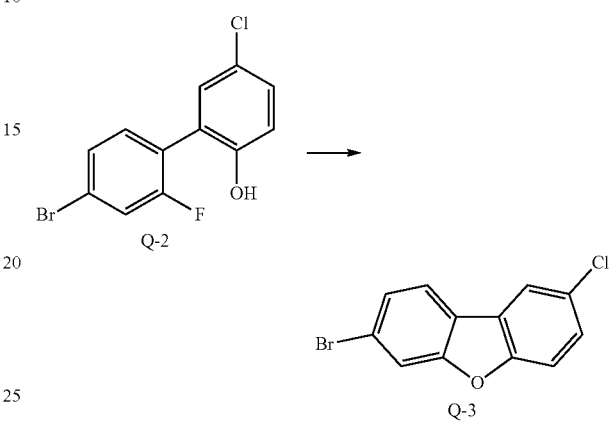

Intermediate Q-2 (20.0 g, 66.4 mmol) was dissolved in distilled dimethylformamide (DMF) (200 ml). It was cooled to 0° C. and sodium hydride (1.8 g, 72.9 mmol) was slowly added dropwise thereto. After stirring for 20 minutes, the mixture was stirred at 100° C. for 1 hour. After completion of the reaction, the reaction mixture was cooled to room temperature, and 100 ml of ethanol was slowly added thereto. The above mixture was distilled under reduced pressure, and the resulting mixture was recrystallized from chloroform and ethyl acetate to give Intermediate Q-3 (15.2 g, yield: 81%; MS:[M+H]$^+$=280).

d) Preparation of Intermediate Q-4

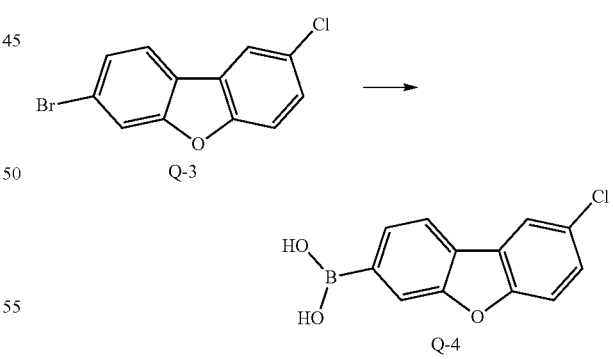

After Intermediate Q-3 (15.0 g, 53.3 mmol) was dissolved in tetrahydrofuran (150 ml), the temperature was lowered to −78° C., and 1.7M tert-butyllithium (t-BuLi) (31.8 ml, 53.3 mmol) was slowly added thereto. After stirring for 1 hour at the same temperature, triisopropylborate (B(OiPr)$_3$) (14.2 ml, 107.0 mmol) was added thereto and then stirred for 3 hours while gradually raising the temperature to room temperature. 2N aqueous hydrochloric acid solution (100 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Intermediate Q-4 (12.2 g, yield: 93%; MS:[M+H]$^+$=247).

e) Preparation of Intermediate Q-5

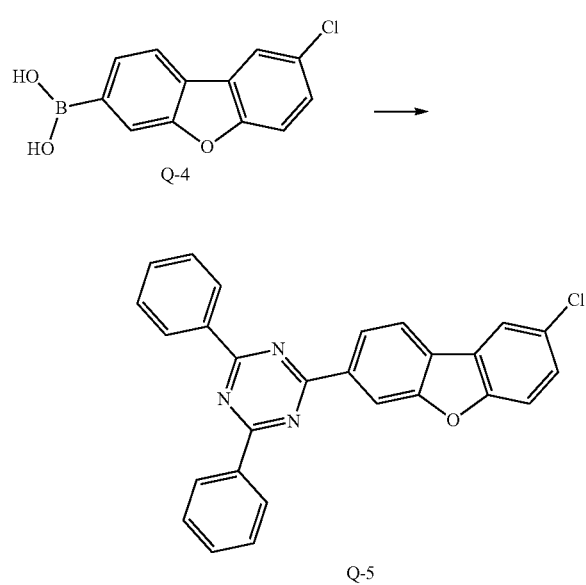

After Intermediate Q-4 (10.0 g, 40.6 mmol) and 2-chloro-4,6-diphenyl-1,3,5-triazine (10.9 g, 40.6 mmol) were dispersed in tetrahydrofuran (150 ml), 2M aqueous potassium carbonate solution (aq. K$_2$CO$_3$) (12 ml, 122 mmol) was added and tetrakistriphenylphosphinopalladium [Pd(PPh$_3$)$_4$] (1.0 g, 2 mol %) was added. The mixture was then stirred and refluxed for 4 hours. The temperature was lowered to room temperature and the produced solid was filtered. The filtered solid was recrystallized from tetrahydrofuran and ethyl acetate, filtered and then dried to prepare Intermediate Q-5 (16.2 g, yield: 92%; MS:[M+H]$^+$=434).

Example 1: Preparation of Compound 1

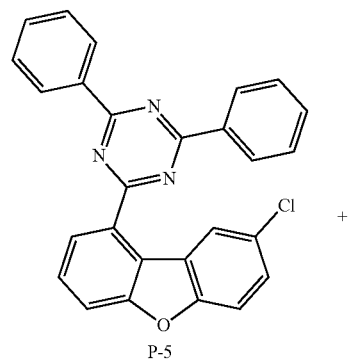

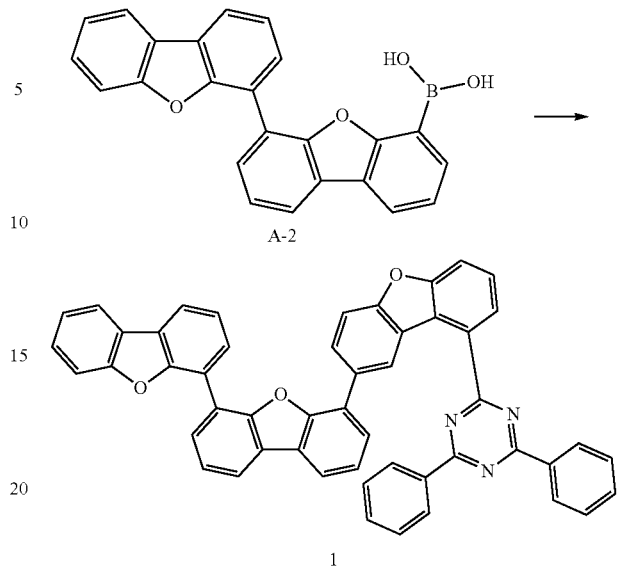

After Intermediate P-5 (15.0 g, 34.6 mmol) and Intermediate A-2 (13.1 g, 34.6 mmol) were dispersed in tetrahydrofuran (150 ml), 2M aqueous potassium carbonate solution (aq. K$_2$CO$_3$) (12 ml, 52 mmol) was added and bis(tri-tert-butylphosphine)palladium [Pd(PPh$_3$)$_4$] (0.5 g, 3 mol %) was added. The mixture was then stirred and refluxed for 4 hours. The temperature was lowered to room temperature and the produced solid was filtered. The filtered solid was recrystallized from tetrahydrofuran and ethyl acetate, filtered and then dried to prepare Compound 1 (9.6 g, yield: 38%; MS:[M+H]$^+$=732).

Example 2: Preparation of Compound 2

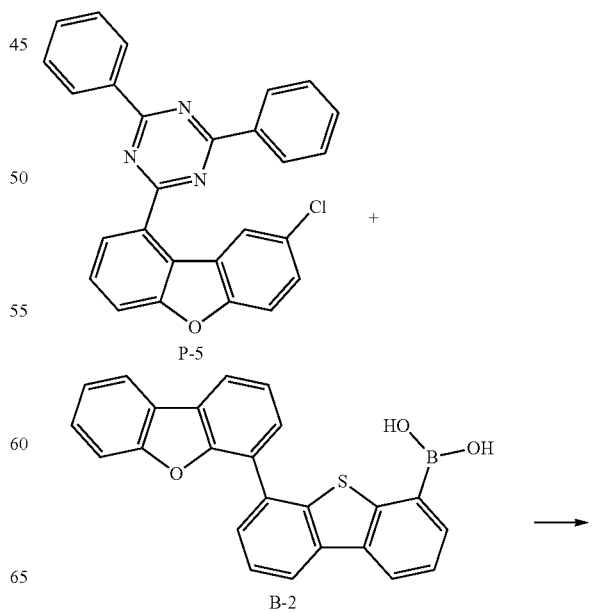

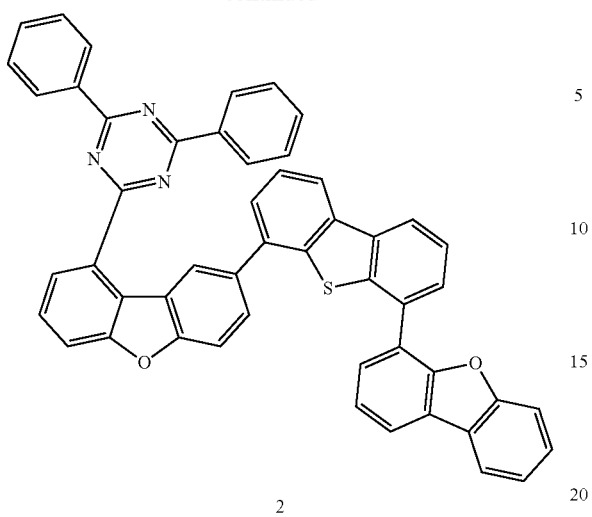

2

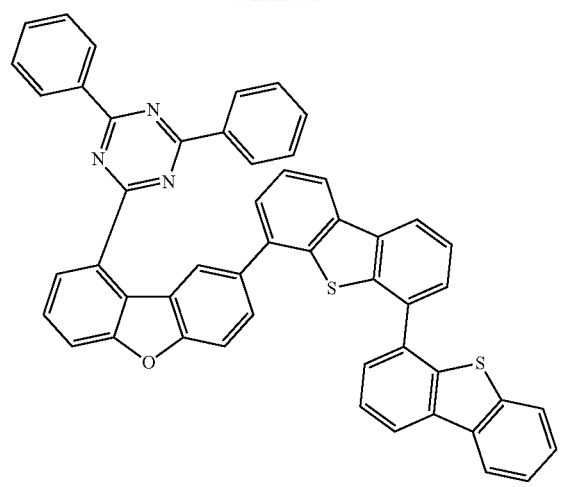

3

Compound 2 (11.4 g, yield: 44%; MS:[M+H]$^+$=748) was prepared in the same manner as in the preparation of Compound 1 of Example 1, except that Intermediate B-2 (13.6 g, 34.6 mmol) was used instead of Intermediate A-2.

Compound 3 (10.6 g, yield: 40%; MS:[M+H]$^+$=764) was prepared in the same manner as in the preparation of Compound 1 of Example 1, except that Intermediate C-2 (14.2 g, 34.6 mmol) was used instead of Intermediate A-2.

Example 3: Preparation of Compound 3

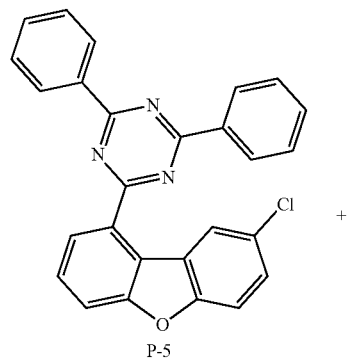

P-5

+

Example 4: Preparation of Compound 4

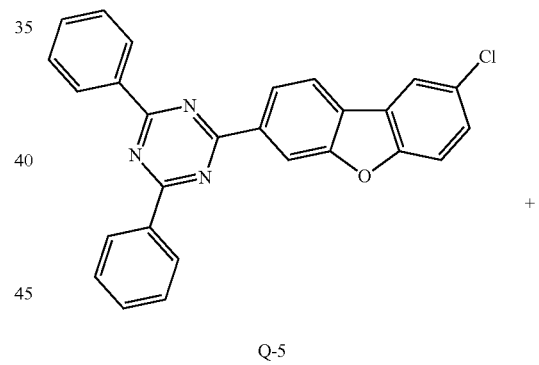

Q-5

+

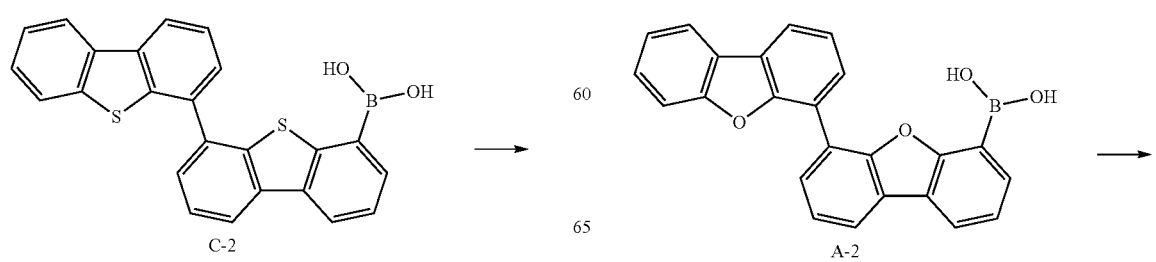

C-2

A-2

-continued

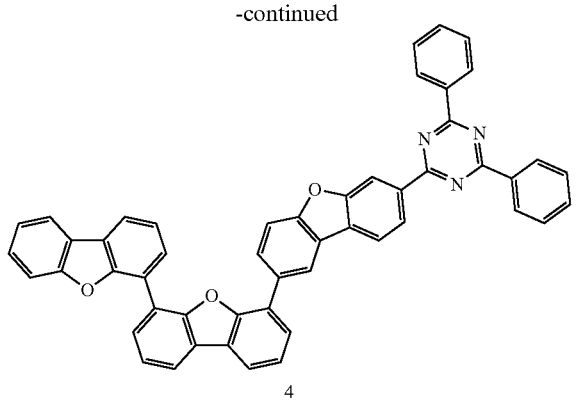

4

After Intermediate Q-5 (15.0 g, 34.6 mmol) and Intermediate A-2 (13.1 g, 34.6 mmol) were dispersed in tetrahydrofuran (150 ml), 2M aqueous potassium carbonate solution (aq. K₂CO₃) (12 ml, 52 mmol) was added and bis(tri-tert-butylphosphine)palladium [Pd(PPh₃)₄] (0.5 g, 3 mol %) was added. The mixture was then stirred and refluxed for 4 hours. The temperature was lowered to room temperature and the produced solid was filtered. The filtered solid was recrystallized from tetrahydrofuran and ethyl acetate, filtered and then dried to prepare Compound 4 (11.1 g, yield: 44%; MS:[M+H]⁺=732).

Example 5: Preparation of Compound 5

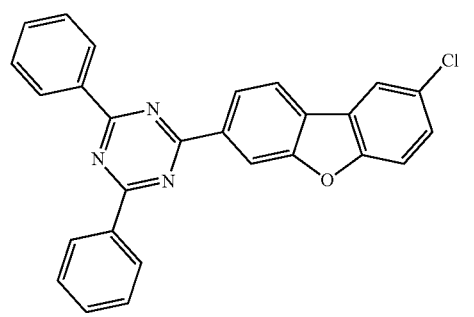

Q-5

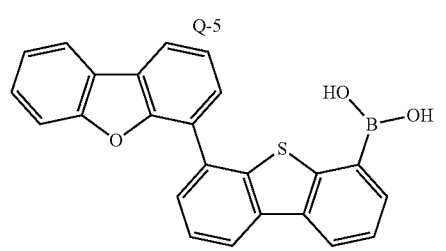

B-2

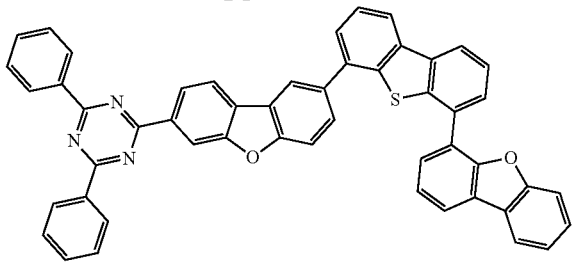

5

Compound 5 (13.2 g, yield: 51%; MS:[M+H]⁺=748) was prepared in the same manner as in the preparation of Compound 4 of Example 4, except that Intermediate B-2 (13.6 g, 34.6 mmol) was used instead of Intermediate A-2.

Example 6: Preparation of Compound 6

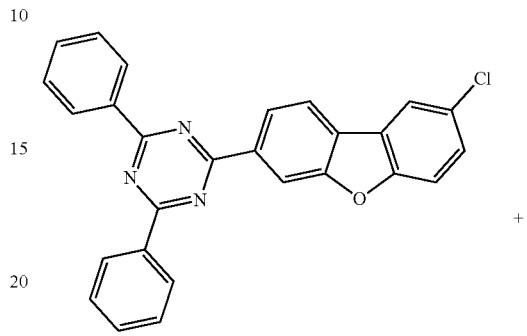

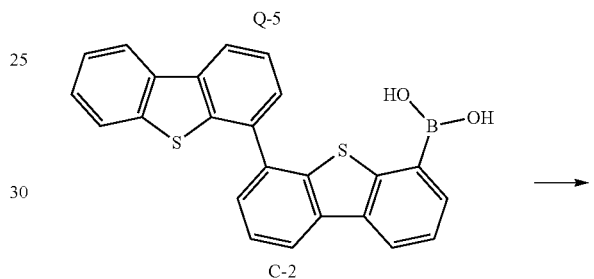

C-2

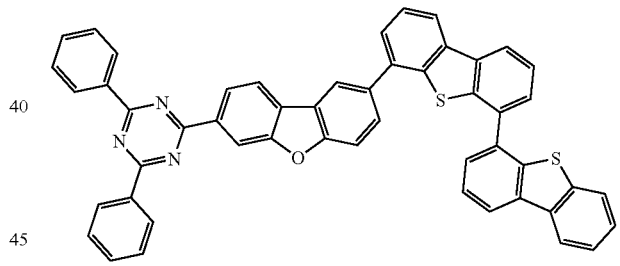

6

Compound 6 (7.1 g, yield: 27%; MS:[M+H]⁺=764) was prepared in the same manner as in the preparation of Compound 4 of Example 4, except that Intermediate C-2 (14.2 g, 34.6 mmol) was used instead of Intermediate A-2.

Example 7: Preparation of Compound 7

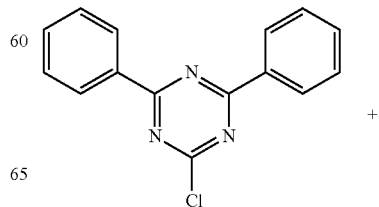

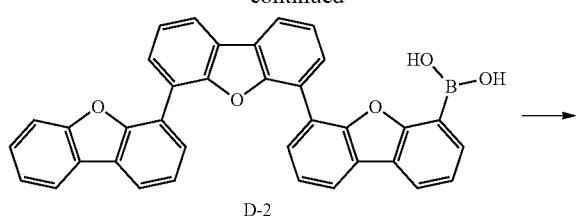

D-2

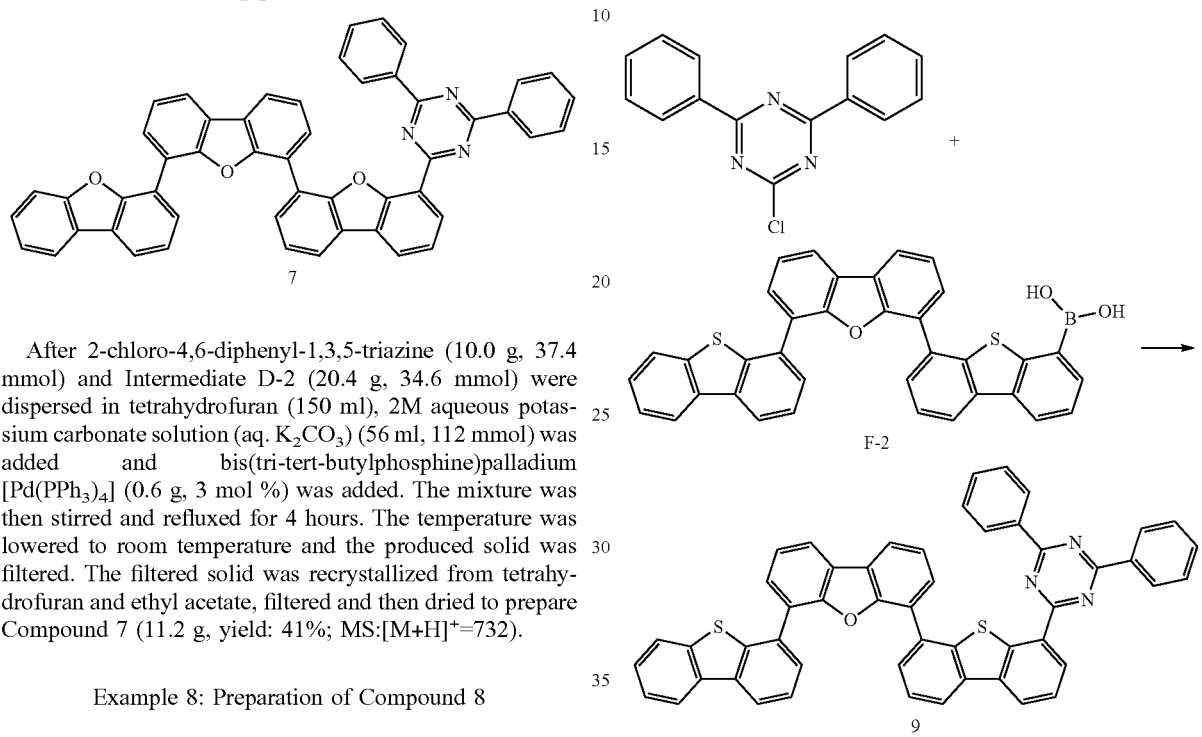

7

After 2-chloro-4,6-diphenyl-1,3,5-triazine (10.0 g, 37.4 mmol) and Intermediate D-2 (20.4 g, 34.6 mmol) were dispersed in tetrahydrofuran (150 ml), 2M aqueous potassium carbonate solution (aq. $K_2CO_3$) (56 ml, 112 mmol) was added and bis(tri-tert-butylphosphine)palladium [Pd(PPh$_3$)$_4$] (0.6 g, 3 mol %) was added. The mixture was then stirred and refluxed for 4 hours. The temperature was lowered to room temperature and the produced solid was filtered. The filtered solid was recrystallized from tetrahydrofuran and ethyl acetate, filtered and then dried to prepare Compound 7 (11.2 g, yield: 41%; MS:[M+H]$^+$=732).

Example 8: Preparation of Compound 8

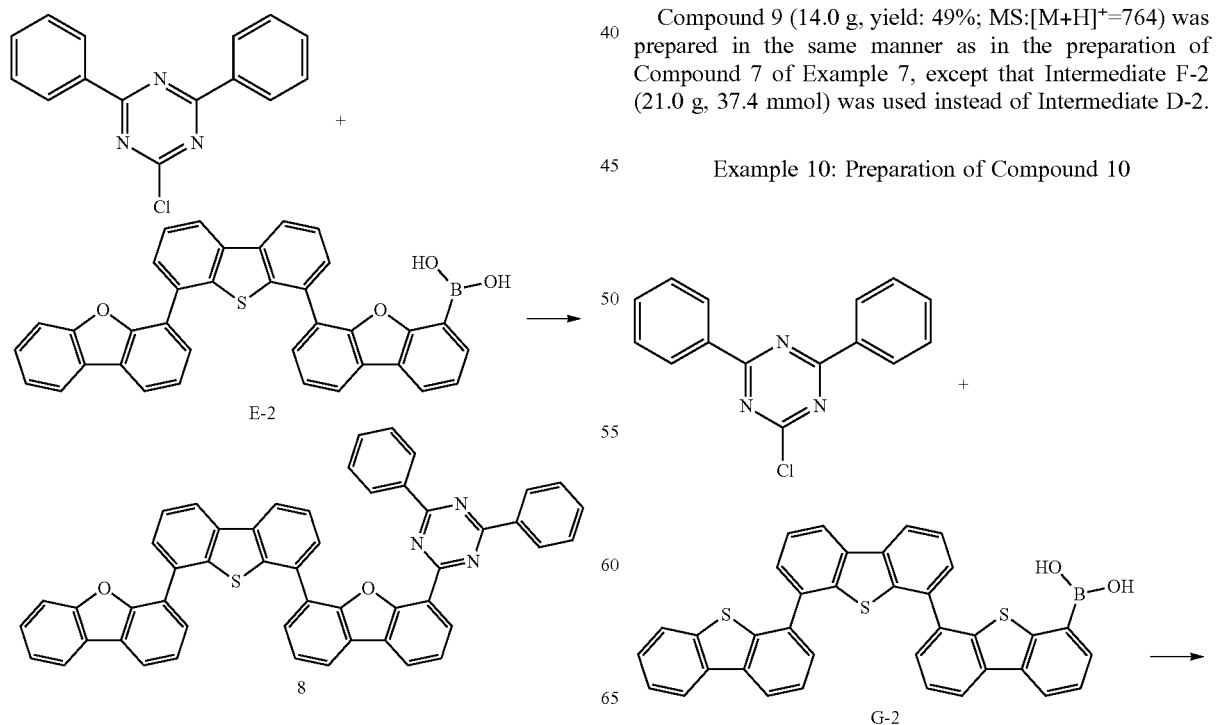

Compound 8 (14.8 g, yield: 53%; MS:[M+H]$^+$=748) was prepared in the same manner as in the preparation of Compound 7 of Example 7, except that Intermediate E-2 (21.0 g, 37.4 mmol) was used instead of Intermediate D-2.

Example 9: Preparation of Compound 9

Compound 9 (14.0 g, yield: 49%; MS:[M+H]$^+$=764) was prepared in the same manner as in the preparation of Compound 7 of Example 7, except that Intermediate F-2 (21.0 g, 37.4 mmol) was used instead of Intermediate D-2.

Example 10: Preparation of Compound 10

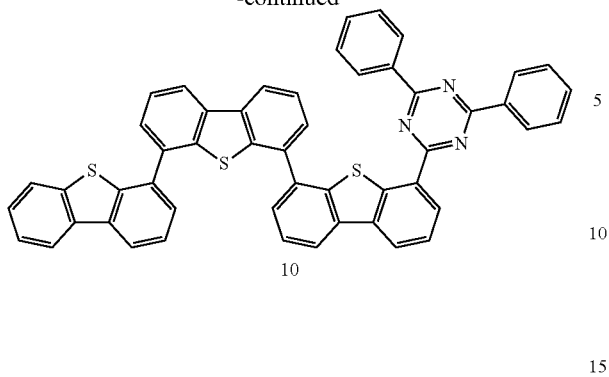

10

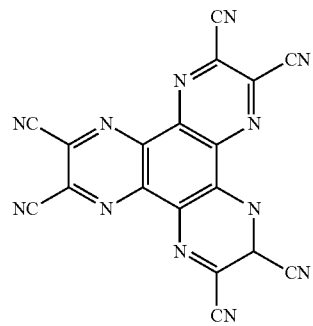

HI-1

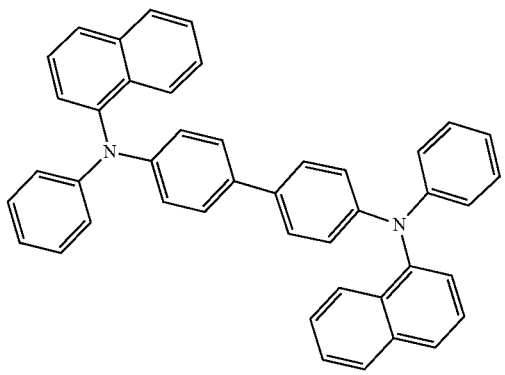

HT-1

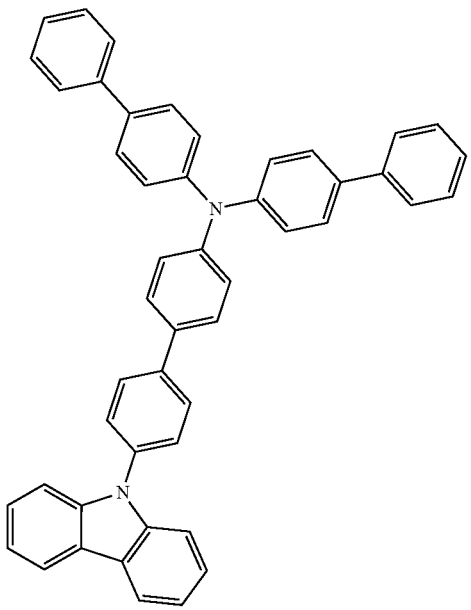

HT-2

Compound 10 (12.8 g, yield: 44%; MS:[M+H]$^+$=780) was prepared in the same manner as in the preparation of Compound 7 of Example 7, except that Intermediate G-2 (21.0 g, 37.4 mmol) was used instead of Intermediate D-2.

Experimental Example 1

A glass substrate on which ITO (indium tin oxide) was coated as a thin film to a thickness of 1,300 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, the following compound HI-1 was thermally vacuum-deposited to a thickness of 50 Å to form a hole injection layer. The following compound HT-1 was thermally vacuum-deposited on the hole injection layer to a thickness of 250 Å to form a hole transport layer, and the following compound HT-2 was vacuum-deposited on the hole transport layer to a thickness of 50 Å to form an electron blocking layer. The compound 1 prepared in the previous Example 1, the following compound YGH-1, and a phosphorescent dopant YGD-1 were co-deposited in a weight ratio of 44:44:12 on the electron blocking layer to form a light emitting layer with a thickness of 400 Å. The following compound ET-1 was vacuum-deposited on the light emitting layer to a thickness of 250 Å to form an electron transport layer, and the following compound ET-2 and Li were vacuum-deposited in a weight ratio of 98:2 on the electron transport layer to form an electron injection layer with a thickness of 100 Å. Aluminum was deposited on the electron injection layer to a thickness of 1000 Å to form a cathode.

YGH-1

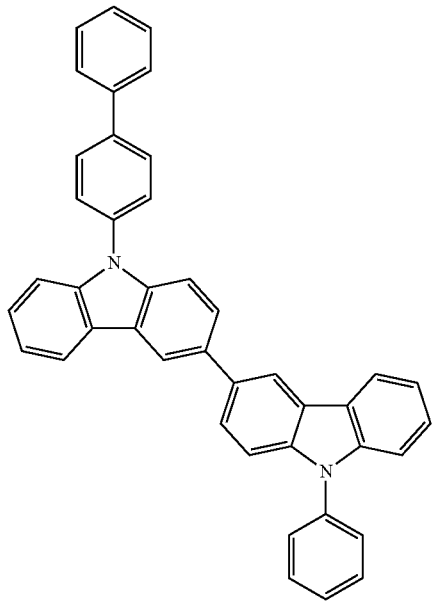

YGD-1

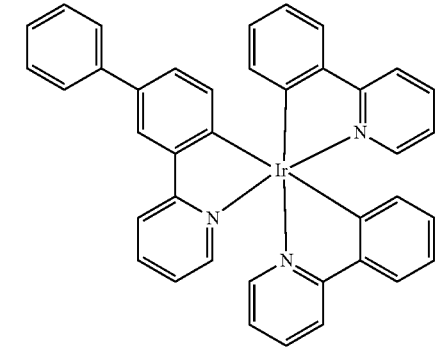

ET-1

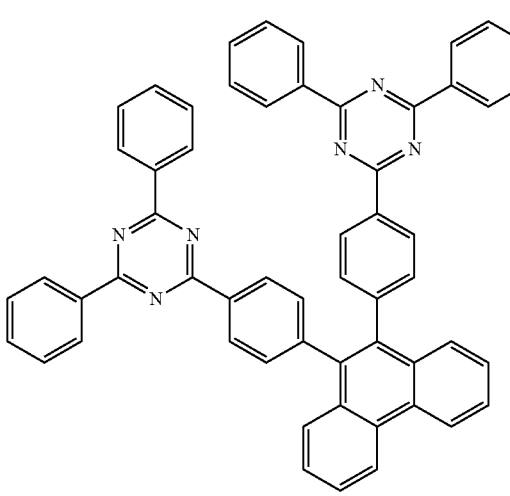

ET-2

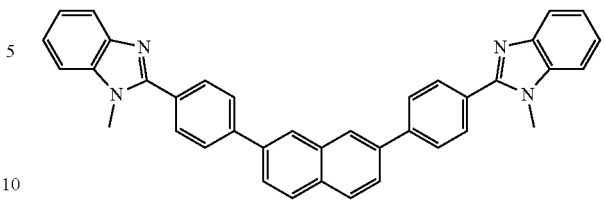

In the above-mentioned process, the vapor deposition rate of the organic material was maintained at 0.4 to 0.7 Å/sec, the deposition rate of aluminum was maintained at 2 Å/sec, and the degree of vacuum during the deposition was maintained at $1\times10^{-7}$ to $5\times10^{-8}$ torr.

Experimental Examples 2 to 10

An organic light emitting device was manufactured in the same manner as in Experimental Example 1, except that the compounds shown in Table 1 below were used instead of Compound 1 in Experimental Example 1.

Comparative Experimental Examples 1 to 4

An organic light emitting device was manufactured in the same manner as in Experimental Example 1, except that the compounds shown in Table 1 below were used instead of Compound 1 in Experimental Example 1.

On the other hand, the compounds of CE1 to CE4 shown in Table 1 are as follows.

CE1

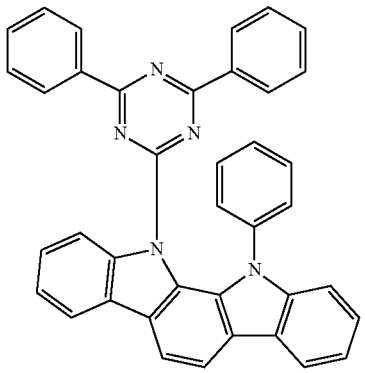

CE2

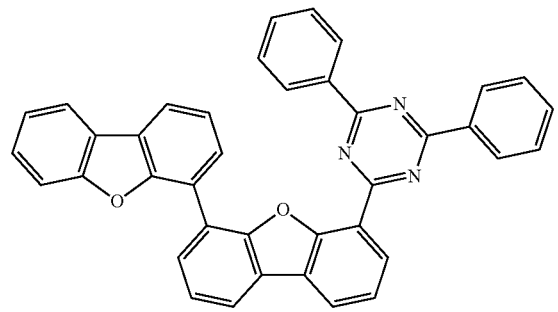

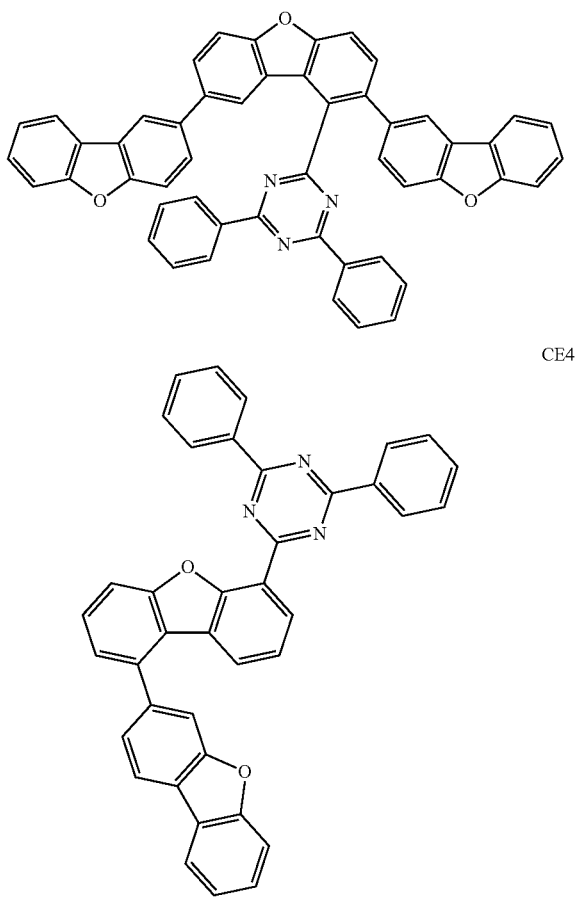

CE3

CE4

For the organic light emitting devices manufactured in Experimental Examples and Comparative Experimental Examples, the voltage and efficiency were measured at a current density of 10 mA/cm² and the lifetime was measured at a current density of 50 mA/cm². The results are shown in Table 1 below. In this case, LT95 means the time required for the luminance to be reduced to 95% of the initial luminance.

TABLE 1

| Compound | Voltage (V) (@10 mA/cm²) | Efficiency (Cd/A) (@10 mA/cm²) | Color coordinate (x, y) | Lifetime (hr) ($LT_{95}$ at 50 mA/cm²) |
|---|---|---|---|---|
| Experimental Example 1 | Compound 1 | 4.0 | 80 | 0.45, 0.53 | 120 |
| Experimental Example 2 | Compound 2 | 4.1 | 78 | 0.46, 0.53 | 130 |
| Experimental Example 3 | Compound 3 | 4.0 | 77 | 0.46, 0.54 | 115 |
| Experimental Example 4 | Compound 4 | 4.2 | 79 | 0.46, 0.54 | 140 |
| Experimental Example 5 | Compound 5 | 4.1 | 78 | 0.46, 0.53 | 115 |
| Experimental Example 6 | Compound 6 | 4.0 | 78 | 0.46, 0.54 | 160 |
| Experimental Example 7 | Compound 7 | 4.2 | 80 | 0.46, 0.54 | 142 |
| Experimental Example 8 | Compound 8 | 4.3 | 78 | 0.46, 0.54 | 130 |
| Experimental Example 9 | Compound 9 | 4.2 | 79 | 0.46, 0.53 | 125 |
| Experimental Example 10 | Compound 10 | 4.3 | 77 | 0.46, 0.54 | 100 |
| Comparative Experimental Example 1 | CE1 | 4.4 | 70 | 0.46, 0.54 | 90 |
| Comparative Experimental Example 2 | CE2 | 4.5 | 67 | 0.46, 0.55 | 45 |
| Comparative Experimental Example 3 | CE3 | 4.4 | 75 | 0.45, 0.54 | 80 |
| Comparative Experimental Example 4 | CE4 | 4.5 | 73 | 0.45, 0.55 | 65 |

As shown in Table 1, it was confirmed that the organic light emitting device using the compound of the present invention as an organic light emitting layer material exhibited excellent characteristics in terms of efficiency and lifetime as compared with Comparative Experimental Examples. This is predicted that as three dibenzofuran or dibenzothiophene groups were substituted, the electrical stability was increased.

EXPLANATION OF SIGN

1: substrate 2: anode
3: light emitting layer 4: cathode
5: hole injection layer
6: hole transport layer
7: electron blocking layer
8: electron transport layer
9: electron injection layer

What is claimed is:
1. A compound of the following Chemical Formula 1-1:
Chemical Formula 1-1

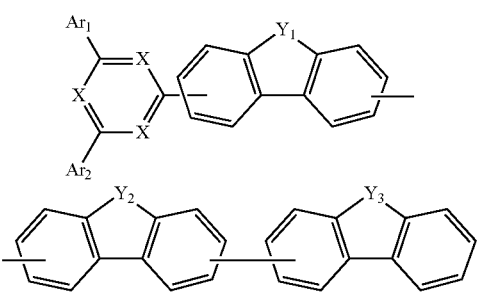

wherein, in Chemical Formula 1-1,
each X is independently N or CH, with the proviso that at least two of X are N,
$Y_1$, $Y_2$ and $Y_3$ are each independently O or S, and
$Ar_1$ and $Ar_2$ are each independently substituted or unsubstituted $C_{6-60}$ aryl.
2. The compound according to claim 1, wherein each X is N.
3. The compound according to claim 1, wherein $Ar_1$ and $Ar_2$ are phenyl.

4. The compound according to claim 1, wherein the compound of Chemical Formula 1-1 is one selected from the group consisting of the following compounds:
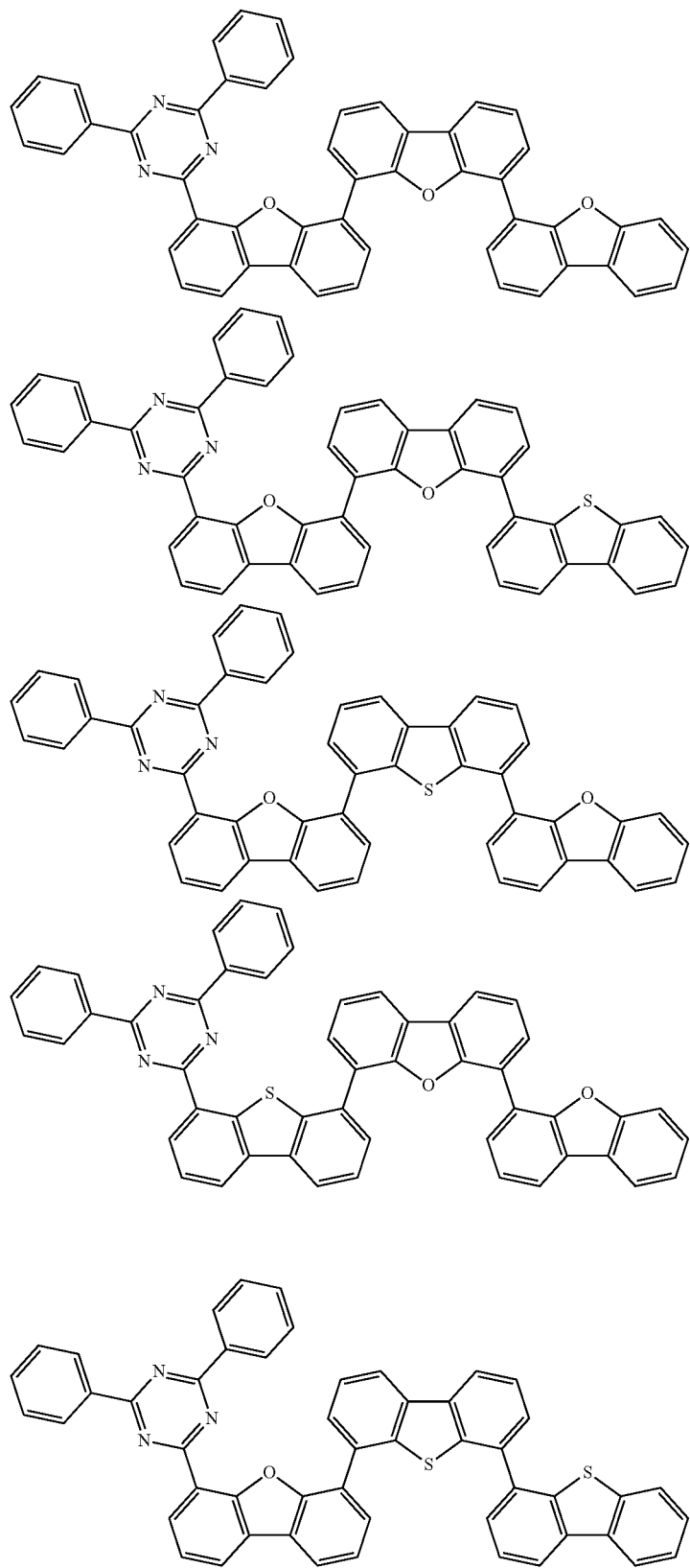

-continued
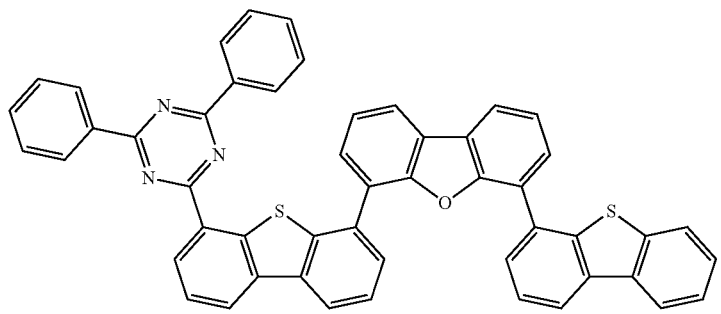
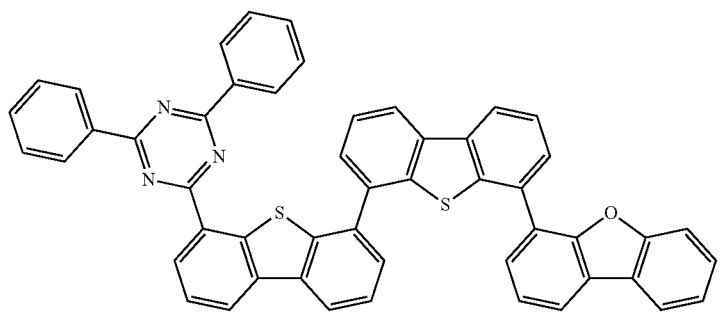
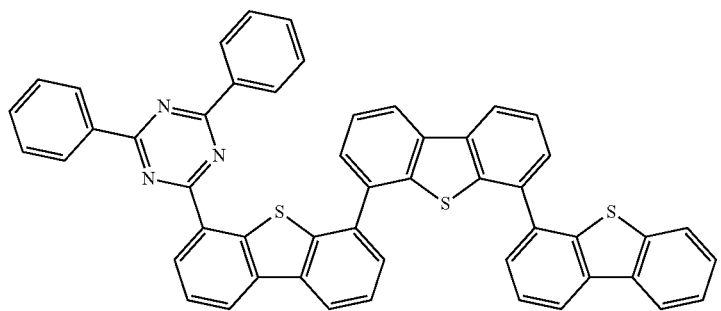
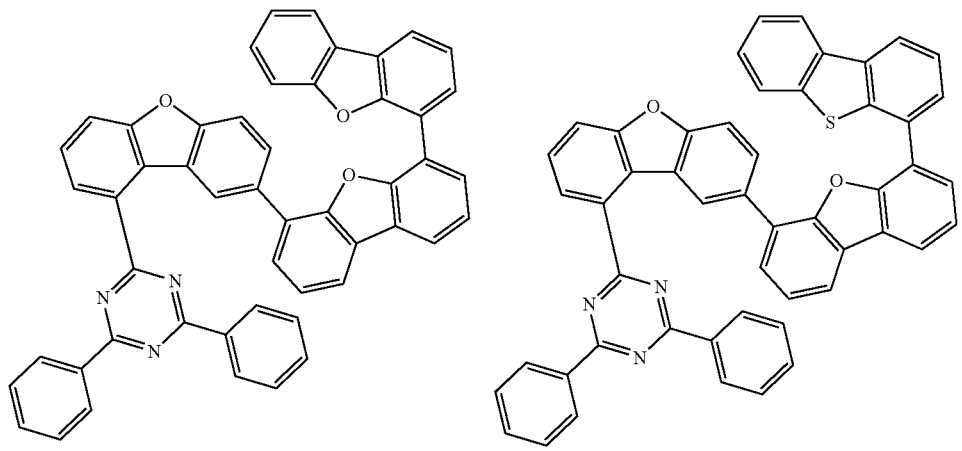

-continued
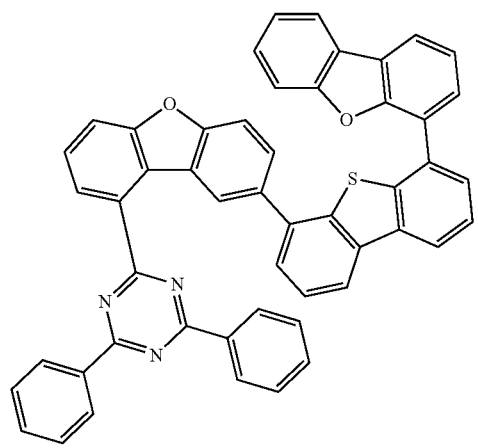
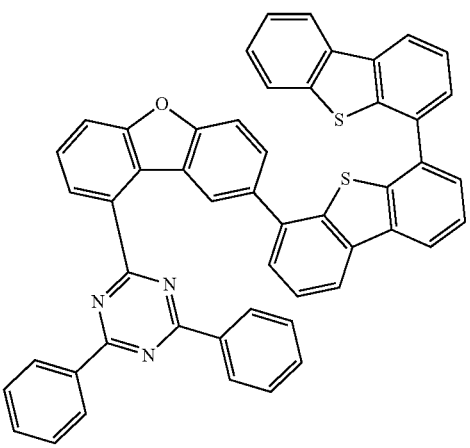
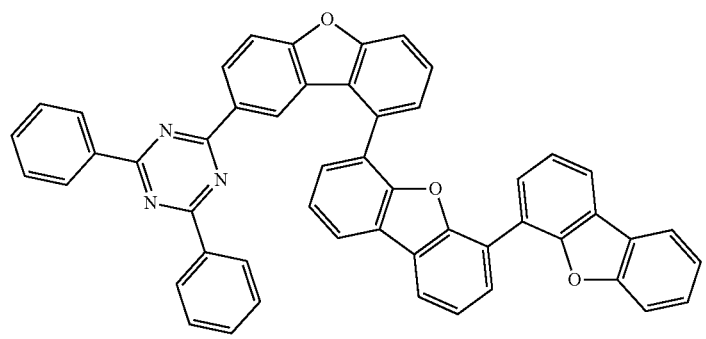
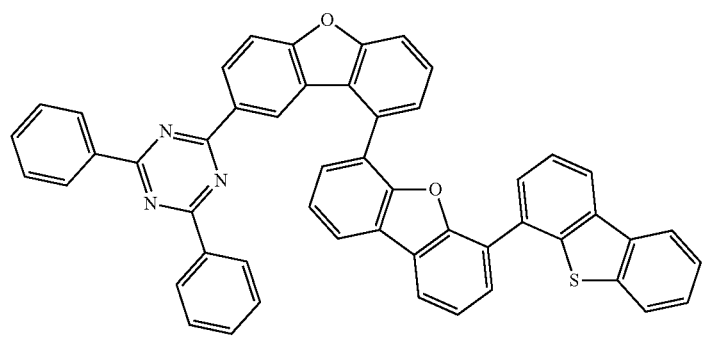
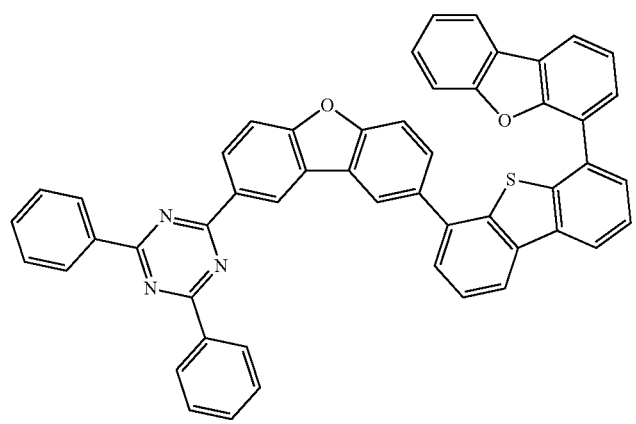

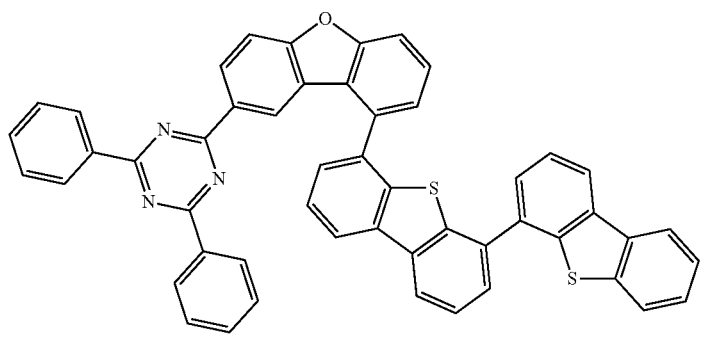
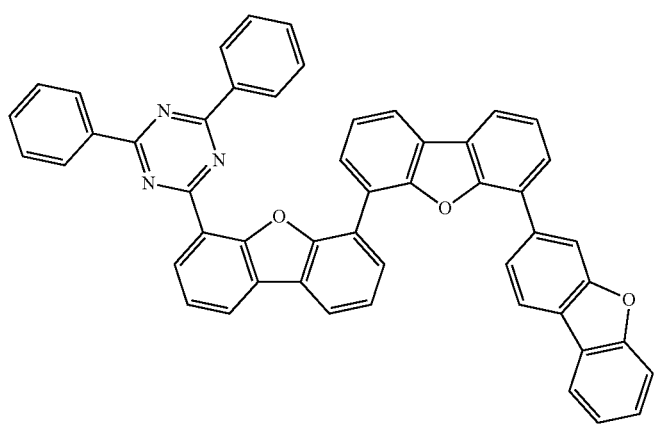
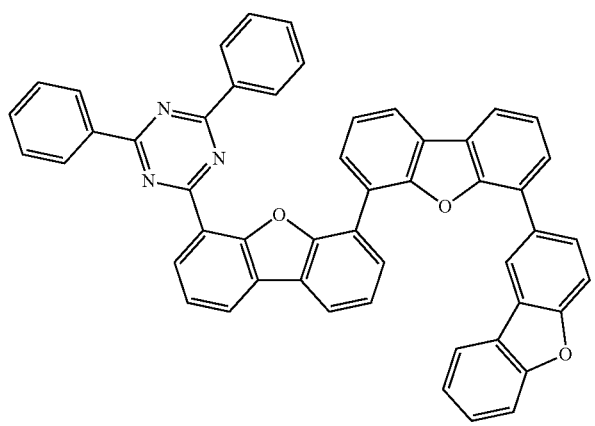
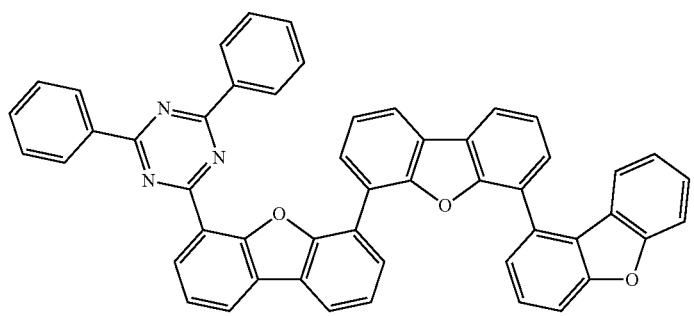

-continued
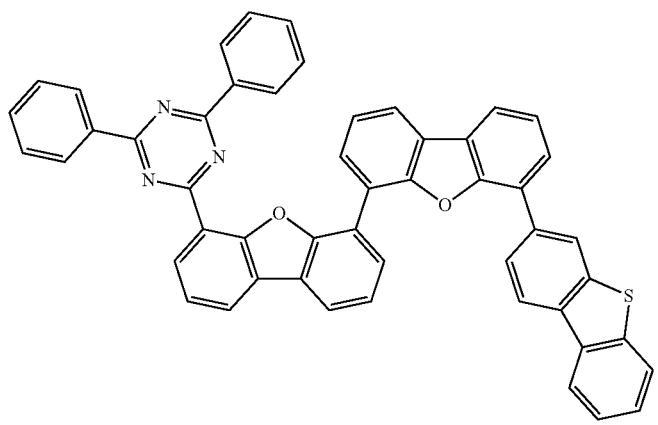
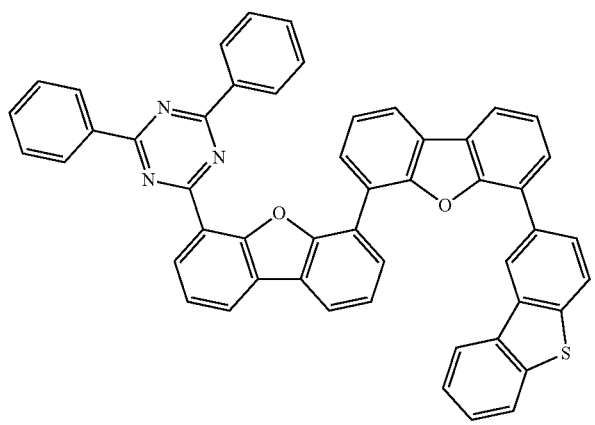
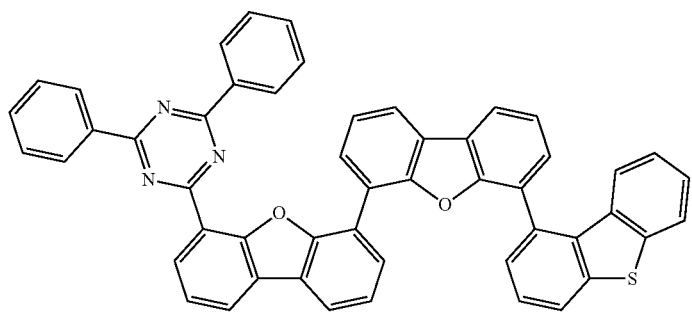
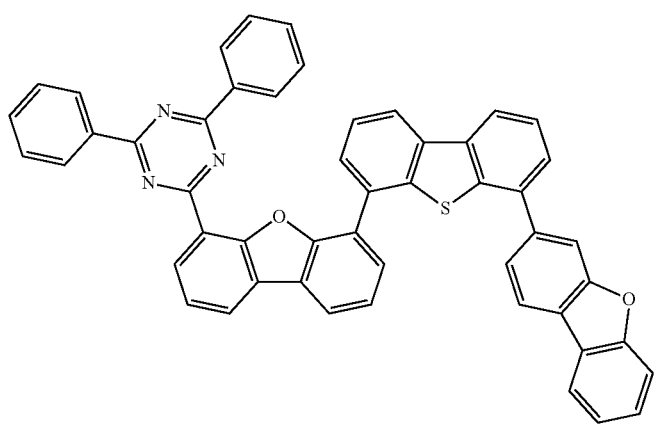

-continued
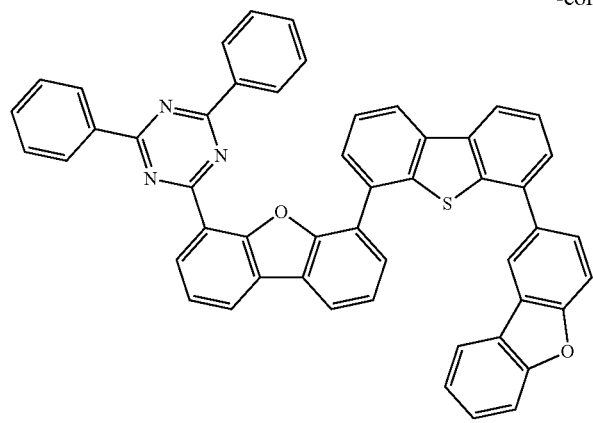
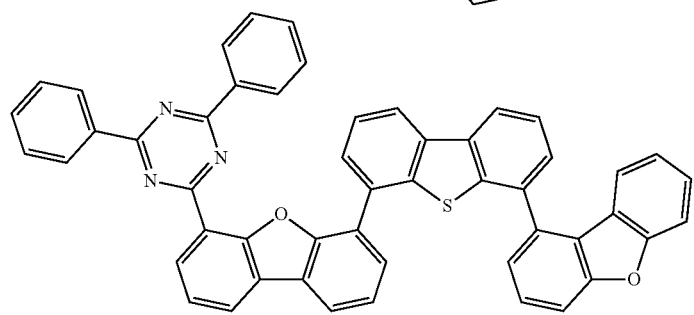
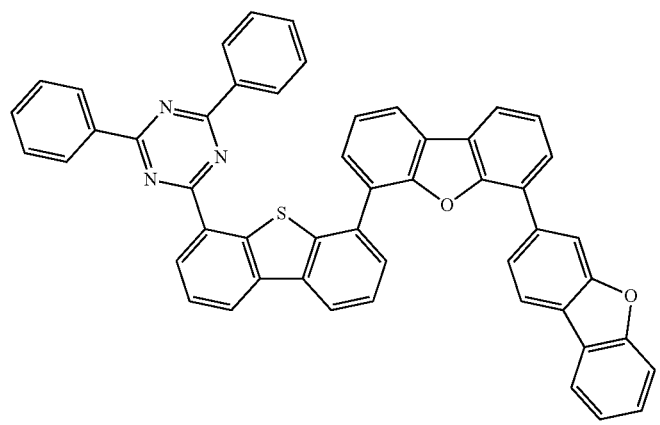
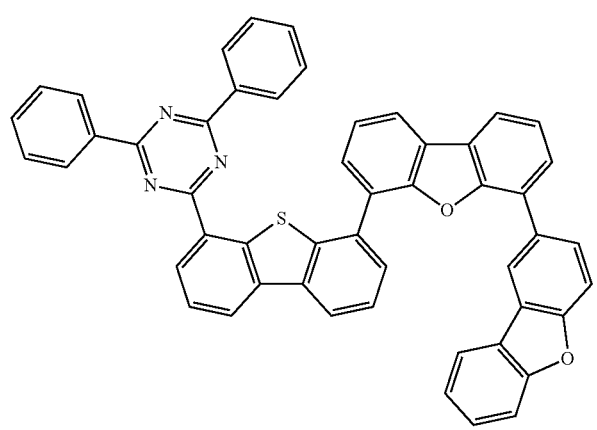

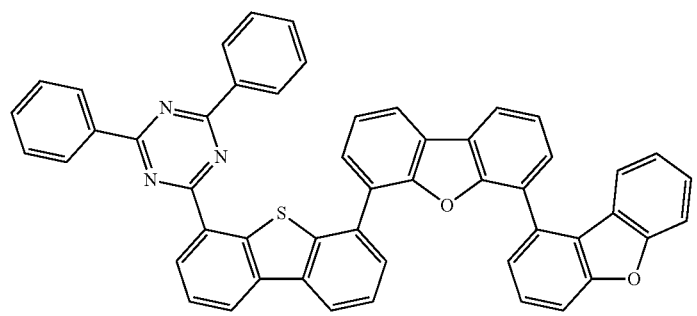
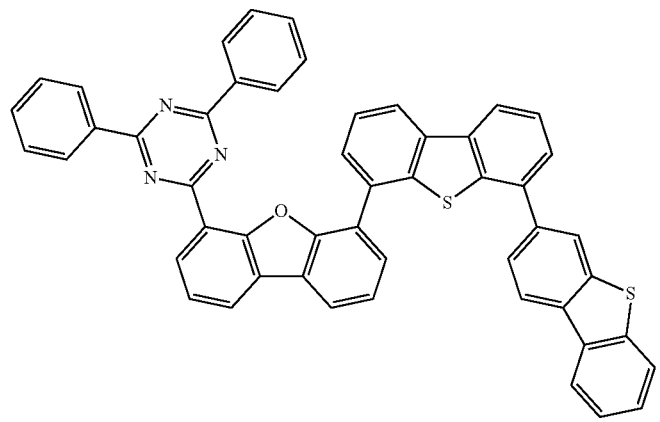
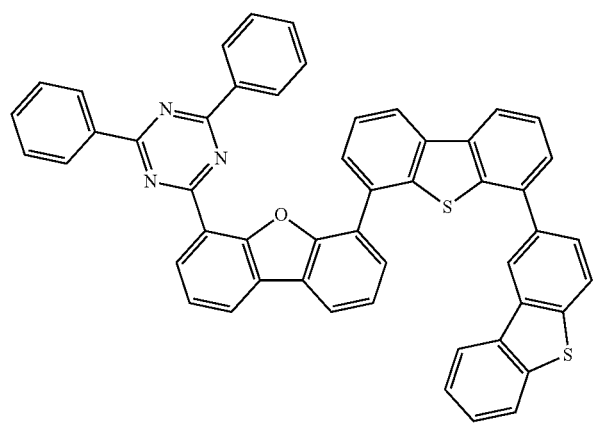
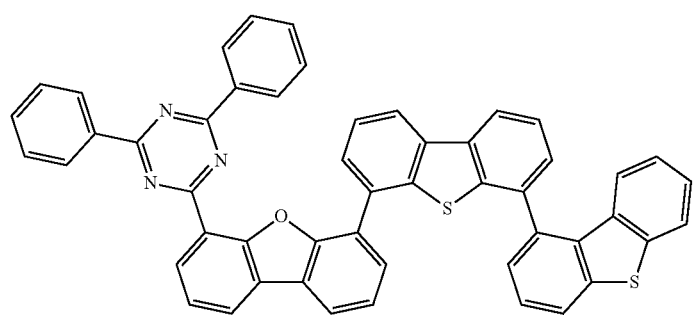

-continued
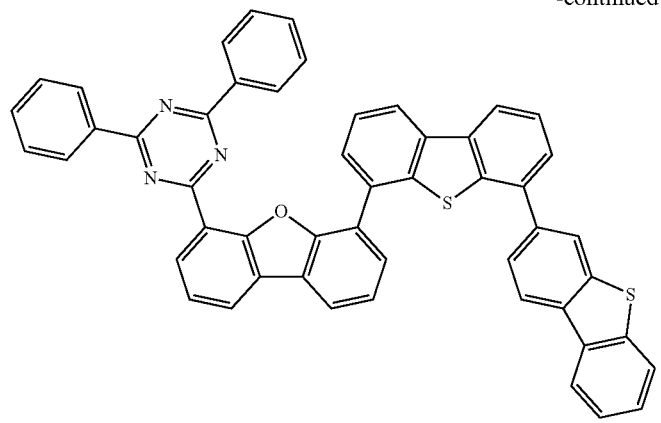

-continued
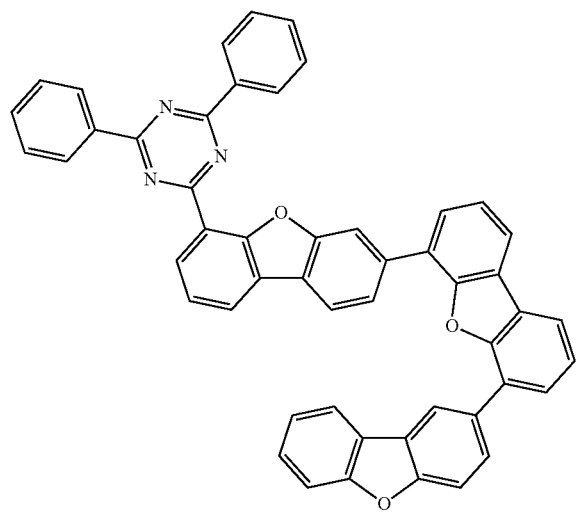
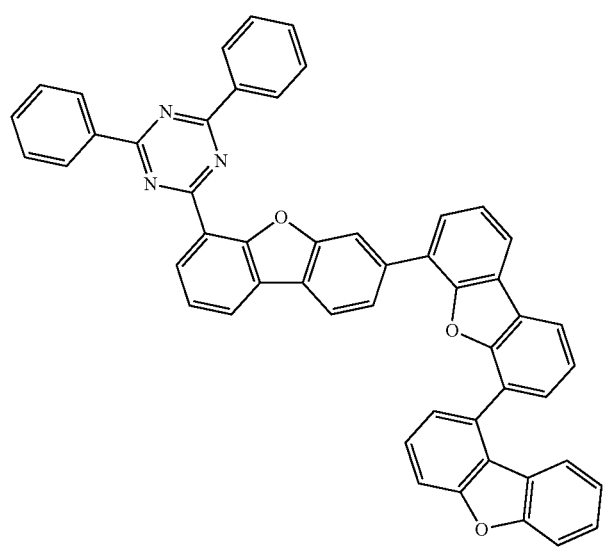
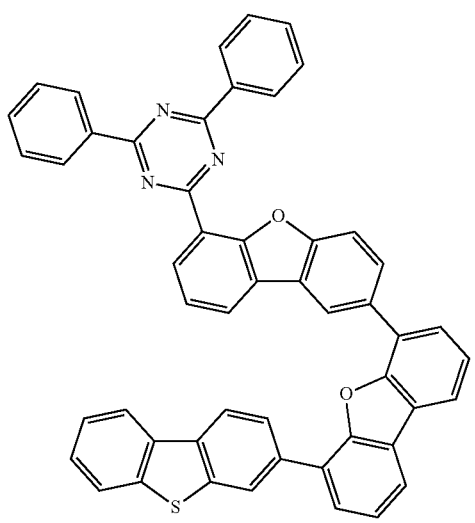
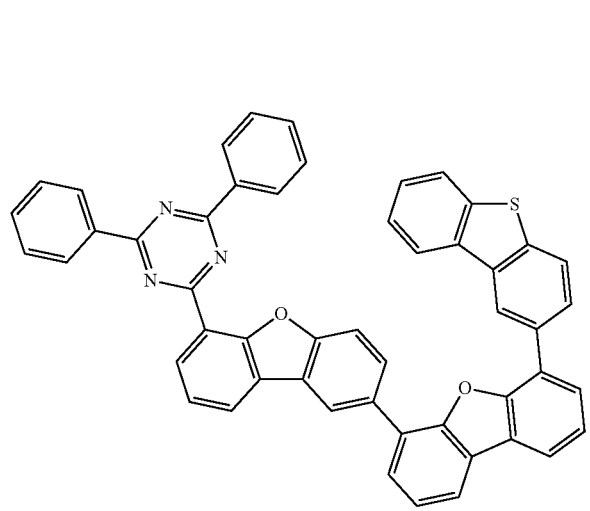
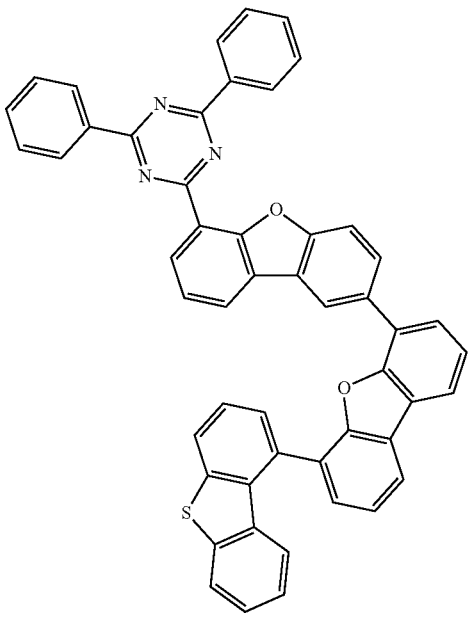

-continued
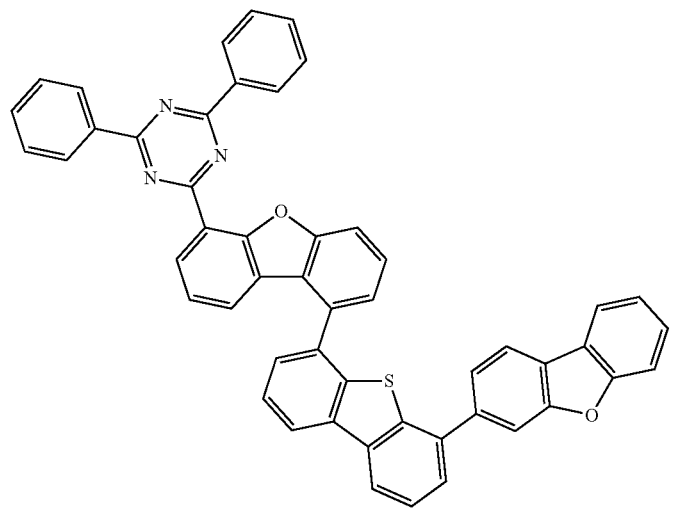
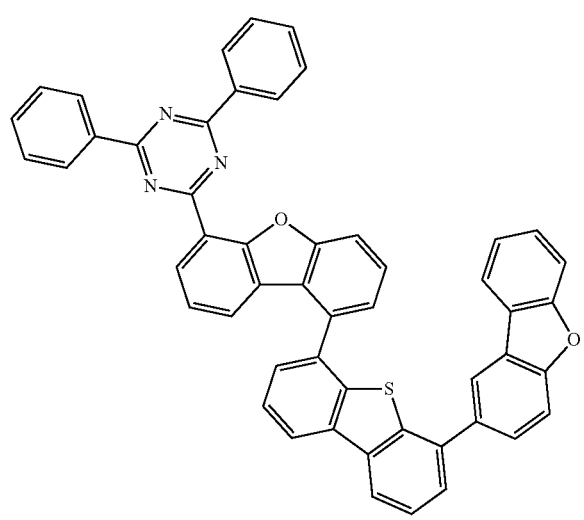
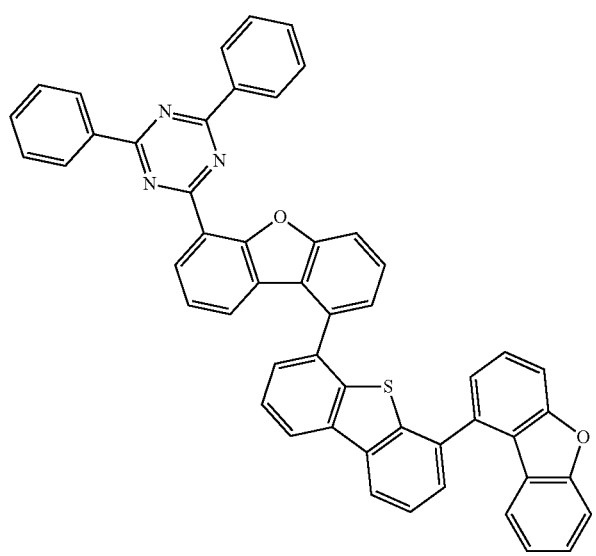
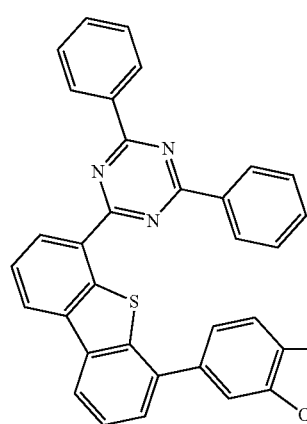
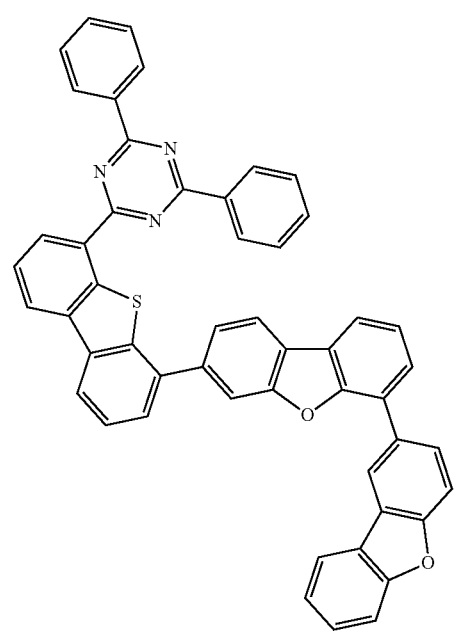

95 96
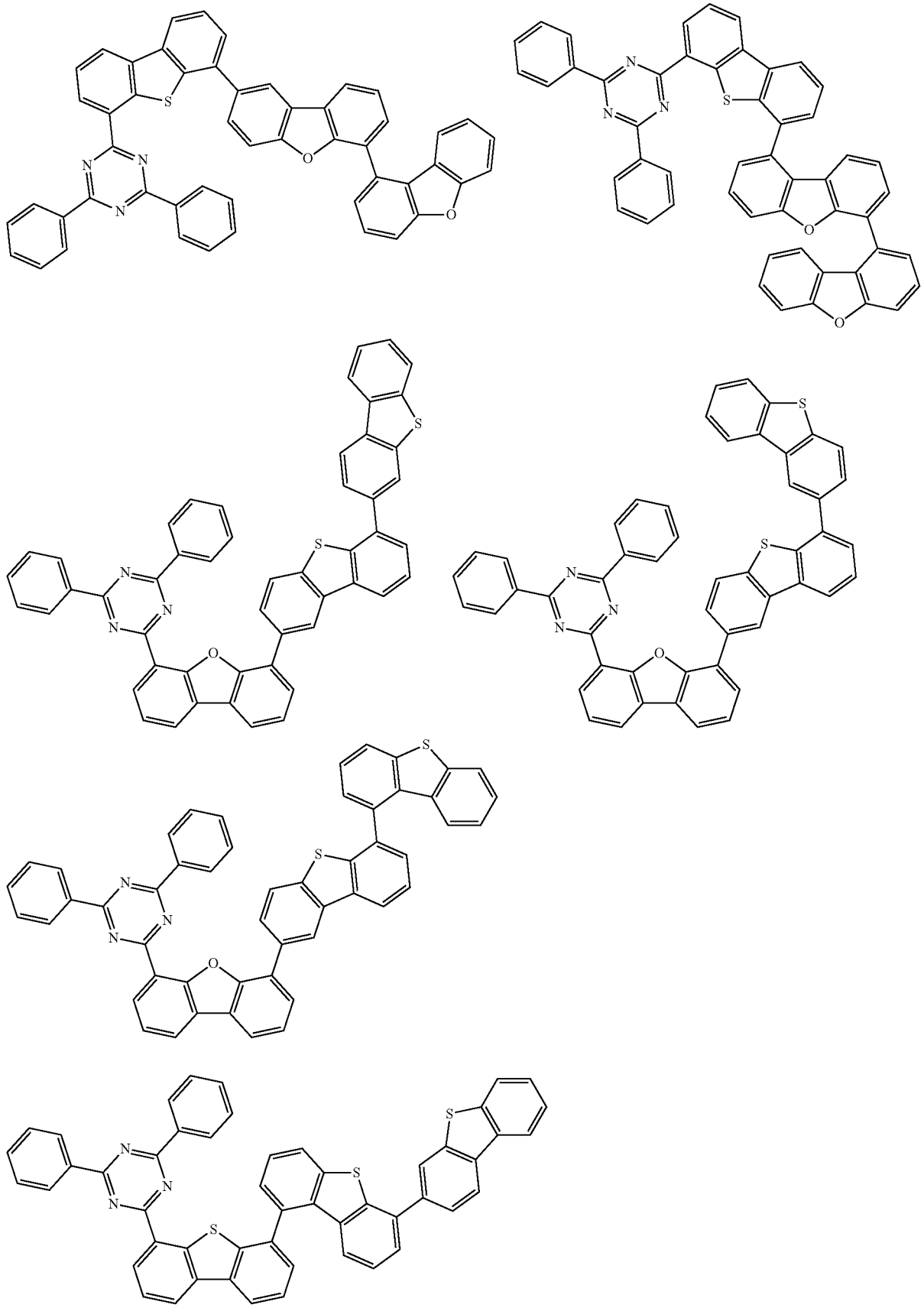

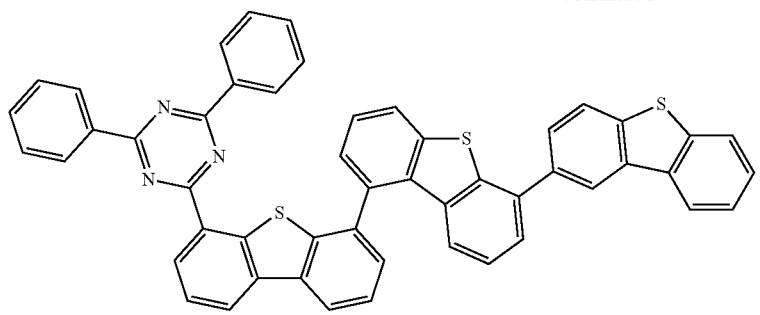
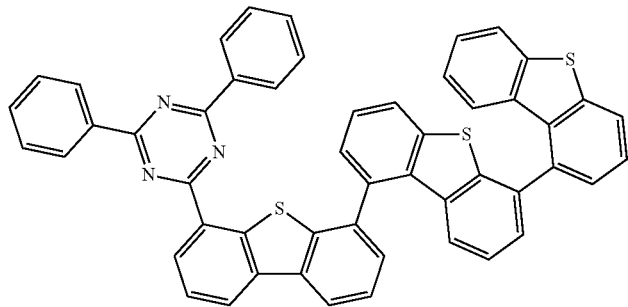
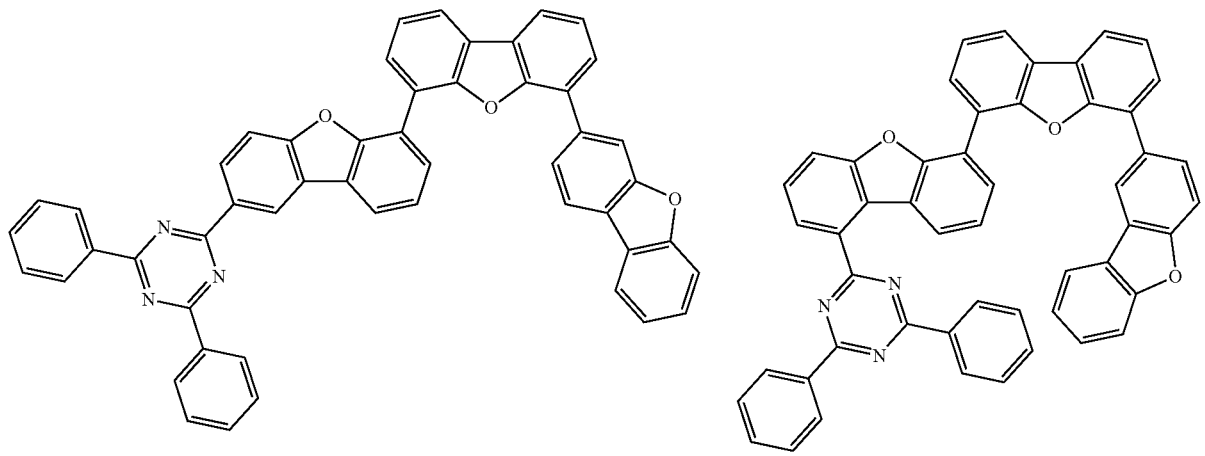
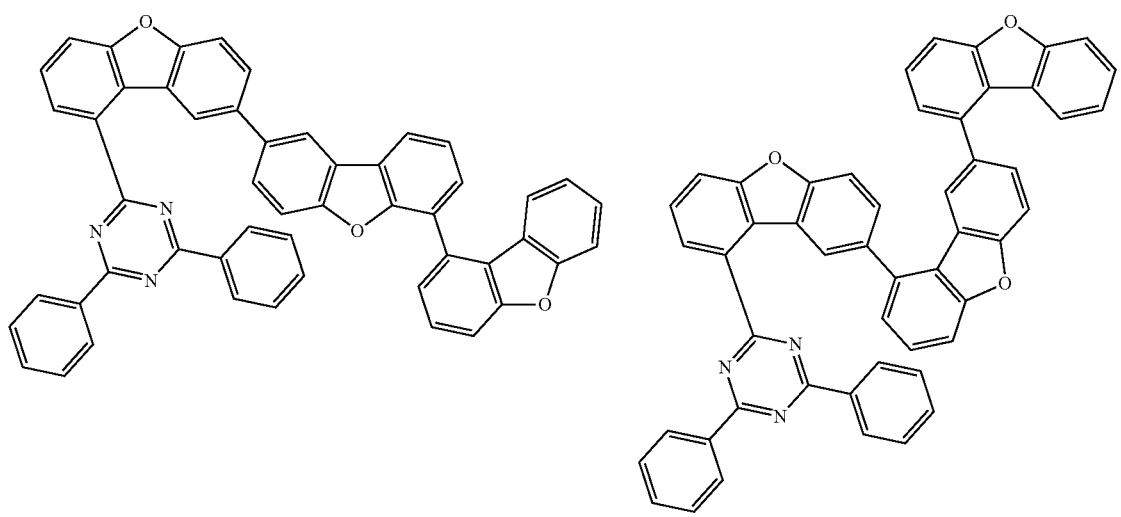

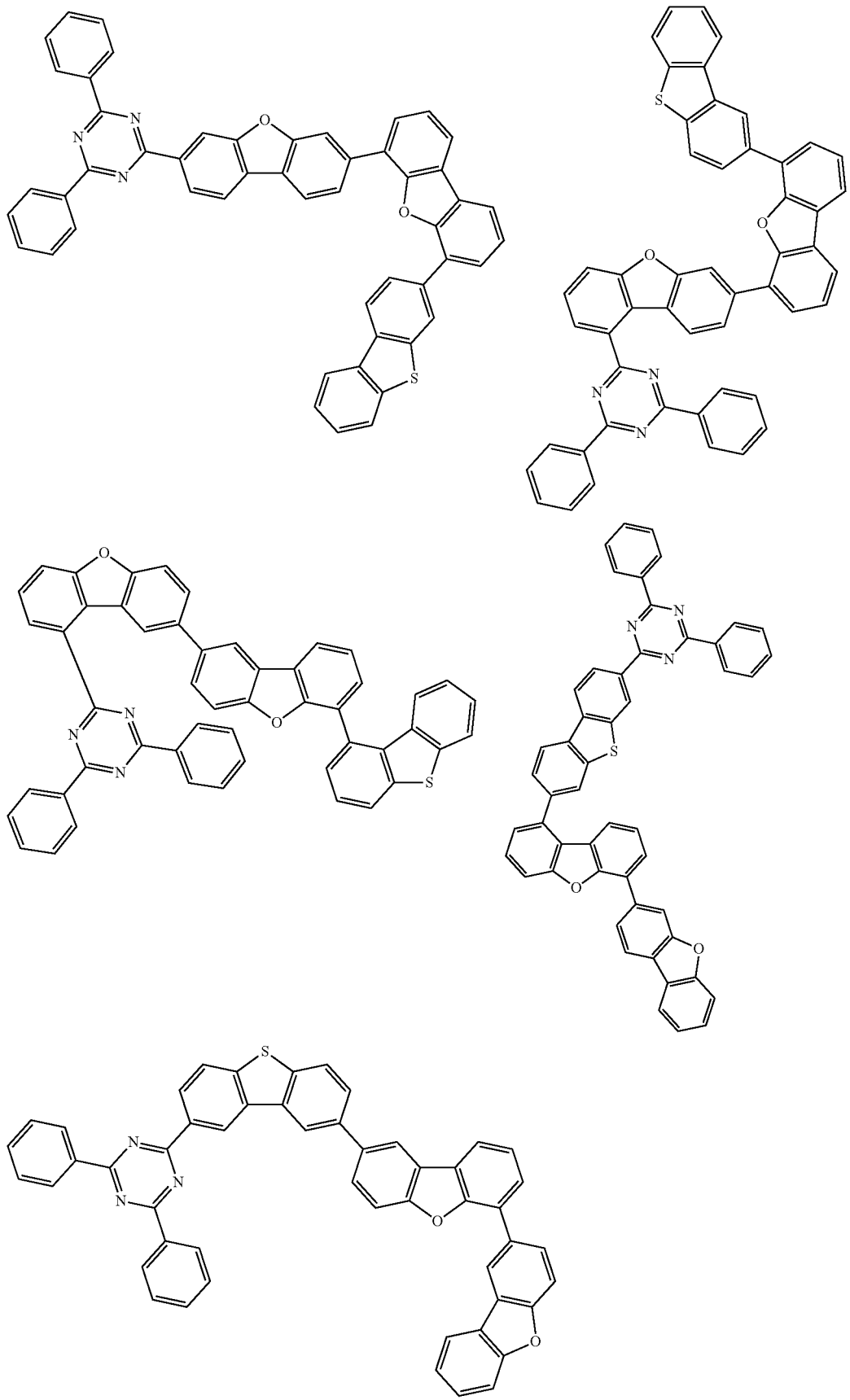

101 102
-continued
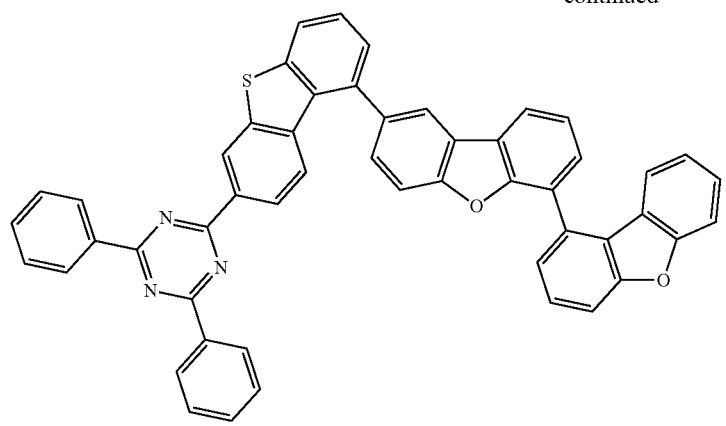
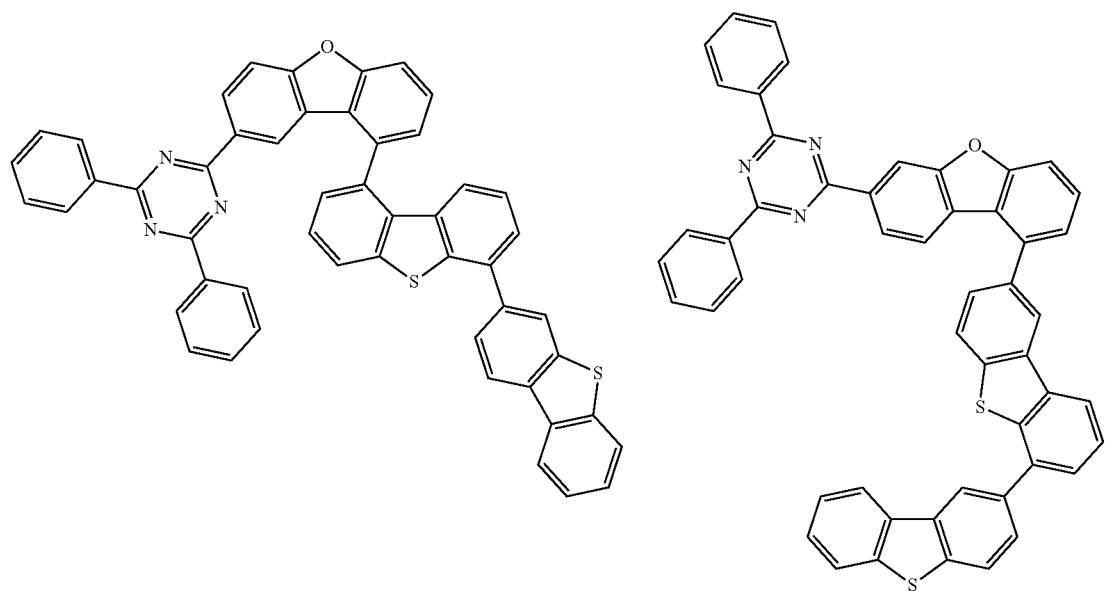
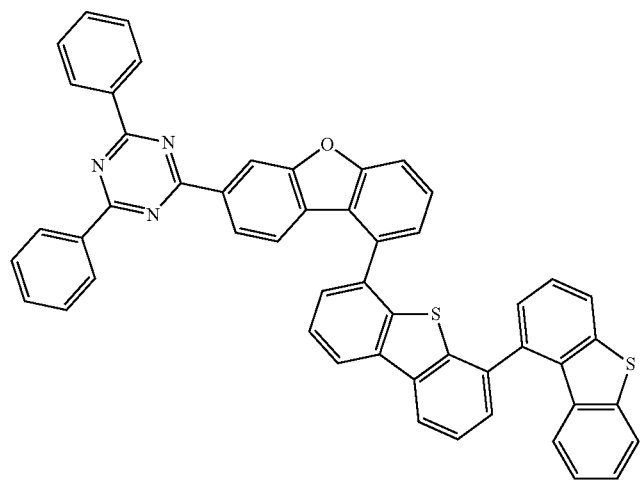

103 104
-continued
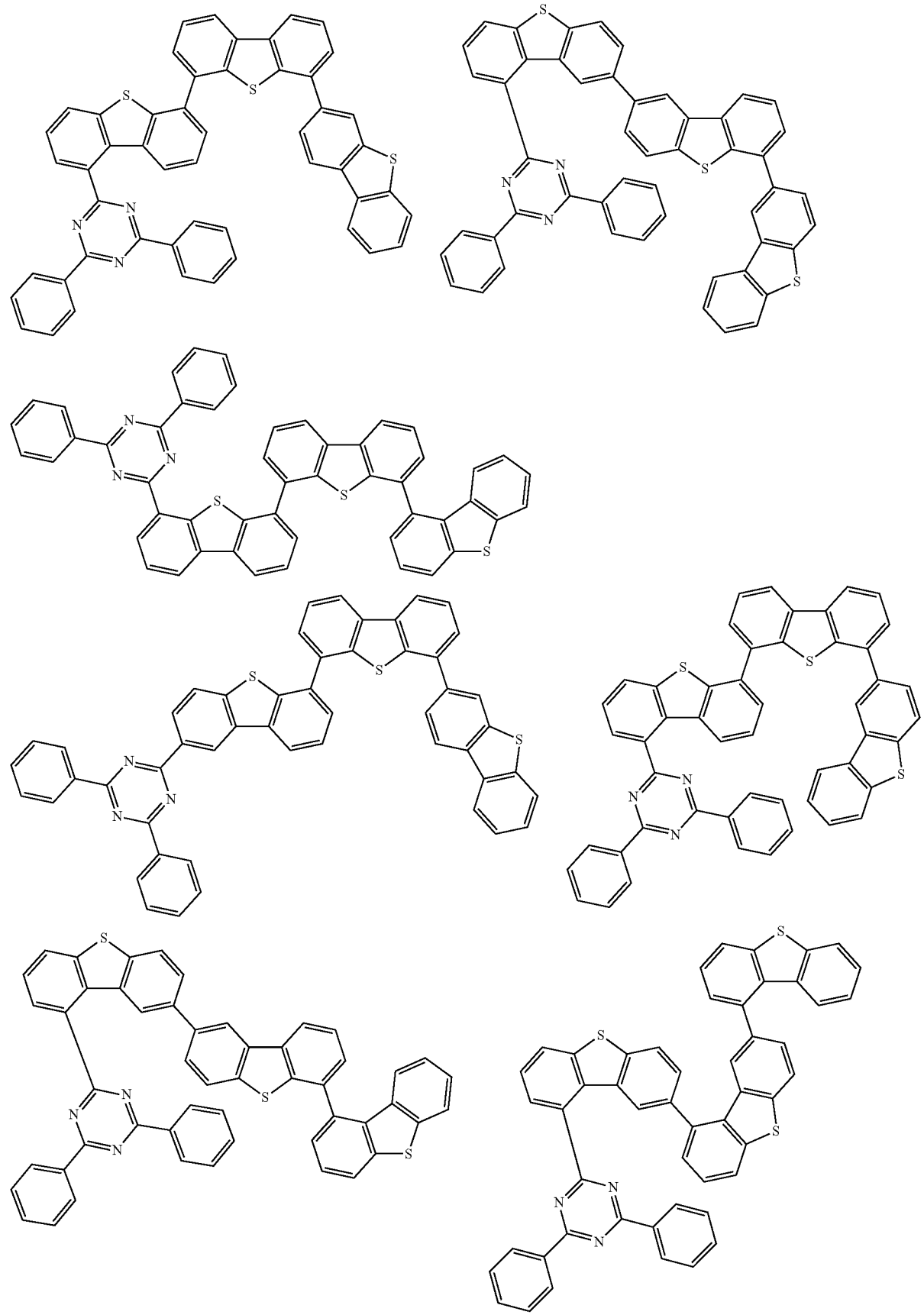

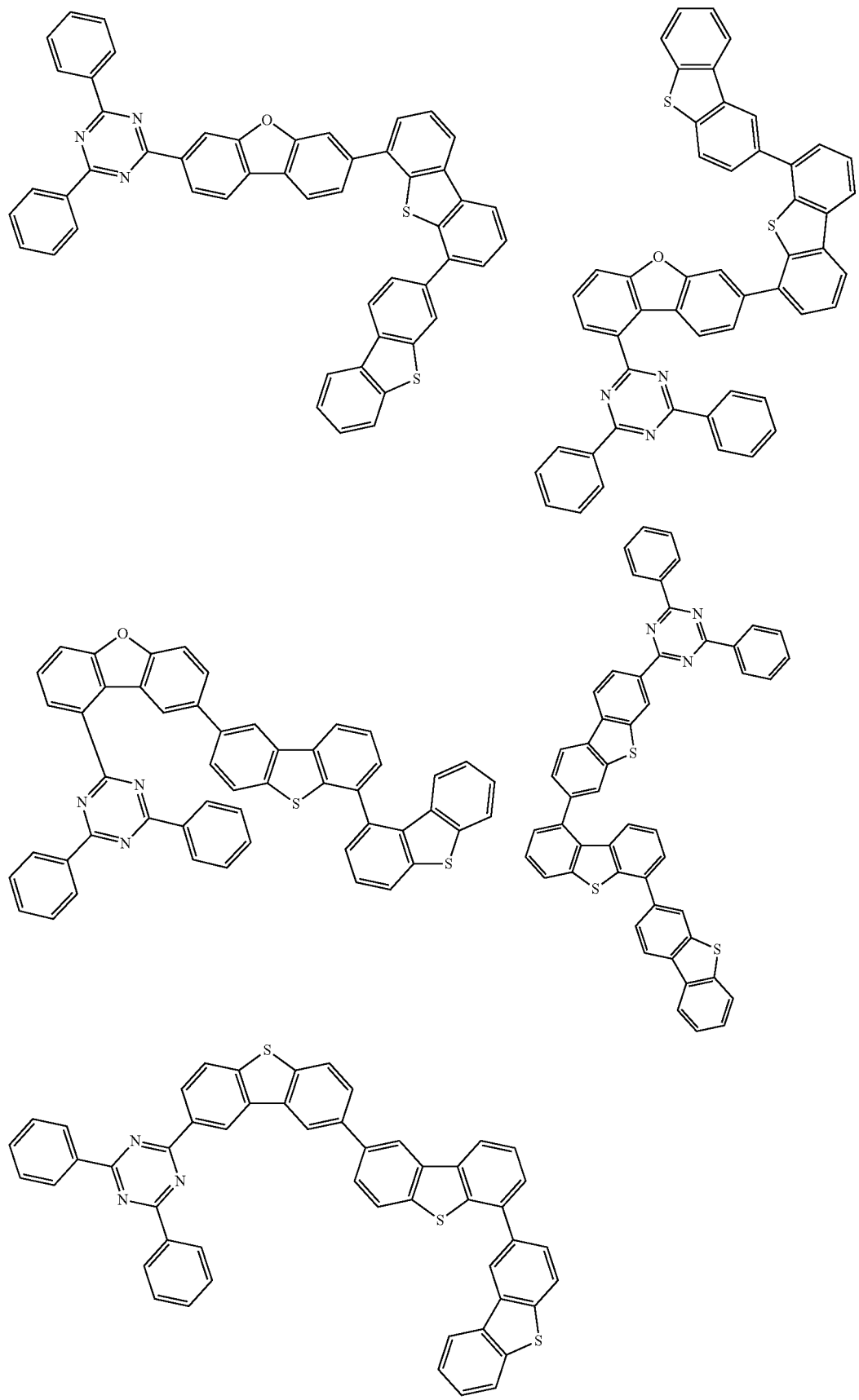

-continued
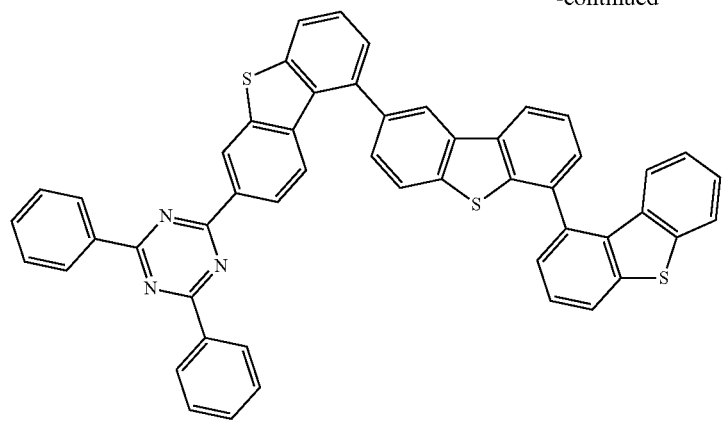
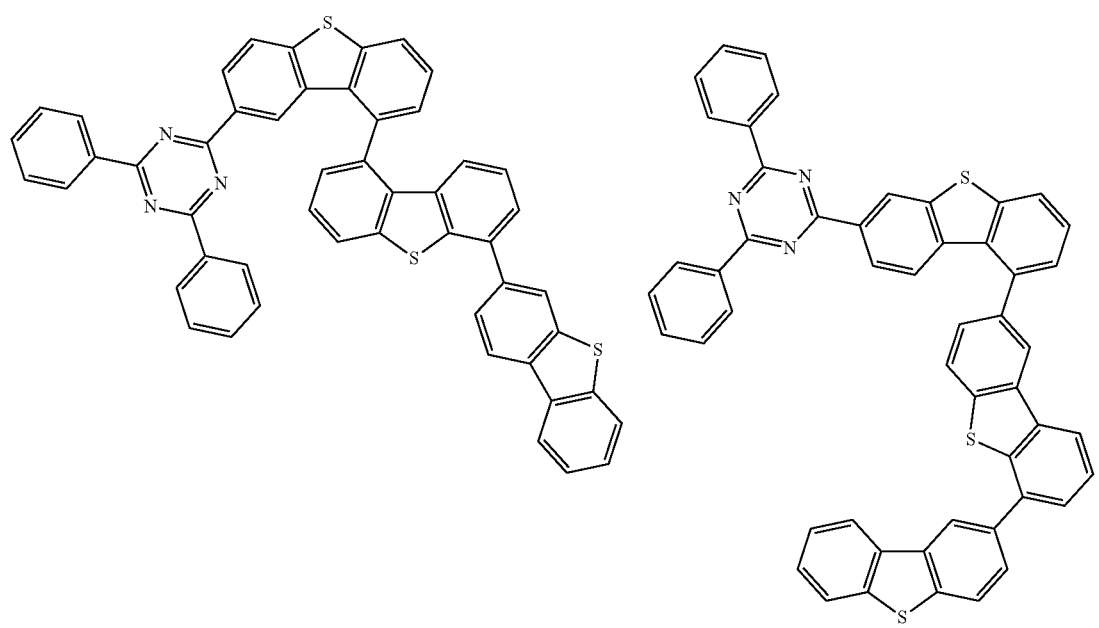
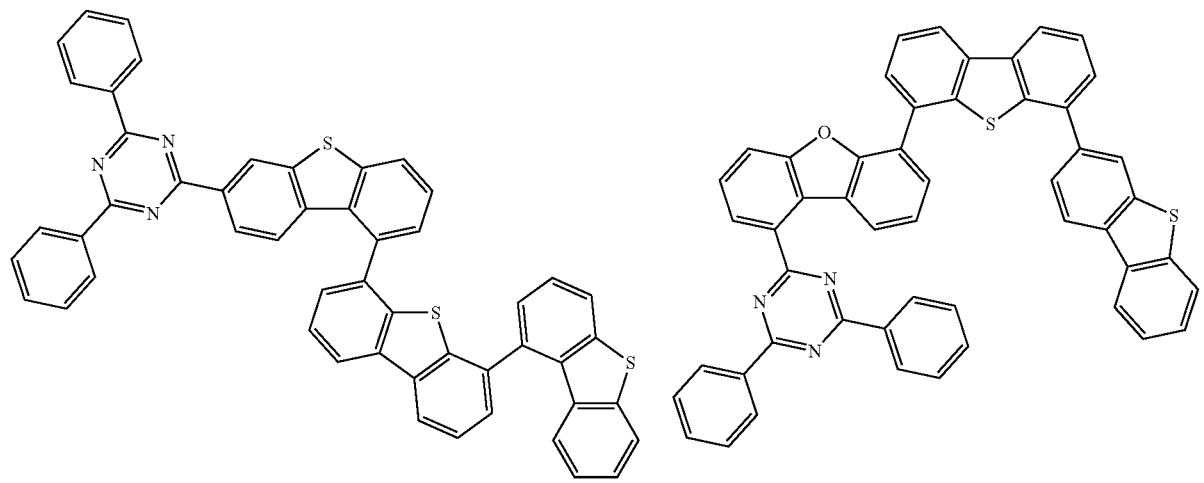

-continued
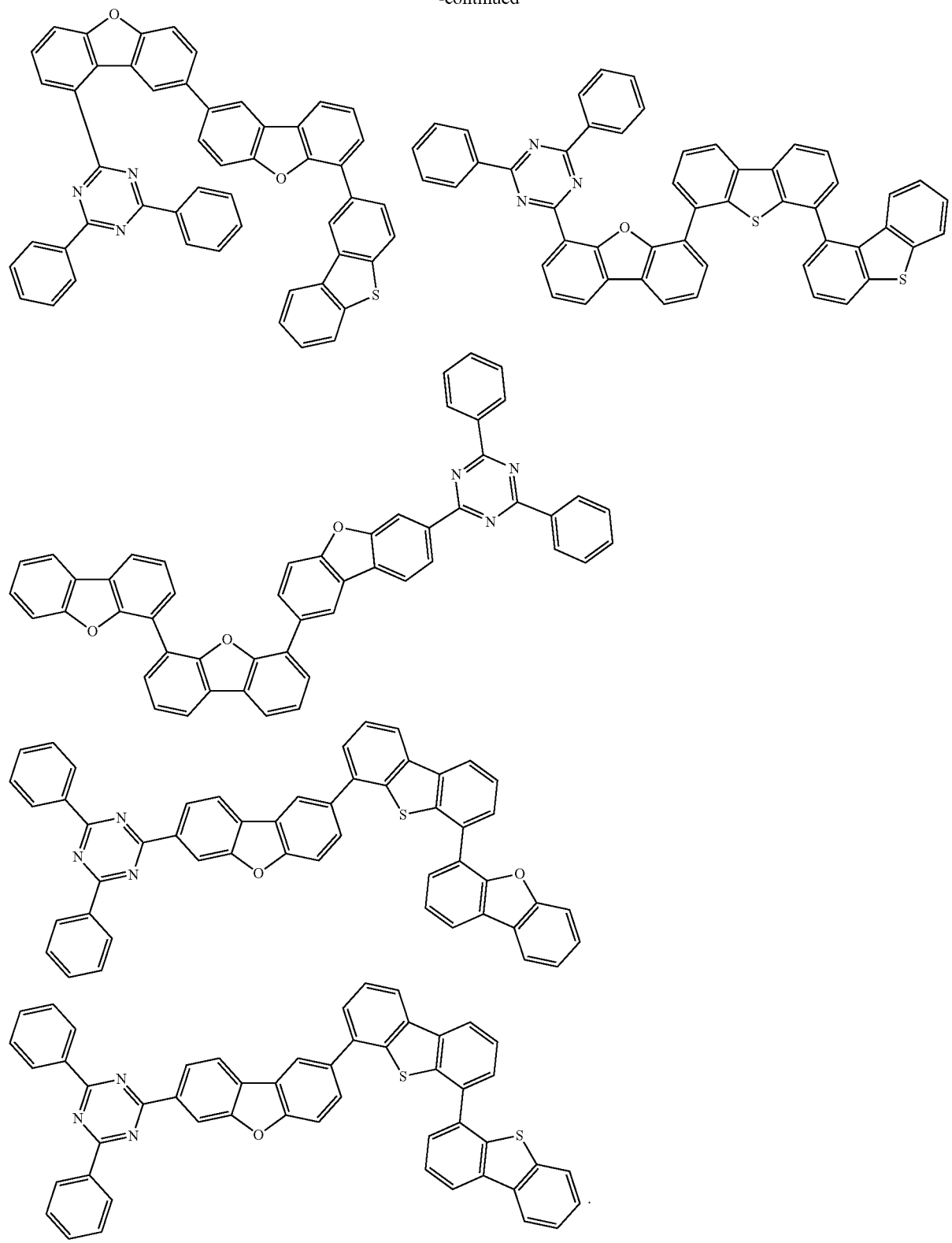
5. An organic light emitting device comprising:
a first electrode;
a second electrode that is disposed opposite to the first electrode; and
one or more organic material layers that are disposed between the first electrode and the second electrode, wherein one or more one layers of the organic material layers comprise the compound according to claim 1.

6. The organic light emitting device according to claim 5, wherein organic material layer may include a light emitting layer, wherein the light emitting layer includes two or more host materials.

7. The organic light emitting device according to claim 6, wherein the two or more host materials include a compound of Chemical Formula 1-1.

* * * * *

UNITED STATES PATENT AND TRADEMARK OFFICE
CERTIFICATE OF CORRECTION

PATENT NO. : 12,010,912 B2
APPLICATION NO. : 17/049820
DATED : June 11, 2024
INVENTOR(S) : Jung et al.

Page 1 of 1

It is certified that error appears in the above-identified patent and that said Letters Patent is hereby corrected as shown below:

In the Claims

In Claim 4, at Column 89, the structure of the first compound should be:

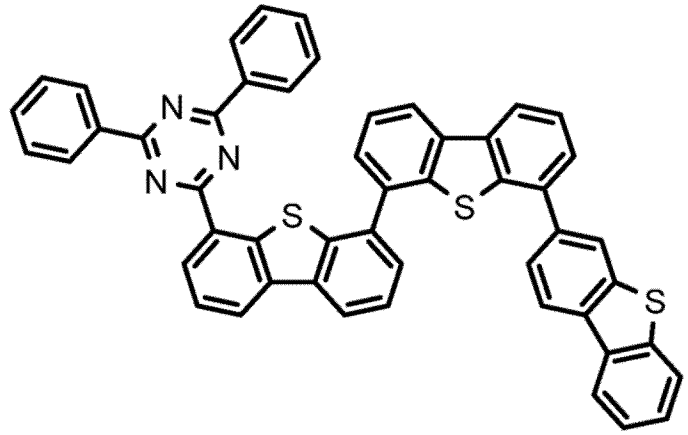

Signed and Sealed this
Thirtieth Day of July, 2024

Katherine Kelly Vidal
Director of the United States Patent and Trademark Office